(12) United States Patent
Ge et al.

(10) Patent No.: US 12,304,884 B2
(45) Date of Patent: May 20, 2025

(54) PHOTO-CLEAVABLE SURFACTANTS

(71) Applicant: Wisconsin Alumni Research Foundation, Madison, WI (US)

(72) Inventors: Ying Ge, Madison, WI (US); Song Jin, Madison, WI (US); Tania Guardado Alvarez, Madison, WI (US); Kyle Brown, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 90 days.

(21) Appl. No.: 18/069,005

(22) Filed: Dec. 20, 2022

(65) Prior Publication Data

US 2023/0139837 A1 May 4, 2023

Related U.S. Application Data

(62) Division of application No. 16/972,881, filed as application No. PCT/US2019/035447 on Jun. 4, 2019, now Pat. No. 11,567,085.
(Continued)

(51) Int. Cl.
*C07C 381/00* (2006.01)
*B01D 57/02* (2006.01)
(Continued)

(52) U.S. Cl.
CPC .......... *C07C 381/00* (2013.01); *C07C 309/14* (2013.01); *C07C 309/15* (2013.01);
(Continued)

(58) Field of Classification Search
CPC ..... C07C 381/00; C07C 309/15; B01D 57/02; B01D 15/38; G01N 27/26; G01N 27/44747

See application file for complete search history.

(56) References Cited

U.S. PATENT DOCUMENTS 6,537,432 B1 3/2003 Schneider et al.
8,697,447 B2 4/2014 Caprioli et al.
(Continued)

OTHER PUBLICATIONS

Bradley, M., et al., Photoresponsive surfactants in microgel dispersions, Langmuir, vol. 22, No. 1, pp. 101-105 (Year: 2005).*
(Continued)

*Primary Examiner* — Yate' K Cutliff
(74) *Attorney, Agent, or Firm* — LEYDIG, VOIT & MAYER, LTD.

(57) ABSTRACT

The present invention provides photo-cleavable anionic surfactants, particularly 4-hexylphenylazosulfonate (Azo) and sodium 4-hexylphenylazosulfonate derivatives, which can be rapidly degraded upon UV irradiation, for top-down and bottom-up proteomics. These surfactants can effectively solubilize proteins and peptide fragments with performance comparable to sodium dodecyl sulfate (SDS) and are compatible with mass spectrometry analysis of the solubilized proteins and peptide fragments. Top-down proteomic studies using the present photo-cleavable anionic surfactants has allowed the detection of 100-fold more unique proteoforms as compared to controls and has enabled the solubilization of membrane proteins for comprehensive characterization of protein post-translational modifications. In addition, the present photo-cleavable anionic surfactants are also suitable for dissolving polypeptides in bottom-up proteomic experiments including extracellular matrix proteomics, and are suitable as a substitute for SDS in gel electrophoresis.

6 Claims, 39 Drawing Sheets

Related U.S. Application Data

(60) Provisional application No. 62/682,027, filed on Jun. 7, 2018, provisional application No. 62/810,744, filed on Feb. 26, 2019.

(51) Int. Cl.
    *C07C 309/14*      (2006.01)
    *C07C 309/15*      (2006.01)
    *G01N 27/26*      (2006.01)
    *G01N 27/447*      (2006.01)
    *G01N 33/68*      (2006.01)
    *B01D 15/38*      (2006.01)

(52) U.S. Cl.
CPC ....... *G01N 27/26* (2013.01); *G01N 27/44747* (2013.01); *G01N 33/68* (2013.01); *G01N 33/6842* (2013.01); *G01N 33/6848* (2013.01); *B01D 15/38* (2013.01); *B01D 57/02* (2013.01)

(56) References Cited

U.S. PATENT DOCUMENTS

| | | | |
|---|---|---|---|
| 9,816,054 B2 | 11/2017 | Saveliev et al. | |
| 11,567,085 B2 | 1/2023 | Ge et al. | |
| 2018/0299463 A1 | 10/2018 | Piehowski et al. | |
| 2023/0138788 A1 | 5/2023 | Ge et al. | |

OTHER PUBLICATIONS

Dunkin, et al., Synthesis, Characterization and applications of azo-containing photodestructible surfactants, Journal of the Chemical Society, Perkin Transactions, 2, pp. 1837-1842 (Year: 1996).*
Eastoe, J., et al., Light-Sensitive microemulsions, Langmuir, vol. 20, No. 4, pp. 1120-1125 (Year: 2004).*
Aballo et al. (Aug. 2021) Ultrafast and Reproducible Proteomics from Small Amounts of Heart Tissue Enabled by Azo and TimsTOF Pro. J. Proteome Res. 20 (8), 4203-4211.
Aebersold et al. (2016) "Mass-spectrometric exploration of proteome structure and function" Nature 537, 347-355.
Aebersold et al. (Mar. 2018) "How many human proteoforms are there?" Nature Chemical Biology 14, 206-214.
Altelaar et al. (2013) "Next-generation proteomics: towards an integrative view of proteome dynamics" Nature Reviews | Genetics 14, 35-48.
Apweiler et al. (2004) "UniProt: The Universal Protein knowledgebase" Nucleic Acids Research 32, D115-D119.
Barrera et al. (2011) "Advances in the Mass Spectrometry of Membrane Proteins: From Individual Proteins to Intact Complexes" Annu. Rev. Biochem. 80, 247-271.
Bereman et al. (2011) "Comparison between procedures using SDS for shotgun proteomic analyses of complex samples" Proteomics, 11, 2931-2935.
Bogen et al. (2012) "Light-triggered conversion of non-ionic into ionic surfactants: towards cameleon detergents for 2-D gel electrophoresis," Photochemical & Photobiological Sciences, 11, 497-499.
Botelho et al. (2010) "Top-Down and Bottom-Up Proteomics of SDS-Containing Solutions Following Mass-Based Separation" Journal of Proteome Research, 9, 2863-2870.
Bradley et al. (2006) "Photoresponsive Surfactants in Microgel Dispersions," Langmuir vol. 22, 101-105.
Brodbelt (Jan. 2014) Photodissociation mass spectrometry: new tools for characterization of biological molecules. Chem. Soc. Rev., 43(8): 2757-2783.
Brown et al. (Feb. 2020) High-Throughput Proteomics Enabled by a Photocleavable Surfactant. Angew. Chem., Int. Ed. 59 (22), 8406-8410.
Brown et al. (May 2019) A Photocleavable Surfactant for Top-down Proteomics. Nat. Methods 16 (5), 417-420.

Buck et al. (May 2022) "One-Pot Exosome Proteomics Enabled by a Photocleavable Surfactant," with Supporting Information, Anal. Chem. 94, 20, 7164-7168.
Buck et al. (Nov. 2021) "Rapid Exosome Proteomics Enabled by Azo and timsTOF Pro," Poster Presentation, ASMS Conference, Nov. 3, 2021.
Budnik et al. (Mar. 2016) Extracellular Vesicles Round off Communication in the Nervous System. Nat. Rev. Neurosci. 17 (3), 160-172.
Cai et al. (2014) Plasma Membrane Translocation of Trimerized MLKL Protein Is Required for TNF-Induced Necroptosis. Nat. Cell Biol. 16 (1), 55-65.
Cai et al. (2016) "MASH Suite Pro: A Comprehensive Software Tool for Top-Down Proteomics" Molecular & Cellular Proteomics 15.2, 703-714.
Cai et al. (2016) "Top-down Proteomics: Technology Advancements and Applications to Heart Diseases" Expert Rev Proteomics, 13(8), 717-730.
Chang et al. (2015) "New Mass-Spectrometry-Compatible Degradable Surfactant for Tissue Proteomics" Journal of Proteome Research, 14, 1587-1599.
Chen et al. (2013) Diverse Sequence Determinants Control Human and Mouse Receptor Interacting Protein 3 (RIP3) and Mixed Lineage Kinase Domain-like (MLKL) Interaction in Necroptotic Signaling. J. Biol. Chem. 288 (23), 16247-16261.
Chen et al. (Jan. 2018) "Top-Down Proteomics: Ready for Prime Time?" Anal. Chem. 90, 110-127.
Cho et al. (2009) Phosphorylation-Driven Assembly of the RIP1-RIP3 Complex Regulates Programmed Necrosis and Virus-Induced Inflammation. Cell 137 (6), 1112-1123.
Cravatt et al. (2007) "The biological impact of mass-spectormetry-based proteomics" Nature 450, 991-1001.
Douanne et al. (Aug. 2019) Pannexin-1 Limits the Production of Proinflammatory Cytokines during Necroptosis. EMBO Rep. 20 (10), e47840.
Douhal et al. (1995) "Femtosecond molecular dynamics of tautomerization in model base pairs" Nature, 378, 260-263.
Duan et al. (2009) "A Straightforward and Highly Efficient Precipitation/On-Pellet Digestion Procedure Coupled with a Long Gradient Nano-LC Separation and Orbitrap Mass Spectrometry for Label-Free Expression Profiling of the Swine Heart Mitochondrial Proteome" Journal of Proteome Research, 8, 2838-2850.
Dunkin et al. (1996) "Synthesis, characterization and applications of azo-containing photodestructible surfactants," Journal of the Chemical Society, Perkin Transactions 2, Issue 9, 1837-1842.
Durbin et al. (2014) "Autopilot: An Online Data Acquisition Control System for the Enhanced High-Throughput Characterization of Intact Proteins" Anal. Chem. 86, 1485-1492.
Ea et al. (2006) Activation of IKK by TNFα Requires Site-Specific Ubiquitination of RIP1 and Polyubiquitin Binding by NEMO. Mol. Cell 22 (2), 245-257.
Fan et al. (May 2019) Flotillin-Mediated Endocytosis and ALIX-Syntenin-1-Mediated Exocytosis Protect the Cell Membrane from Damage Caused by Necroptosis. Sci. Signal. 12 (583).
Ferguson et al. (2016) Exosomes as Therapeutics: The Implications of Molecular Composition and Exosomal Heterogeneity. J. Controlled Release. 228, 179-190.
Gao et al. (Apr. 2018) "Large Cardiac Muscle Patches Engineered From Human Induced-Pluripotent Stem Cell-Derived Cardiac Cells Improve Recovery From Myocardial Infarction in Swine" Circulation 137, 1717-1730.
Gong et al. (2017) ESCRT-III Acts Downstream of MLKL to Regulate Necroptotic Cell Death and Its Consequences. Cell 169 (2), 286-300.e16.
Goulet et al. (Jul. 2018) Exosomes Induce Fibroblast Differentiation into Cancer-Associated Fibroblasts through TGFB Signaling. Mol Cancer Res 16(7): 1196-1204 (accessed Jan. 31, 2021).
Gregorich et al. (2014) "Top-down proteomics in health and disease: Challenges and opportunities" Proteomics 14, 1195-1210.
Gupta et al. (Sep. 2022) "Necroptosis is associated with Rab27-independent expulsion of extracellular vesicles containing RIPK3 and MLKL," Journal of Extracellular Vesicles, 11, e12261. https://doi.org/10.1002/jev2.12261.

(56) References Cited

OTHER PUBLICATIONS

Harmati et al. (Oct. 2019) Small Extracellular Vesicles Convey the Stress-Induced Adaptive Responses of Melanoma Cells. Sci. Rep. 9 (1), 15329.
He et al. (2009) Receptor Interacting Protein Kinase-3 Determines Cellular Necrotic Response to TNF-α. Cell A86137 (6), 1100-1111.
Hildebrand et al. (2014) Activation of the Pseudokinase MLKL Unleashes the Four-Helix Bundle Domain to Induce Membrane Localization and Necroptotic Cell Death. Proc. Natl. Acad. Sci. 111 (42), 15072-15077.
Holliday et al. (Dec. 2019) Actin and Actin-Associated Proteins in Extracellular Vesicles Shed by Osteoclasts. Int. J. Mol. Sci. 21 (1), 158.
Hoover et al. (Jan. 2020) Evaluation of Nanoparticle Tracking Analysis for the Detection of Rod-Shaped Particles and Protein Aggregates. J. Pharm. Sci. 109, 452-463.
Hoshino et al. (2015) Tumour Exosome Integrins Determine Organotropic Metastasis. Nature. 527 (7578), 329-335.
Hsu et al. (1996) TNF-Dependent Recruitment of the Protein Kinase RIP to the TNF Receptor-1 Signaling Complex. Immunity 4 (4), 387-396.
Huynh et al. (2005) The Small Chemical Vacuolin-1 Alters the Morphology of Lysosomes without Inhibiting Ca2+-Regulated Exocytosis. EMBO Rep. 6 (9), 843-847.
Hwang et al. (2016) "A Family of Photolabile Nitroveratryl-Based Surfactants That Self-Assemble into Photodegradable Supramolecular Structures," Langmuir vol. 32, 3963-3969.
Hwang et al. (2016) "A Family of Photolabile Nitroveratryl-Based Surfactants That Self-Assemble into Photodegradable Supramolecular Structures," Langmuir, Supporting Information, issue 32, pp. S1-S13.
International Search Report and Written Opinion, dated Oct. 23, 2019, corresponding to International Application No. PCT/US2019/035447 (filed Jun. 4, 2019), from which the present application claims priority, 14 pp.
Kalluri et al. (Feb. 2020) The Biology, Function, and Biomedical Applications of Exosomes. Science 367 (6478).
Kanayama et al. (2004) TAB2 and TAB3 Activate the NF-KB Pathway through Binding to Polyubiquitin Chains. Mol. Cell 15 (4), 535-548.
Keerthikumar et al. (2016) ExoCarta: A Web-Based Compendium of Exosomal Cargo. J. Mol. Biol. 428 (4), 688-692.
Kim et al. (2006) "Photocleavage of o-nitrobenzyl ether derivatives for rapid biomedical release applications" Bioorg. Med. Chem. Lett. 16, 4007-4010.
Kim et al. (2014) "A draft map of the human proteome" Nature 509, 575-581.
Kim et al. (2017) Caspase-8 Controls the Secretion of Inflammatory Lysyl-TRNA Synthetase in Exosomes from Cancer Cells. J. Cell Biol. 216 (7), 2201-2216.
Kist et al. (Sep. 2020) Impaired RIPK1 Ubiquitination Sensitizes Mice to TNF Toxicity and Inflammatory Cell Death. Cell Death Differ. 28, 985-1000.
Knott et al. (Nov. 2020) Photocleavable Surfactant-Enabled Extracellular Matrix Proteomics. Anal. Chem. 92 (24), 15693-15698.
Kong et al. (2017) MSFragger: ultrafast and comprehensive peptide identification in mass spectrometry-based proteomics. Nat Methods 14, 513-520.
Kowal et al. (2016) Proteomic Comparison Defines Novel Markers to Characterize Heterogeneous Populations of Extracellular Vesicle Subtypes. PNAS. 113 (8), E968-E977.
Kugeratski et al. (Jun. 2021) Quantitative Proteomics Identifies the Core Proteome of Exosomes with Syntenin-1 as the Highest Abundant Protein and a Putative Universal Biomarker. Nat. Cell Biol. 23 (6), 631-641.
Loo et al. (1994) "Surfactant effects on protein structure examined by electrospray ionization mass spectrometry" Protein Science 3, 1975-1983.
Loughrey et al. (2016) Using the NanoDrop One to Quantify Protein and Peptide Preparations at 205 nm. Thermo Fisher Scientific.

Maclennan et al. (2003) "Phospholamban: A Crucial Regulator of Cardiac Contractility" Nature 4, 566-577.
Medina et al. (Apr. 2020) Metabolites released from apoptotic cells act as tissue messengers. Nature 580, 130-135. (accessed Jan. 31, 2021).
Meier et al. (Dec. 2018) Online Parallel Accumulation-Serial Fragmentation (PASEF) with a Novel Trapped Ion Mobility Mass Spectrometer. Mol. Cell. Proteomics. 17 (12), 2534-2545.
Melby et al. (Jun. 2021) Novel Strategies to Address the Challenges in Top-Down Proteomics. J. Am. Soc. Mass Spectrom 32 (6), 1278-1294.
Mezger et al. (1996) "Light decomposable emulsifiers: application of alkyl-substituted aromatic azosulfonates in emulsion polymerization" Progress in Organic Coatings 29, 147-157.
Müller et al. (2017) Systematic Evaluation of Protein Reduction and Alkylation Reveals Massive Unspecific Side Effects by Iodine-Containing Reagents. Molecular & cellular proteomics : Molecular & Cellular Proteomics 16 (7), 1173-1187.
Orozco et al. (2014) RIPK1 Both Positively and Negatively Regulates RIPK3 Oligomerization and Necroptosis. Cell Death Differ. 21 (10), 1511-1521.
Ostrowski (2010) Rab27a and Rab27b Control Different Steps of the Exosome Secretion Pathway. Nat. Cell Biol. 12 (1), 19-30.
Pathan et al. (Jan. 2019) Vesiclepedia 2019: A Compendium of RNA, Proteins, Lipids and Metabolites in Extracellular Vesicles. Nucleic Acids Res. 2019, 47 (D1), D516-D519.
Pavlyukov et al. (Jul. 2018) Apoptotic Cell-Derived Extracellular Vesicles Promote Malignancy of Glioblastoma via Intercellular Transfer of Splicing Factors. Cancer Cell. 34 (1), 119-135.e10.
Prive et al. (2007) "Detergents for the stabilization and crystallization of membrane proteins" Methods 41, 388-397.
Reddy et al. (2001) Plasma Membrane Repair Is Mediated by Ca2+-Regulated Exocytosis of Lysosomes. Cell 106 (2), 157-169.
Rock (2008) The Inflammatory Response to Cell Death. Annu. Rev. Pathol. 3, 99-126.
Rontogianni et al. (Sep. 2019) Proteomic Profiling of Extracellular Vesicles Allows for Human Breast Cancer Subtyping. Commun. Biol. 2 (1), 325.
Sahoo et al. (Apr. 2021) Therapeutic and Diagnostic Translation of Extracellular Vesicles in Cardiovascular Diseases. Circulation 143 (14), 1426-1449.
Samson et al. (Jun. 2020) MLKL Trafficking and Accumulation at the Plasma Membrane Control the Kinetics and Threshold for Necroptosis. Nat. Commun. 11 (1), 3151.
Schey et al. (2015) Proteomics Characterization of Exosome Cargo. Methods 87, 75-82.
Sedger et al. (2014) TNF and TNF-Receptors: From Mediators of Cell Death and Inflammation to Therapeutic Giants-Past, Present and Future. Cytokine Growth Factor Rev. 25 (4), 453-472.
Seo et al. (2016) CHIP Controls Necroptosis through Ubiquitylation- and Lysosome-Dependent Degradation of RIPK3. Nat. Cell Biol. 18 (3), 291-302.
Shlomovitz et al. (Nov. 2021) Proteomic analysis of necroptotic extracellular vesicles. Cell Death and Disease 12: 1059 (accessed Jan. 31, 2021).
Simpson (2009) Exosomes: Proteomic Insights and Diagnostic Potential. Expert Rev. Proteomics. 6 (3), 267-283.
Siuti et al. (2007) "Decoding protein modifications using top-down mass spectrometry" Nature Methods, 4(10), 817-821.
Smith et al. (2013) "Proteoform: a single term describing protein complexity" Nature Methods 10(3), 186-187.
Smith et al. (2018) "Proteoforms as the next proteomics currency" Science 359(6380), 1106-1108.
Sokolova et al. (2011) Characterisation of Exosomes Derived from Human Cells by Nanoparticle Tracking Analysis and Scanning Electron Microscopy. Colloids and Surfaces B: Biointerfaces. 87 (1), 146-150.
Speers et al. (2007) "Proteomics of Integral Membrane Proteomics— Theory and Application" Chem. Rev. 107, 3687-3714.
Su et al. (2014) A Plug Release Mechanism for Membrane Permeation by MLKL. Structure 2014, 22 (10), 1489-1500.

(56) References Cited

OTHER PUBLICATIONS

Sun et al. (2002) Identification of a Novel Homotypic Interaction Motif Required for the Phosphorylation of Receptor-Interacting Protein (RIP) by RIP3. J. Biol. Chem. 277 (11), P9505-9511.

Sung et al. (2015) Directional Cell Movement through Tissues Is Controlled by Exosome Secretion. Nat. Comm. 6 (1), 7164.

Szklarczyk et al. (Nov. 2018) String V11: Protein-Protein Association Networks with Increased Coverage, Supporting Functional Discovery in Genome-Wide Experimental Datasets. Nucleic Acids Res. 47 (D1), D607-D613.

Tanzer et al. (Jan. 2020) Quantitative and Dynamic Catalogs of Proteins Released during Apoptotic and Necroptotic Cell Death. Cell Rep. 30 (4), 1260-1270.e5.

Tehrani-Bagha et al. (2007) "Cleavable Surfactants" Current Opinion in Colloid & Interface Science 12, 81-91.

Thery et al. (Dec. 2018) Minimal Information for Studies of Extracellular Vesicles 2018 (MISEV2018): A Position Statement of the International Society for Extracellular Vesicles and Update of the MISEV2014 Guidelines. J. Extracell. Vesicles 7 (1), 1535750.

Tkach et al. (2016) Communication by Extracellular Vesicles: Where We Are and Where We Need to Go. Cell 164 (6), 1226-1232.

Trairak et al. (2004) Identification and Proteomic Profiling of Exosomes in Human Urine. PNAS 101 (36), 13368-13373.

Waas et al. (2014) Combine and Conquer: Surfactants, Solvents, and Chaotropes for Robust Mass Spectrometry Based Analyses of Membrane Proteins. Analytical Chemistry 86 (3), 1551-1559.

Walbrecq et al. (Jul. 2020) Distinct Cargos of Small Extracellular Vesicles Derived from Hypoxic Cells and Their Effect on Cancer Cells. Int. J. Mol. Sci. 21 (14), 5071.

Walpole et al. (2015) "Conservation of Complete Trimethylation of Lysine-43 in the Rotor Ring of c-Subunits of Metazoan Adenosine Triphosphate (ATP) Synthases" Molecular & Cellular Proteomics 14(4), 828-840.

Whitelegge (2013) "Integral Membrane Proteins and Bilayer Proteomics" Anal. Chem. 85, 2558-2568.

Whitelegge et al. (1999) "Toward the bilayer proteome, electrospray ionization- mass spectrometry of large, intact transmembrane proteins" Proc. Natl. Acad. Sci. 96, 10695-10698.

Wientzek et al. (1991) "Isolation and Characterization of Purified Sarcoplasmic Reticulum Membranes from Isolated Adult Rat Ventricular Myocytes" J Mol Cell Cardiol 23, 1149-1163.

Wiesniewski et al. (2009) "Universal Sample preparation method for proteome analysis" Nature Methods 6(5), 359-363.

Wu et al. (2003) "The application of mass spectrometry to membrane proteomics" Nature Biotechnology 21, 262-267.

Wu et al. (2013) MIkl Knockout Mice Demonstrate the Indispensable Role of MIkl in Necroptosis. Cell Res. 23 (8), 994-1006.

Yan et al. (2013) "Photoisomerization Quantum Yield of Azobenzene-Modified DNA Depends on Local Sequence" J. Am. Chem. Soc. 135, 8382-8387.

Yergey (1983) "A general approach to calculating isotopic distributions for mass spectrometry" International Journal of Mass Spectrometry and Ion Physics, 52, 337-349.

Yoon et al. (2017) MLKL, the Protein That Mediates Necroptosis, Also Regulates Endosomal Trafficking and Extracellular Vesicle Generation. Immunity 47 (1), 51-65.e7.

Yu et al. (2003) "Enzyme-Friendly, Mass Spectrometry-Compatible Surfactant for In-Solution Enzymatic Digestion of Proteins" Anal. Chem. 75, 6023-6028.

Yu et al. (Apr. 2021) IonQuant Enables Accurate and Sensitive Label-Free Quantification With FDR-Controlled Match-Between-Runs. Molecular & Cellular Proteomics 20: 100077.

Yu et al. (Sep. 2020) Fast Quantitative Analysis of TimsTOF PASEF Data with MSFragger and IonQuant. Mol. Cell. Proteomics. 2020, 19 (9), 1575-1585.

Zargarian et al. (2017) Phosphatidylserine Externalization, "Necroptotic Bodies" Release, and Phagocytosis during Necroptosis. PLOS Biol. 15 (6), e2002711.

Zhang et al. (2009) RIP3, an Energy Metabolism Regulator That Switches TNF- Induced Cell Death from Apoptosis to Necrosis. Science 325 (5938), 332-336.

Zhang et al. (Sep. 2019) Ubiquitination of RIPK1 Suppresses Programmed Cell Death by Regulating RIPK1 Kinase Activation during Embryogenesis. Nat. Commun., 10 (1), 4158.

Zhou et al. (2015) "Palmitoyl acyltransferase Aph2 in cardiac function and the development of cardiomyopathy" PNAS 112(51), 15666-15671.

Zulkefli et al. (Jul. 2019) A Role for Rab11 in the Homeostasis of the Endosome-Lysosomal Pathway. Exp. Cell Res. 380 (1), 55-68.

U.S. Appl. No. 17/978,793, filed Nov. 1, 2022.

U.S. Appl. No. 16/972,881, filed Dec. 7, 2020.

\* cited by examiner

| Category | Protein Name | Gene Name |
| --- | --- | --- |
| Collagens | Collagen alpha-1(I) chain | CO1A1 |
| Collagens | Collagen alpha-1(VI) chain | COL6A1 |
| Collagens | Collagen alpha-1(VII) chain | CO7A1 |
| Collagens | Collagen alpha-1(XII) chain | COL12A1 |
| Collagens | Collagen alpha-1(XIII) chain | COL13A1 |
| Collagens | Collagen alpha-1(XIV) chain | COL14A1 |
| Collagens | Collagen alpha-1(XIV) chain | K3W4R4 |
| Collagens | Collagen alpha-1(XV) chain | COFA1 |
| Collagens | Collagen alpha-1(XV) chain | A2AJY5 |
| Collagens | Collagen alpha-1(XV) chain | A2AJY7 |
| Collagens | Collagen alpha-2(I) chain | CO1A2 |
| Collagens | Collagen alpha-2(IV) chain | CO4A2 |
| Collagens | Collagen alpha-2(VI) chain | CO6A2 |
| Collagens | Collagen, type VI, alpha 3 (X2) | COL6A3 |
| Glycoproteins | Adipocyte enhancer-binding protein 1 | AEBP1 |
| Glycoproteins | EMILIN-1 | EMIL1 |
| Glycoproteins | Fibrillin-1 | FBN1 |
| Glycoproteins | Fibrillin-1 | FBN1 |
| Glycoproteins | Fibrinogen beta chain | FIBB |
| Glycoproteins | Fibrinogen gamma chain | FGG |
| Glycoproteins | Fibronectin | FINC |
| Glycoproteins | Fibulin-5 | FBLN5 |
| Glycoproteins | Lamin-B1 | LMNB1 |
| Glycoproteins | Lamin-B2 | LMNB2 |
| Glycoproteins | Laminin subunit alpha-5 | LAMA5 |
| Glycoproteins | Laminin subunit gamma-1 | LAMC1 |
| Glycoproteins | Leucine-rich HEV glycoprotein | LRG1 |
| Glycoproteins | Nidogen-1 | NID1 |
| Glycoproteins | Periostin | POSTN |
| Glycoproteins | Tenascin | TENA |
| Glycoproteins | Thrombospondin 1 | THBS1 |
| Glycoproteins | von Willebrand factor A domain-containing protein 1 | VWA1A |
| Glycoproteins | von Willebrand factor A domain-containing protein 3A | VWA3A |
| Glycoproteins | von Willebrand factor A domain-containing protein 5A | VWA5A |
| Glycoproteins | Extracellular matrix protein FRAS1 | FRAS1 |
| Glycoproteins | Vitronectin | VTNC |
| Glycoproteins | Insulin-like growth factor-binding protein complex acid labile subunit | GFALS |
| Glycoproteins | Nidogen-2 | NID2 |
| Glycoproteins | DEAD (Asp-Glu-Ala-Asp) box polypeptide 5 | DDX5 |
| Glycoproteins | Thrombospondin 1 | THBS1 |
| Glycoproteins | Papilin | PAPLN |
| Glycoproteins | Microfibrillar-associated protein 1A | MFAP1 |
| Glycoproteins | Fibrinogen alpha chain | FGA |
| Glycoproteins | transforming growth factor, beta induced | TGFBI |
| Proteoglycans | Asporin | ASPN |
| Proteoglycans | Basement membrane-specific heparan sulfate proteoglycan core protein | HSPG2 |
| Proteoglycans | Biglycan | PGS1 |
| Proteoglycans | Decorin | PGS2 |
| Proteoglycans | Lumican | LUM |
| Proteoglycans | Prolargin | PRELP |
| Proteoglycans | Mimecan | OGN |
| Affiliated | Annexin A1 | ANXA1 |
| Affiliated | Annexin A2 | ANXA2 |
| Affiliated | Annexin | F8WIT2 |
| Affiliated | Complement component 1 Q subcomponent-binding protein | C1QBP |
| Affiliated | Annexin A5 | ANXA5 |
| Affiliated | Annexin A4 | ANXA4 |
| Affiliated | Annexin A11 | ANXA11 |
| Affiliated | Annexin A3 | ANXA3 |
| Regulators | Protein-glutamine gamma glutamyltransferase | TGM2 |
| Regulators | Serpin B13 | SPB13 |
| Regulators | Serpin H1 | SERPINH1 |
| Regulators | Pigment epithelium-derived factor | SERPINF1 |
| Regulators | Alpha-2-macroglobulin | A2M |
| Regulators | kininogen 2 | KNG2 |
| Regulators | Serpin B6 | SERPINB6B |
| Regulators | Cathepsin D | CTSD |
| Regulators | Serpin B6 | SERPINB6 |
| Secreted Factors | Protein S100-A6 | S100A6 |
| Secreted Factors | Protein S100-A8 | S100A8 |
| Secreted Factors | Protein S100-A1 | S100A9 |

Fig. 40

PHOTO-CLEAVABLE SURFACTANTS

CROSS-REFERENCE TO RELATED APPLICATIONS

This application is a divisional of U.S. application Ser. No. 16/972,881, filed Dec. 7, 2020, which is a U.S. National Stage Application filed under 35 U.S.C. § 371 of International Application No. PCT/US2019/035447, filed on Jun. 4, 2019, which claims priority from U.S. Provisional Patent Application No. 62/682,027, filed Jun. 7, 2018, and U.S. Provisional Patent Application No. 62/810,744, filed Feb. 26, 2019, all which are incorporated by reference herein to the extent that there is no inconsistency with the present disclosure.

STATEMENT REGARDING FEDERALLY SPONSORED RESEARCH OR DEVELOPMENT

This invention was made with government support under GM117058 awarded by the National Institutes of Health. The government has certain rights in the invention.

BACKGROUND OF THE INVENTION

Unlike the genome, the proteome is dynamic and highly complex mainly due to alternative splicing and post-translational modifications (PTMs) which modulate activity and function of proteins (Aebersold et al., 2016, Nature, 537: 347; Altelaar et al., 2012, Nature Reviews Genetics, 14:35; and Cai et al., 2016, Expert Review of Proteomics, 13:717-730). In the post-genomics era, a comprehensive analysis of "proteoforms" that arise from genetic variations and PTMs, is essential for understanding biological systems at a functional level toward deciphering disease mechanisms as well as identifying key diagnostic markers and new therapeutic targets (Smith et al., 2013, Nat Methods, 10:186-187; Aebersold et al., 2018, Nature Chemical Biology, 14:206; and Smith et al., 2018, Science, 359:1106-1107). Conventional "bottom-up" proteomics is invaluable in the identification and quantification of the proteome as well as the elucidation of protein-protein interaction and signaling networks (Aebersold et al., 2016, Nature, 537:347; and Cravatt et al., 2007, Nature, 450:991). Bottom-up proteomics analyzes peptides from protein digests but does not directly identify proteoforms. Instead, the presence of proteins is inferred from identification of peptides. As a result, bottom-up proteomics may be suboptimal for characterizing PTMs and sequence variants (Aebersold et al., 2018, Nature Chemical Biology, 14:206; and Smith et al., 2018, Science, 359:1106-1107). In contrast, top-down mass spectrometry (MS)-based proteomics, which is based on analysis of intact proteins, is arguably the most powerful method to comprehensively characterize proteoforms to decipher the PTM codes together with sequence variations (Cai et al., 2016, Expert Review of Proteomics, 13:717-730; Gregorich et al., 2014, Proteomics, 14:1195-1210; and Siuti et al., 2007, Nature Methods, 4:817-821). However, despite its promising outlook, top-down proteomics still faces significant challenges (Gregorich et al., 2014, Proteomics, 14:1195-1210; and Chen et al., 2018, Analytical Chemistry, 90:110-127).

Protein solubility remains a major challenge in bottom-up and top-down proteomics. To effectively extract proteins from cells/tissues, surfactants (also known as detergents) are commonly included in the extraction buffer (Wisniewski et al., 2009, Nat Methods, 6:359-362). In particular, membrane proteins, which comprise approximately one-third of the proteome and play an important role in many essential cellular functions and account for a significant proportion of drug targets, are not soluble in aqueous solutions without the addition of surfactants because of their hydrophobic nature (Whitelegge et al., 2013, Anal Chem, 85:2558-2568; Wu et al., 2003, Nat Biotechnol, 21:262-267; Whitelegge et al., 1999, Proc Natl Acad Sci USA, 96:10695-10698; and Barrera et al., 2011, Annu Rev Biochem, 80:247-271).

Unfortunately, conventional surfactants such as sodium dodecyl sulfate (SDS) are not compatible with MS because they greatly suppress the MS signal of proteins (Wisniewski et al., 2009, Nat Methods, 6:359-362; Speers et al., 2007, Chem Rev, 107:3687-3714; and Loo et al., 1994, Protein Sci, 3:1975-1983). Therefore, an extra step is needed to remove the surfactant prior to MS analysis, which is not only time consuming, but also results in protein loss and degradation (Wisniewski et al., 2009, Nat Methods, 6:359-362; Duan et al., 2009, J Proteome Res, 8:2838-2850; Bereman et al., 2011, Proteomics, 11:2931-2935; Yu et al., 2003, Anal Chem, 75:6023-6028; and Botelho et al., 2010, J Proteome Res, 9:2863-2870). To address these problems, it is critical to develop surfactants compatible with both top-down and bottom-up MS with the ability to effectively solubilize proteins, where the surfactant can quickly degrade into innocuous non-surfactant byproducts prior to MS analysis.

In the past years, major efforts have been dedicated in developing acid-labile surfactants, which contain an acid-labile functional group between the hydrophilic head and hydrophobic tail and thus can be degraded after incubation with acid (Chang et al., 2015, Journal of Proteome Research, 14:1587-1599). Although various acid-labile surfactants such as RapiGest™ (RG, Waters), ProteaseMax™ (PM, Promega) and the recently developed MScompatible slowly-degradable surfactant (MasDeS) have been demonstrated as being effective for bottom-up proteomics, none of them have demonstrated direct compatibility with intact protein MS for top-down proteomics due to the significant signal suppression during the ionization process. Additionally, these commonly employed acid-labile surfactants require highly acidic conditions post-digestion for degradation and often require an offline clean-up step, making it difficult for fast automation. Moreover, the strong acidic degradation may cause loss of labile post-translational modifications that are not stable in acidic conditions (Zhang et al., 2015, Molecular & cellular proteomics: MCP, 14:2441-2453). In addition, some of these acid-labile surfactants generate amine products after acid degradation that interfere with the isobaric amine-reactive tandem mass tag labeling reagents such as TMT and iTRAQ.

Therefore, an ideal MS-compatible non-acid labile surfactant that can solubilize and denature proteins and other compounds without time-consuming clean-up or desalting requirements, and thus is compatible with both top-down and bottom-up proteomics, is particularly attractive in streamlining sample preparation in proteomics. Preferably, such surfactants can be also utilized as surfactants to solubilize compounds in electrophoresis.

SUMMARY OF THE INVENTION

Bottom-up proteomics (BUP) and top-down proteomics (TDP) are powerful methods for the comprehensive characterization of PTMs, which regulate protein activity, interactions, and function. Despite their promising outlook, BUP and TDP still face many challenges such as protein solubility, particularly for membrane proteins. Unfortunately, traditional surfactants like sodium dodecyl sulfate (SDS) are known to suppress electrospray ionization (ESI) of proteins, making them incompatible with mass spectrometry (MS) analysis. The present invention describes rapidly-degradable, anionic surfactants capable of extracting a high concentration of intact protein while also being amenable to downstream MS and tandem MS (MS/MS) analysis. Also described herein is a generalizable, surfactant-aided liquid chromatography (LC)-MS/MS method able to comprehensively characterize the PTMs of important membrane proteins.

Distinct from the previous approaches of making acid-labile surfactants, the present invention provides photo-cleavable surfactants which are stable under acidic conditions, but can be cleaved and degraded upon irradiation with light, especially ultraviolet (UV) radiation, before MS analysis (FIG. 1, panel a). Therefore, these surfactants will not significantly interfere with MS detection of proteins. In an aspect of the invention, a library of photolabile surfactants have been designed and synthesized by inserting a photo-cleavable moiety in between the hydrophilic head and hydrophobic tail. Degradation via a photochemical reaction has the advantage of being simple, clean (no additional reagents typically need to be added), fast, and can be easily controlled by turning on and off a suitable light source (such as a UV lamp).

In an embodiment, the present invention provides photo-labile surfactants by inserting a photo-cleavable moiety in between the hydrophilic head and hydrophobic tail. In a further embodiment, O-nitrobenzyl (ONB), O-nitroveratryl (ONV), and azobenzene (AZO) groups are chosen as the photo-cleavable moieties.

In an embodiment, the present invention provides a photo-cleavable anionic surfactant, 4-hexylphenylazo-sulfonate (also referred to herein as "Azo"), which can be rapidly degraded upon UV irradiation. Azo can effectively solubilize proteins with performance comparable to sodium dodecyl sulfate (SDS) and is MS-compatible. For example, after solubilization, a sample to be analyzed using mass spectrometry is exposed to UV radiation, which decomposes the Azo prior to entering the mass spectrometer. Azo-aided top-down proteomics has allowed the detection of 100-fold more unique proteoforms as compared to controls and enabled the solubilization of membrane proteins for comprehensive characterization of post-translational modifications. It is believed that the surfactants of the present invention are the first MS-compatible cleavable surfactants developed for top-down proteomics.

In an embodiment, the present invention provides a photo-cleavable surfactant comprising: a) hydrophilic head, b) a hydrophobic tail, and c) a photo-cleavable moiety covalently linking the hydrophilic head and hydrophobic tail, where the photo-cleavable moiety is able to release the hydrophilic head, release the hydrophobic tail, and/or break apart upon exposure to electromagnetic radiation. Preferably, the electromagnetic radiation is ultraviolet (UV) light. Preferably, the photo-cleavable moiety releases the hydrophilic head, releases the hydrophobic tail, or degrades under light having a wavelength between 150-450 nm, between 200-400 nm, between 250-350 nm, or between 280-300 nm.

Preferably, the photo-cleavable surfactant is stable at any pH, but is especially functional at a pH range that is not operable for other existing surfactants, such as acid labile surfactants. In an embodiment, the photo-cleavable surfactant is able to remain stable at a pH of 4 or lower, at a pH of 3 or lower, at a pH of or lower 2, or at a pH of 1 or lower. Conventional acid labile surfactants typically hydrolyze at a pH of approximately 2-3. In an embodiment, the photo-cleavable surfactants of the present invention, such as the Azo surfactant, are stable at any pH and photo degradation is optimal at low pH (~2) with an organic solvent. Under aqueous conditions, pH has little or no effect on the surfactant. This makes surfactants of the present invention well suited for both offline and online LC/MS analysis of proteins, which commonly utilize acid in the electrospray solution and mobile phases. Moreover, many proteins need to be extracted under acidic conditions, which renders conventional rapidly acid-labile surfactants ineffective.

In an embodiment, the photo-cleavable surfactant has the formula:

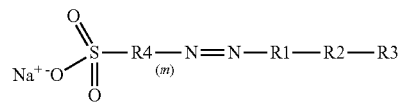

wherein,
R1 is a substituted or unsubstituted aryl group having from 4 to 18 carbon atoms, preferably 5 to 7 carbon atoms;
R2 is a substituted or unsubstituted alkylene or alkenylene group having from 2 to 18 carbon atoms, preferably 4 to 8 carbon atoms;
R3 is a substituted or unsubstituted alkyl, alkenyl, or aryl group having from 1 to 6 carbon atoms, preferably 1 to 3 carbon atoms;
R4 is a substituted or unsubstituted alkylene or alkenylene group having from 1 to 5 carbon atoms; and
m is an integer selected from 1 and 0.

In an embodiment, the photo-cleavable surfactant has the formula:

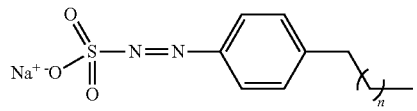

where n is an integer selected from 2 to 30. Preferably, n is an integer selected from 2 to 20, an integer selected from 4 to 15, or an integer selected from 6 to 12. Preferably, n is 6, 8, 10 or 12. In an embodiment, the photo-cleavable surfactant is sodium 4-hexylphenylazosulfonate.

In an embodiment, the photo-cleavable surfactant has the formula:

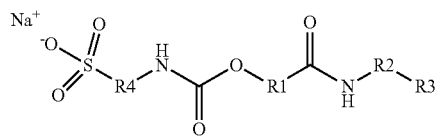

wherein
R1 is a substituted or unsubstituted aryl group having from 6 to 18 carbon atoms, preferably 5 to 8 carbon atoms;
R2 is a substituted or unsubstituted alkylene or alkenylene group having from 2 to 18 carbon atoms, preferably 2 to 8 carbon atoms;
R3 is a substituted or unsubstituted alkyl, alkenyl, or aryl group having from 1 to 6 carbon atoms, preferably 1 to 3 carbon atoms; and R4 is a substituted or unsubstituted alkylene or alkenylene group having from 1 to 8 carbon atoms, preferably 5 to 8 carbon atoms.

In an embodiment, the photo-cleavable surfactant has the formula:

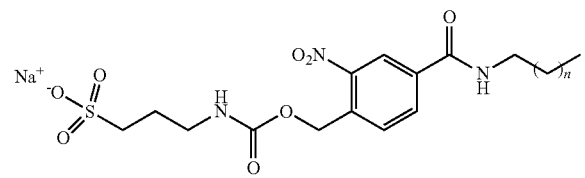

where n is an integer selected from 2 to 30. Preferably, n is an integer selected from 2 to 20, an integer selected from 4 to 15, or an integer selected from 4 to 12. Preferably, n is 4, 6 or 10.

In an embodiment, the photo-cleavable surfactant has the formula:

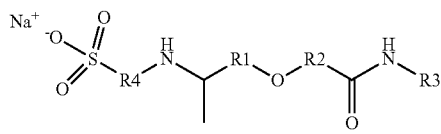

wherein
R1 is a substituted or unsubstituted aryl group having from 6 to 18 carbon atoms, preferably 5 to 8 carbon atoms;
R2 is a substituted or unsubstituted alkylene or alkenylene group having from 2 to 18 carbon atoms, preferably 2 to 8 carbon atoms;
R3 is a substituted or unsubstituted alkyl, alkenyl, or aryl group having from 1 to 18 carbon atoms, preferably 1 to 3 carbon atoms; and
R4 is a substituted or unsubstituted alkylene or alkenylene group having from 1 to 8 carbon atoms, preferably 5 to 8 carbon atoms.

In an embodiment, the photo-cleavable surfactant has the formula:

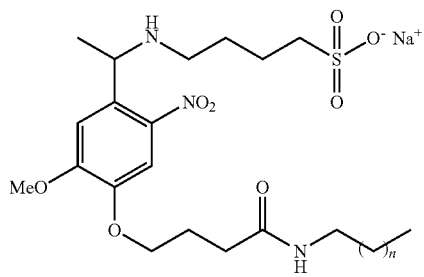

where n is an integer selected from 2 to 30. Preferably, n is an integer selected from 2 to 20, an integer selected from 4 to 15, or an integer selected from 6 to 12. Preferably, n is 6, 8 or 10.

In an embodiment, the photo-cleavable surfactant is stable at a pH of 7 or greater, a pH of 6 or greater, a pH of 5 or greater, a pH of 4 or greater, or a pH of 3 or greater.

In an embodiment, the present invention provides a method of solubilizing a compound comprising the steps of: a) mixing the compound with a photo-cleavable surfactant in a solution until the compound is dissolved in the solution; and b) exposing the solution containing the photo-cleavable surfactant and dissolved compound to electromagnetic radiation, thereby cleaving the photo-cleavable moiety, wherein the photo-cleavable surfactant comprises: i) hydrophilic head, ii) a hydrophobic tail, and iii) a photo-cleavable moiety covalently linking the hydrophilic head and hydrophobic tail. Preferably, the compound is a protein or a polypeptide. In an embodiment, the compound is a membrane protein, including but not limited to receptor proteins (e.g., beta-adrenergic receptors) or ion channel proteins. In an embodiment, the compound is an extra cellular matrix protein (ECM).

Optionally, the method further comprises performing mass spectrometry (MS) analysis on a portion of the irradiated solution containing the compound, such as part of an online liquid chromatography-mass spectrometry (LC/MS) experiment. In an embodiment, after dissolving the compound in the solution containing the photo-cleavable surfactant, a chromatography step is performed on the solution in order to purify or separate the components in the solution. The portion or fraction of the solution which contains the dissolved compound is exposed to the electromagnetic radiation before injecting or spraying the dissolved compound into the mass spectrometer. Optionally, the photodegradation occurs after chromatography separation of proteins before spraying into the mass spectrometer, as the experiments happen in a real time.

Alternatively, photodegredation of the photo-cleavable surfactant occurs in the mass spectrometer during ultraviolet photo-dissociation (UVPD). UVPD is becoming a powerful tandem mass spectrometry (MS/MS) tool for comprehensive analysis of proteins (Brodbelt et al., 2014, Chem. Soc. Rev., 43 (8): 2757-2783), and is compatible with current mass spectrometers. For example, the Thermo Orbitrap Lumos is a popular proteomic instrument that can be currently equipped with a 213 nm UV laser.

Preferably, the solution containing the photo-cleavable surfactant and dissolved compound is exposed to ultraviolet (UV) light. Preferably, the light has a wavelength between 150-450 nm, between 200-400 nm, between 250-350 nm, or between 280-300 nm. In an embodiment, the solution containing the photo-cleavable surfactant and dissolved compound is exposed to the electromagnetic radiation for a time period between 10 and 500 seconds, preferably between 15 and 400 seconds, between 20 and 300 seconds, between 25 and 200 seconds, or between 30 and 150 seconds.

The solution comprises an organic solvent, aqueous solvent, or combinations thereof. Optionally, the solution also comprises 10% or less of an acid or reducing agent. Alternatively, the solution does not contain any additional acids or reducing agents. The solution also comprises 1% or less of the photo-cleavable surfactant, preferably 0.5% or less of the photo-cleavable surfactant, preferably 0.1% or less of the photo-cleavable surfactant. In an embodiment, the solution comprises 70% or more of an organic solution, 5% or less of an acid, and 0.1% or less of the photo-cleavable surfactant.

The optimal formulation depends on the proteins and protein families being solubilized. In an embodiment, the solution comprises 20-80% organic solvent, 0.1-5% acid, and 0.1-1% surfactant. Preferred organic solvents include, but are not limited to, acetonitrile, methanol, and isopropanol (IPA). The solution may also comprise tri (2-carboxyethyl) phosphine hydrochloride (TCEP) so as to reduce or minimize oxidative modification of proteins during analysis. Optionally an acid, such as formic acid, is added to speed up degradation of the photo-cleavable moiety. In an embodiment, the solution comprises at least 30% organic solvent (such as IPA) in order to avoid salt formation. In an embodiment, the solution comprises 40% IPA or (IPA: ACN 1:1), 1% formic acid, 100 mM TCEP (avoid oxidation), and 0.1-0.2% of the photo-cleavable surfactant.

In an embodiment, the photo-cleavable surfactant of the method a formula selected from the following:

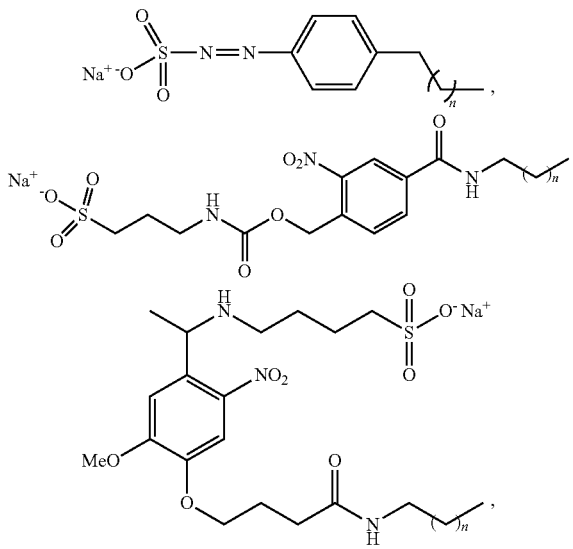

and combinations thereof, where n is an integer selected from 2 to 30. Preferably, n is an integer selected from 2 to 20, an integer selected from 4 to 15, or an integer selected from 4 to 12. Preferably, n is 4, 6, 8 or 10. Preferably, the photo-cleavable surfactant is sodium 4-hexylphenylazosulfonate.

Additional advantages of certain embodiments of the present invention include: (1) fast and scalable surfactant synthesis (two-step synthesis with recrystallization for purification); (2) rapid surfactant degradation at ambient temperature with UV irradiation (30-150 s with visible color change); (3) operating conditions that allow for retained protein solubility post-degradation; (4) compatibility with direct ESI-MS and LC-MS analysis after photo degradation; (5) extraction of a high concentration of proteins with performance comparable to SDS; and (6) the ability to solubilize proteins that are typically difficult to solubilize, notably membrane proteins, enabling their characterization by mass spectrometry with minimal additional purification steps.

While aspects of the present invention provide improvements over surfactants and methods used in conjunction with top-down proteomics, it should be noted the present invention is useful for bottom-up proteomics as well. In bottom-up proteomics, proteins are solubilized and digested into smaller polypeptides, and the mixtures of polypetides are analyzed together. The present methods and surfactants can be utilized to improve solubility of proteins and facilitate the extraction of proteins from tissues, cells etc. for both top-down proteomics and bottom-up proteomics.

In an embodiment, the photo-cleavable surfactants of the present invention are provided in a method for analyzing a polypeptide comprising the steps of:
 a) mixing the polypeptide with a photo-cleavable surfactant in a solution until the compound is dissolved in the solution, wherein the polypeptide has a molecular weight of 100 daltons or more, and wherein the photo-cleavable surfactant comprises: i) a hydrophilic head, ii) a hydrophobic tail, and iii) a photo-cleavable moiety covalently linking the hydrophilic head and hydrophobic tail;
 b) exposing the solution containing the photo-cleavable surfactant and dissolved compound to electromagnetic radiation, thereby decomposing the photo-cleavable moiety; and
 c) performing mass spectrometry (MS) analysis on a portion of the irradiated solution containing the polypeptide.

In an embodiment, the photo-cleavable surfactants of the present invention are provided in a method for analyzing a polypeptide comprising the steps of:
 a) fragmenting or digesting the polypeptide into a plurality of fragments;
 b) mixing the plurality of fragments with a photo-cleavable surfactant in a solution until a portion of the plurality off fragments is dissolved in the solution, wherein the photo-cleavable surfactant comprises: i) a hydrophilic head, ii) a hydrophobic tail, and iii) a photo-cleavable moiety covalently linking the hydrophilic head and hydrophobic tail;
 c) exposing the solution containing the photo-cleavable surfactant and dissolved fragments to electromagnetic radiation, thereby decomposing the photo-cleavable moiety; and
 d) performing mass spectrometry (MS) analysis on a portion of the irradiated solution containing the dissolved fragments.

These analytical methods optionally further comprise separating components in the solution using a chromatography step and exposing the solution containing the dissolved fragments to electromagnetic radiation before injecting the dissolved fragments into a mass spectrometer. In further embodiments, the solution containing the dissolved fragments is exposed to electromagnetic radiation within a mass spectrometer during ultraviolet photo-dissociation (UVPD).

Additionally, the surfactants and methods described herein can be utilized to improve solubility of compounds in a wide range of biological and chemical applications, including applications that typically involve denaturing surfactants. For example, in an embodiment of the invention, the present surfactants are suitable as general alternatives to sodium dodecyl sulfate (SDS).

In an embodiment, the photo-cleavable surfactants of the present invention are provided in a method for separating components in a sample solution using electrophoresis, the method comprising the steps of:
 a) providing a porous gel having a first end and a second end and having one or more liquid buffers, wherein the one or more liquid buffers are able to conduct an electric current across the gel;
 b) disposing the sample solution in the first end of the gel, wherein the sample solution further comprises a photo-cleavable surfactant comprising: i) a hydrophilic head, ii) a hydrophobic tail, and iii) a photo-cleavable moiety covalently linking the hydrophilic head and hydrophobic tail, and wherein the sample solution and the one or buffers do not comprise a significant amount of sodium dodecyl sulfate (SDS) or urea; and
 c) applying an electric current across the first and second end of the porous gel, wherein the components in the sample solution will move from the first end of the porous gel toward the second end of the porous gel.

The use of one or more photo-cleavable surfactants of the present invention as substitute for SDS is particularly useful when the sample solution comprises one or more polypeptides. Preferably, the porous gel is a polyacrylamide gel and the sample solution further comprises a tracking dye or stain. The electrophoresis process may further have less than 0.1% sodium dodecyl sulfate (SDS) or urea in the sample solution and the one or more buffers, preferably no sodium dodecyl sulfate (SDS) or urea.

BRIEF DESCRIPTION OF THE DRAWINGS

FIGS. 8-1H-NMR spectrum of Azo (c=6). A Hermes-Varian Mercury Plus 300 operating at 300 MHz was utilized for $^1$H-NMR spectroscopy with chemical shifts reported as ppm (parts per million). $^1$H NMR: δ 7.64 (2H, dd, —Ar—H), 7.37 (2H, d, —Ar—H), 2.67-2.48 (2H, m, —Ar—CH$_2$), 1.61 (2H, t, —Ar—CH$_2$CH$_2$), 1.28 (6H, t, —(CH$_2$)$_3$).086 (3H, t, —(CH$_2$)$_3$—CH$_3$).

FIG. 40—ECM proteins identified in proteomic analysis of PyVT mouse. 71 ECM proteins were identified.

DETAILED DESCRIPTION OF THE INVENTION

Definitions

Figure 1:
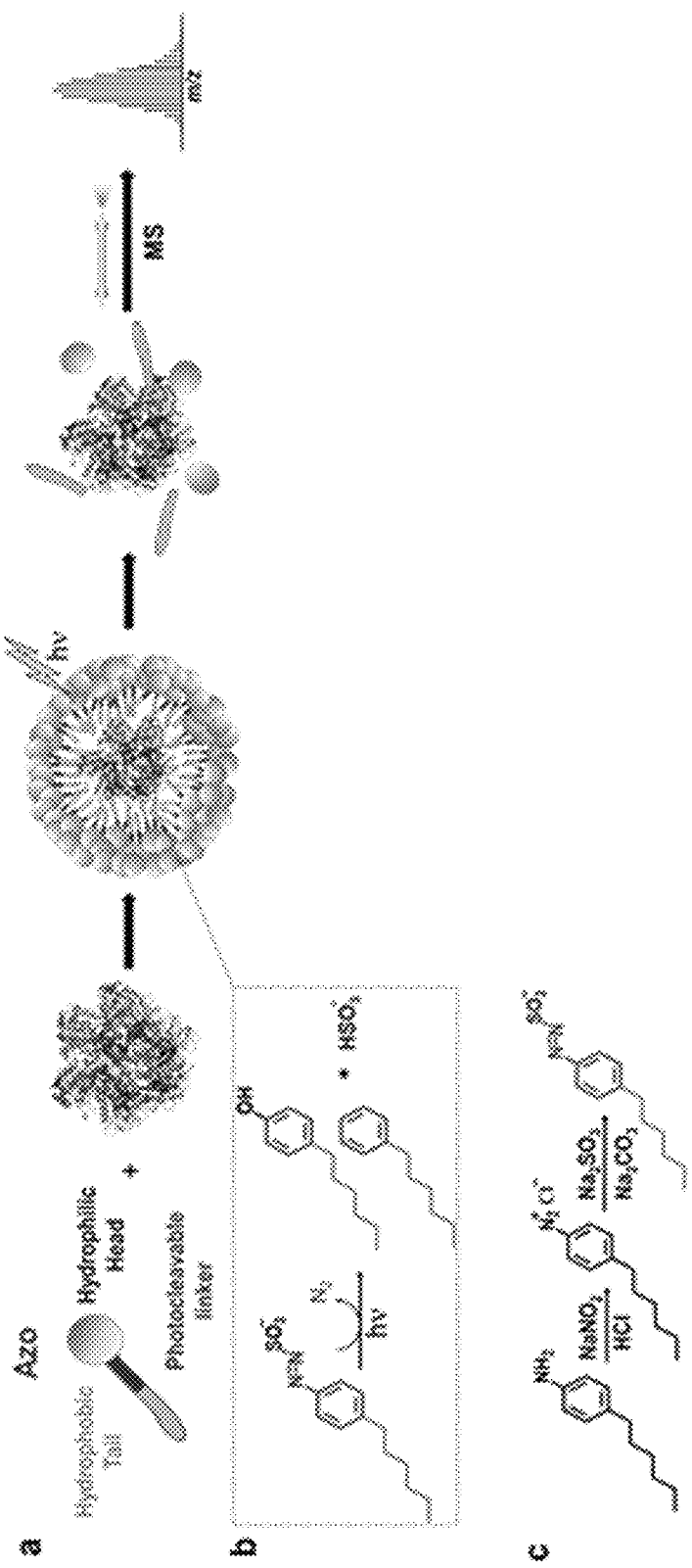
FIG. 1—Synthesis and characterization of a photo-cleavable anionic surfactant, 4-hexylphenylazosulfonate (Azo). Panel (a), scheme illustrating the use of Azo in solubilizing proteins, followed by rapid degradation with UV irradiation, and MS analysis of the intact proteins. Note that the molecules are not drawn to scale. Panel (b), degradation of Azo into 4-hexylphenol, 4-hexylbenzene, nitrogen, and hydrogen sulfate. Panel (c), synthetic scheme for Azo.

The terms "peptide" and "polypeptide" are used synonymously in the present disclosure, and refer to a class of compounds composed of amino acid residues chemically bonded together by amide bonds (or peptide bonds). Peptides are polymeric compounds comprising at least two amino acid residues or modified amino acid residues. Peptides include compositions comprising a few amino acids and include compositions comprising intact proteins or modified proteins. Modifications can be naturally occurring or non-naturally occurring, such as modifications generated by chemical synthesis. Modifications to amino acids in polypeptides include, but are not limited to, phosphorylation, glycosylation, lipidation, prenylation, sulfonation, hydroxylation, acetylation, methionine oxidation, alkylation, acylation, carbamylation, iodination and the addition of cofactors. Peptides include proteins and further include compositions generated by degradation of proteins, for example by proteolytic digestion. Peptides and polypeptides may be generated by substantially complete digestion or by partial digestion of proteins. Identifying or sequencing a peptide refers to determination of is composition, particularly its amino acid sequence, and characterization of any modifications of one or more amino acids comprising the peptide or polypeptide.

"Protein" refers to a class of compounds comprising one or more polypeptide chains and/or modified polypeptide chains. Proteins may be modified by naturally occurring processes such as post-translational modifications or co-translational modifications. Exemplary post-translational modifications or co-translational modifications include, but are not limited to, phosphorylation, glycosylation, lipidation, prenylation, sulfonation, hydroxylation, acetylation, methionine oxidation, the addition of cofactors, proteolysis, and assembly of proteins into macromolecular complexes. Modification of proteins may also include non-naturally occurring derivatives, analogues and functional mimetics generated by chemical synthesis. Exemplary derivatives include chemical modifications such as alkylation, acylation, carbamylation, iodination or any modification that derivatizes the protein. Proteins of the present invention may be derived from sources, which include but are not limited to cells, cell or tissue lysates, cell culture medium after cell growth, whole organisms or organism lysates or any excreted fluid or solid from a cell or organism.

"Fragment" refers to a portion of molecule, such as a peptide. Fragments may be singly or multiple charged ions. Fragments may be derived from bond cleavage in a parent molecule, including site specific cleavage of polypeptide bonds in a parent peptide. Fragments may also be generated from multiple cleavage events or steps. Fragments may be a truncated peptide, either carboxy-terminal, amino-terminal or both, of a parent peptide. A fragment may refer to products generated upon the cleavage of a polypeptide bond, a C—C bond, a C—N bond, a C—O bond or combination of these processes. Fragments may refer to products formed by processes whereby one or more side chains of amino acids are removed, or a modification is removed, or any combination of these processes. Fragments useful in the present invention include fragments formed under metastable conditions or result from the introduction of energy to the precursor by a variety of methods including, but not limited to, collision induced dissociation (CID), surface induced dissociation (SID), laser induced dissociation (LID), electron capture dissociation (ECD), electron transfer dissociation (ETD), or any combination of these methods or any equivalents known in the art of tandem mass spectrometry. Fragments useful in the present invention also include, but are not limited to, x-type fragments, y-type fragments, z-type fragments, a-type fragments, b-type fragments, c-type fragments, internal ion (or internal cleavage ions), immonium ions or satellite ions. The types of fragments derived from a parent analyte, such as a polypeptide analyte, often depend on the sequence of the parent, method of fragmentation, charge state of the parent precursor ion, amount of energy introduced to the parent precursor ion and method of delivering energy into the parent precursor ion. Properties of fragments, such as molecular mass, may be characterized by analysis of a fragmentation mass spectrum.

The term "alkyl" refers to a monoradical of a branched or unbranched (straight-chain or linear) saturated hydrocarbon and to cycloalkyl groups having one or more rings. Alkyl groups as used herein include those having from 1 to 30 carbon atoms, preferably having from 1 to 12 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cycoalkyl groups include those having one or more rings. Cyclic alkyl groups include those having a 3—, 4-, 5-, 6-, 7-, 8-, 9-, 10-, 11- or 12-member carbon ring and particularly those having a 3—, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group linked to oxygen and can be represented by the formula R—O. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups.

The term "alkenyl" refers to a monoradical of a branched or unbranched unsaturated hydrocarbon group having one or more double bonds and to cycloalkenyl groups having one or more rings wherein at least one ring contains a double bond. Alkenyl groups include those having 1, 2 or more double bonds and those in which two or more of the double bonds are conjugated double bonds. Alkenyl groups include those having from 1 to 20 carbon atoms, preferably having from 1 to 12 carbon atoms or 1 to 6 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those having one or more rings. Cyclic alkenyl groups include those in which a double bond is in the ring or in an alkenyl group attached to a ring. Cyclic alkenyl groups include those having a 3—, 4-, 5-, 6-, 7-, 8-, 9-, 10-, 11- or 12-member carbon ring and particularly those having a 3—, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

The term "aryl" refers to a chemical group having one or more 5-, 6- or 7-member aromatic or heterocyclic aromatic rings. An aromatic hydrocarbon is a hydrocarbon with a conjugated cyclic molecular structure. Aryl groups include those having from 4 to 30 carbon atoms, preferably having from 6 to 18 carbon atoms. Aryl groups can contain a single ring (e.g., phenyl), one or more rings (e.g., biphenyl) or multiple condensed (fused) rings, wherein at least one ring is aromatic (e.g., naphthyl, dihydrophenanthrenyl, fluorenyl, or anthryl). Heterocyclic aromatic rings can include one or more N, O, or S atoms in the ring. Heterocyclic aromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following benzene, naphthalene, naphthoquinone, diphenylmethane, fluorene, fluoranthene, anthracene, anthraquinone, phenanthrene, tetracene, naphthacenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic radical, including monovalent, divalent and polyvalent radicals, of the aromatic and heterocyclic aromatic groups listed above provided in a covalently bonded configuration in the compounds of the present invention. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

As used herein, the term "alkylene" refers to a divalent radical derived from an alkyl group or as defined herein. Alkylene groups in some embodiments function as attaching and/or spacer groups in the present compositions. Compounds of the present invention include substituted and unsubstituted $C_1$-$C_{30}$ alkylene, $C_1$-$C_{12}$ alkylene, $C_2$-$C_{18}$ alkylene, $C_5$-$C_{12}$ alkylene, $C_7$-$C_{12}$ alkylene and $C_1$-$C_5$ alkylene groups. The term "alkylene" includes cycloalkylene and non-cyclic alkylene groups.

As used herein, the term "cycloalkylene" refers to a divalent radical derived from a cycloalkyl group as defined herein. Cycloalkylene groups in some embodiments function as attaching and/or spacer groups in the present compositions. Compounds of the present invention include substituted and unsubstituted $C_1$-$C_{30}$ cycloalkenylene, $C_1$-$C_{12}$ cycloalkenylene and $C_1$-$C_5$ cycloalkenylene groups.

As used herein, the term "alkenylene" refers to a divalent radical derived from an alkenyl group as defined herein. Alkenylene groups in some embodiments function as attaching and/or spacer groups in the present compositions. Compounds of the present invention include substituted and unsubstituted $C_1$-$C_{20}$ alkenylene, $C_1$-$C_{12}$ alkenylene, $C_6$-$C_{18}$ alkenylene, $C_5$-$C_{12}$ alkenylene, $C_7$-$C_{12}$ alkylene, and $C_1$-$C_5$ alkenylene groups. The term "alkenylene" includes cycloalkenylene and non-cyclic alkenylene groups.

As used herein, the term "cycloalkenylene" refers to a divalent radical derived from a cylcoalkenyl group as defined herein. Cycloalkenylene groups in some embodiments function as attaching and/or spacer groups in the present compositions.

Optional substitution of any alkyl, alkylene, alkenyl, alkenylene, and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents alkyl, alkylene, alkenyl, alkenylene, and aryl groups include among others:
- —COOR where R is a hydrogen or an alkyl group or an aryl group and more specifically where R is methyl, ethyl, propyl, butyl, or phenyl groups all of which are optionally substituted;
- —COR where R is a hydrogen, or an alkyl group or an aryl groups and more specifically where R is methyl, ethyl, propyl, butyl, or phenyl groups all of which groups are optionally substituted;
- —CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
- —OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
- —N(R)$_2$ where each R, independently of each other R, is an alkyl group, acyl group or an aryl group and more specifically where R is methyl, ethyl, propyl, butyl, or phenyl or acetyl groups all of which are optionally substituted; or R and R can form a ring which may contain one or more double bonds.
- —SR, —SO$_2$R, or —SOR where R is an alkyl group or an aryl groups and more specifically where R is methyl, ethyl, propyl, butyl, phenyl groups all of which are optionally substituted; for —SR, R can be hydrogen;
—OCOOR where R is an alkyl group or an aryl groups;
—SO$_2$N(R)$_2$ where R is a hydrogen, an alkyl group, or an aryl group and R and R can form a ring;
—OR where R is H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

Specific substituted alkyl and alkylene groups include halo groups, including trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As used herein, the term "halo" refers to a halogen group such as a fluoro (—F), chloro (—CI), bromo (—Br) or iodo (—I).

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Overview

In the post-genomics era, a comprehensive analysis of "proteoforms" that arise from genetic variations and post-translational modifications (PTMs) is essential for understanding biological systems at a functional level toward deciphering disease mechanisms as well as identifying key diagnostic markers and new therapeutic targets. Bottom-up and top-down mass spectrometry (MS)-based proteomics are powerful methods to comprehensively characterize proteoforms to decipher the PTM codes together with sequence variations. However, protein solubility remains a major challenge in bottom-up and top-down proteomics and it is critical to develop MS-compatible surfactants that can quickly degrade into innocuous non-surfactant byproducts prior to MS analysis.

The present application reports the discovery and development of photo-cleavable anionic surfactants, particularly 4-hexylphenylazosulfonate (Azo) and sodium 4-hexylphenylazosulfonate, which can be rapidly degraded upon electromagnetic irradiation (e.g., UV radiation), for biological and chemical applications such as top-down proteomics. Azo can effectively solubilize proteins with performance comparable to SDS and is compatible with mass spectrometry analysis, including top-down and bottom-up analysis.

For instance, in experiments Azo-aided top-down proteomics has allowed the detection of 100-fold more unique proteoforms as compared to controls and enabled the solubilization of membrane proteins for comprehensive characterization of post-translational modifications. It is believed the surfactants described herein are the first MS-compatible cleavable surfactants developed for top-down proteomics.

As described below, a library of anionic surfactants was synthesized with a cleavable linker between the hydrophilic head and hydrophobic tail. In some experiments, swine heart tissue was homogenized twice in HEPES buffer and once in a surfactant solution. The resulting protein extract was separated by SDS-PAGE and stained with Coomassie blue. The leading surfactant, based on the highest concentration of extracted proteins, was tested for MS-compatibility by directly infusing an ubiquitin-surfactant solution into the mass spectrometer to evaluate signal suppression. Finally, the heart protein extract was separated by reversed-phase liquid chromatography (RPLC), infused into the mass spectrometer (Buker maXis II QTOF) via ESI, and fragmented using collisionally activated dissociation (CAD) yielding sequence information and identifications using MASH Suite Pro with TopPIC.

After screening the cleavable surfactant library, one surfactant (referred as "Azo") was identified as the most effective solubility agent. SDS-PAGE analysis and Bradford Assay demonstrated that the Azo surfactant extracted proteins at a similar level to SDS. Furthermore, Western blot analysis confirmed the extraction of common cardiac membrane proteins such as phospholamban, voltage-dependent anion-selective channel, cadherin, and sodium-potassium adenosine triphosphatase. It was observed, by UV-Vis spectroscopy, that Azo degraded rapidly (30-150s) under various solvent conditions (i.e. aqueous, organic, neutral pH, low pH), making it amenable to high-throughput TDP. In addition, it was verified that the surfactant was compatible with ESI-MS analysis of Ubiquitin while other anionic surfactants like SDS completely suppressed the signal.

The biological application of this technology was demonstrated by evaluating surfactant-aided swine heart tissue lysate using RPLC-MS/MS. The tissue was first homogenized in HEPES to deplete water-soluble proteins in order to evaluate the surfactants ability to increase the proteome coverage. Many unique protein masses (663) were observed that were not present without surfactant. Furthermore, a number of proteins and their PTMs (including acetylation, methylation, phosphorylation, and palmitoylation) were able to be identified using online RPLC-MS/MS. Overall the data was reproducible for sample replicates and could be applied to a number of systems to ameliorate the technical challenge associated with solubilizing intact protein species. The characterization of hydrophobic membrane proteins such as phospholamban and ATP synthase subunit C along their respective PTMs was particularly promising. This technology is also able to probe the membrane proteome including PTMs of plasma membrane proteins. Overall the results demonstrate the surfactant is compatible with a range of proteins with various physiochemical properties and sizes (online identification of proteins as large as 55 kDa) and can assist in clinically relevant studies as well as global proteome analysis if coupled to multidimensional separation methods.

EXAMPLES

Example 1—Synthesis and Characterization of Azo

In an approach, a library of surfactants was designed with a photo-cleavable moiety between the hydrophobic tail and the hydrophilic head aiming for rapid, controlled cleavage and subsequent loss of surface activity (Tehrani-Bagha et al., 2007, Current Opinion in Colloid & Interface Science, 12:81-91). Specifically, O-nitrobenzyl (ONB), O-nitroveratryl (ONV), and azobenzene (AZO) groups were chosen as linkers because of their rapid degradation kinetics (Bradley et al., 2006, Langmuir, 22:101-105; Kim et al., 2006, Bioorg Med Chem Lett, 16:4007-4010; Yan et al., 2013, Journal of the American Chemical Society, 135:8382-8387; Hwang et al., 2016, Langmuir, 32:3963-3969; and Hwang et al., 2016, Langmuir, 32:3963-3969). The properties of the most widely used biological surfactant, SDS, was mimicked by using a sulfonate head for the hydrophilic portion to maximize protein solubility (Prive et al., 2007, Methods, 41:388-397). Various chain lengths were synthesized to optimize the hydrophilic-lipophilic balance character of the surfactants.

After the synthesis and characterization (see Schemes 1-3, and FIGS. 7 and 8), the surfactants with poor water solubility such as ONB surfactant series (C=8, 10, 12) from the library (see Table 1, below) were excluded from further screening. The performance of soluble surfactants such as AZO (C-8, 6) and ONV (C=8, 10, 12) were then evaluated in extracting proteins from tissue extracts since tissues present the most significant challenge for protein solubilization (Chang et al., 2015, Journal of Proteome Research, DOI: 10.1021/pr5012679; and Kim et al., 2014, Nature, 509:575-581). Specifically, the surfactants were used to extract proteins from an "insoluble" cardiac tissue pellet after homogenizing cardiac tissue first in HEPES buffer to deplete soluble proteins. Sodium dodecyl sulfate-polyacrylamide gel electrophoresis (SDS-PAGE) were employed for side-by-side comparison of protein concentration after the surfactant-aided extraction. Overall, AZO (C=6), referred to as "Azo", was demonstrated to be the top-performing surfactant which is not only water-soluble but also can effectively solubilize proteins from the insoluble tissue pellet (Table 1, below).

Figure 7:
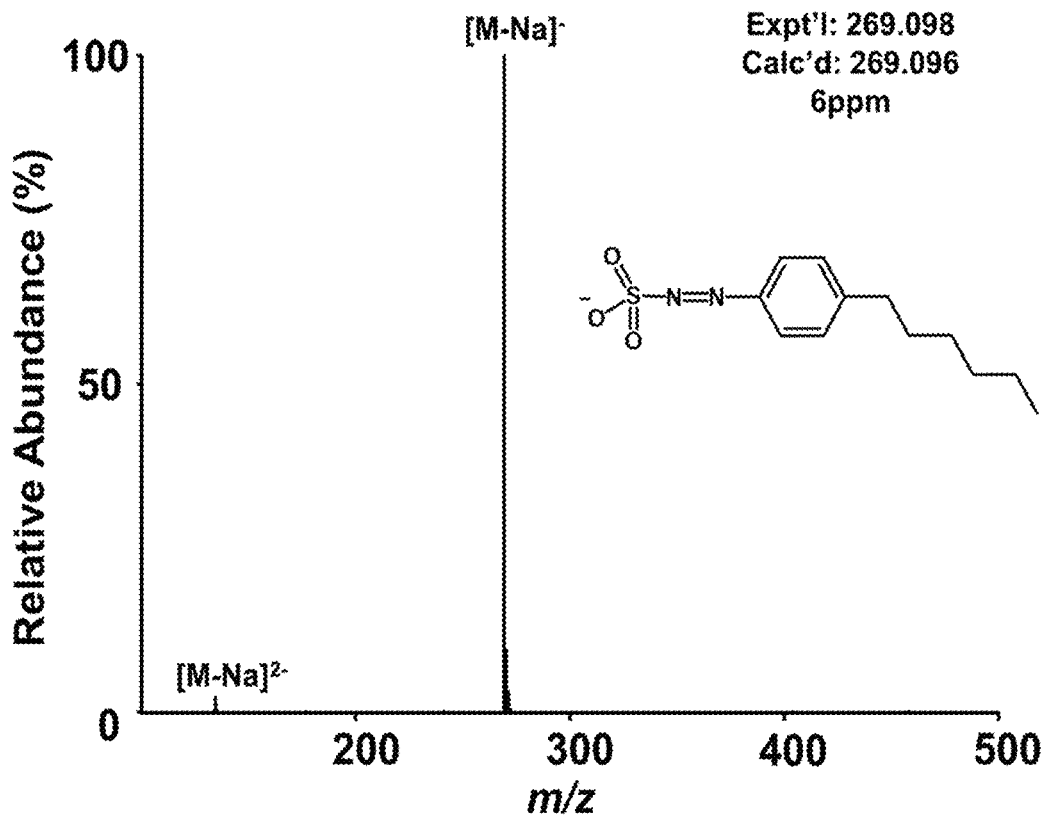
FIG. 7—Negative ion ESI-FT-ICR mass spectrum of 4-hexylphenylazosulfonate (Azo).
Figure 8:
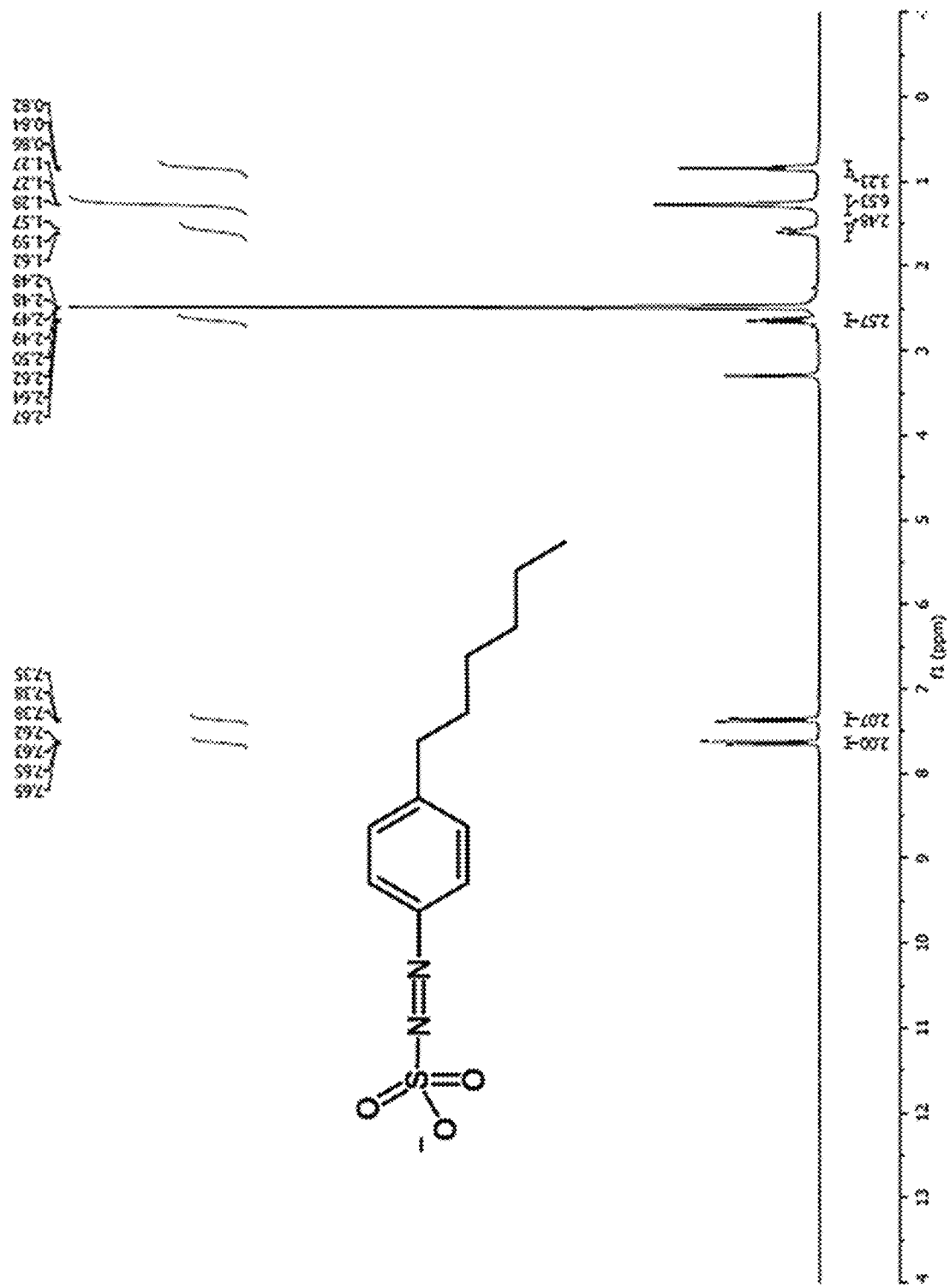
Figure 9:
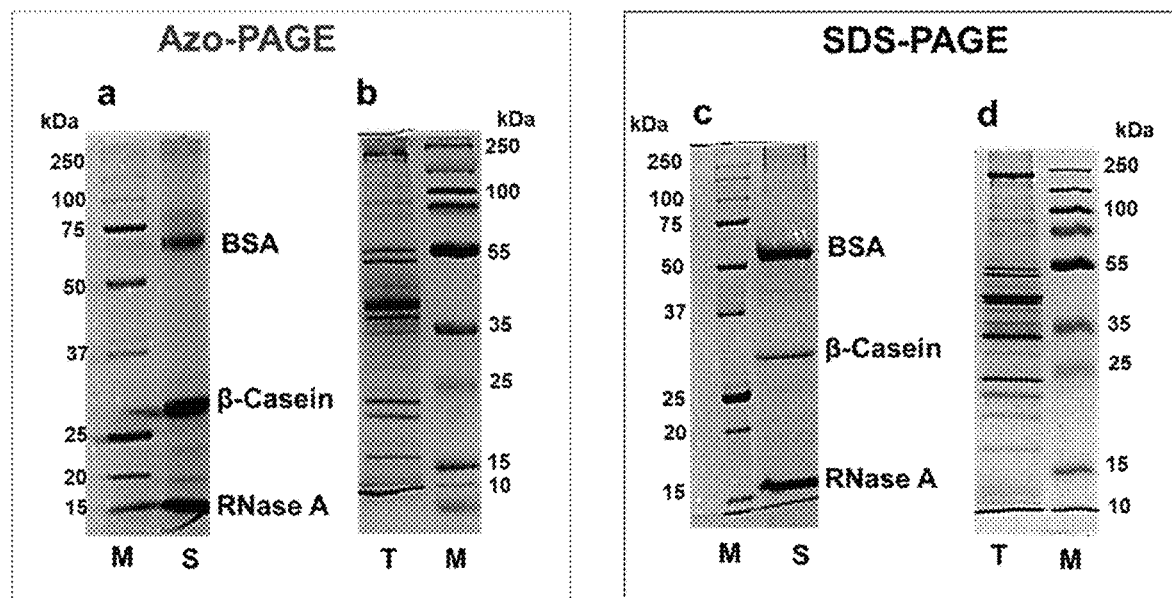
FIG. 9—Polyacrylamide gel electrophoresis (PAGE) using Azo (panels a and b) and SDS (panels c and d). Azo-PAGE analysis of (panel a) 2.5 μg bovine serum albumin (BSA), β-casein, and ribonuclease A (RNase A), and (panel b) myofilament cardiac tissue protein extract with Coomassie blue staining. SDS-PAGE analysis of (panel c) 2.5 μg BSA, B-Casein, and RNase A, and (panel d) myofilament cardiac tissue protein extract with Coomassie blue staining. M: molecular weight ladder; S: standard proteins, T, myofilament protein extract.

The structure of Azo was characterized and verified with high-resolution Fourier transform ion cyclotron resonance (FTICR)-MS in the negative ion electrospray ionization (ESI) mode as well as NMR (FIGS. 7 and 8). Notably, Azo was simple to synthesize, requiring only two steps (FIG. 1, panel c), and could be effectively purified using recrystallization, making it an ideal candidate for general use as a surfactant in biological and chemical applications. For instance, Azo was used instead of SDS to perform polyacrylamide gel electrophoresis (PAGE) (Table 4), which demonstrates that Azo could be used as a SDS replacement in SDS-PAGE (FIG. 9).

Figure 2:
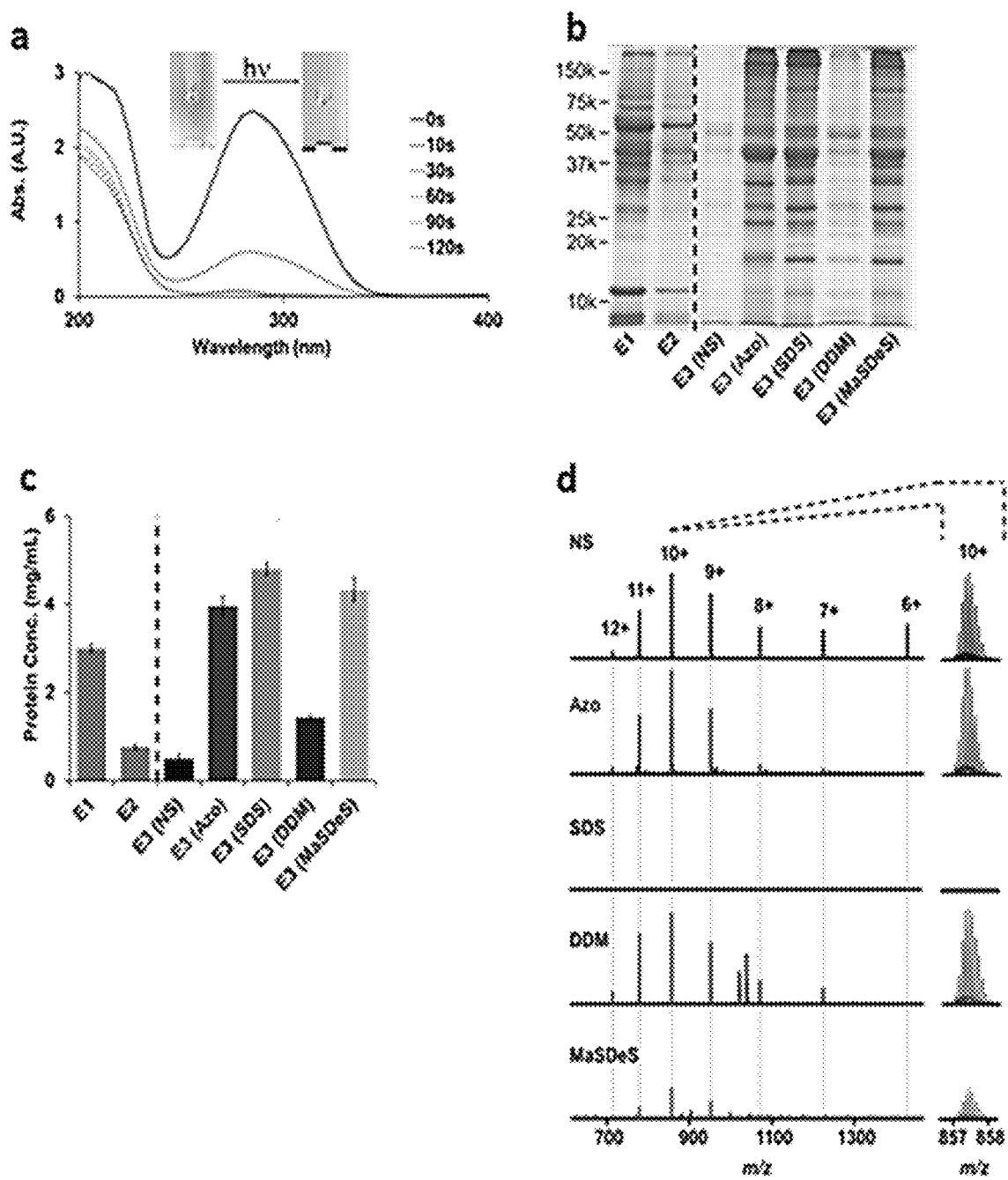
FIG. 2—Panel (a), UV-Vis spectra of Azo (0.1%) degradation as a function of time showing that Azo can be rapidly degraded upon UV irradiation at ambient temperature. Panels (b) and (c), SDS-PAGE analysis (panel c) and Pierce™ 660 nm protein assay with ionic detergent compatibility for the evaluation (panel b) of effectiveness of surfactant aided protein extractions (E3) following the initial HEPES buffer extractions (E1 & E2) to deplete the cytosolic proteins. An equal volume of each extract was used. Panel (d), electrospray ionization (ESI)-MS analysis of Ubi with 0.1% surfactant showed the MS-compatibility of surfactants. The mass spectra were normalized to an intensity of 1.7E6. NS, no surfactant (serving as controls); Azo; SDS, sodium dodecyl sulfate; DDM, n-dodecyl β-D-maltoside; MaSDeS, MS-compatible slowly degradable surfactant.
Figure 11:
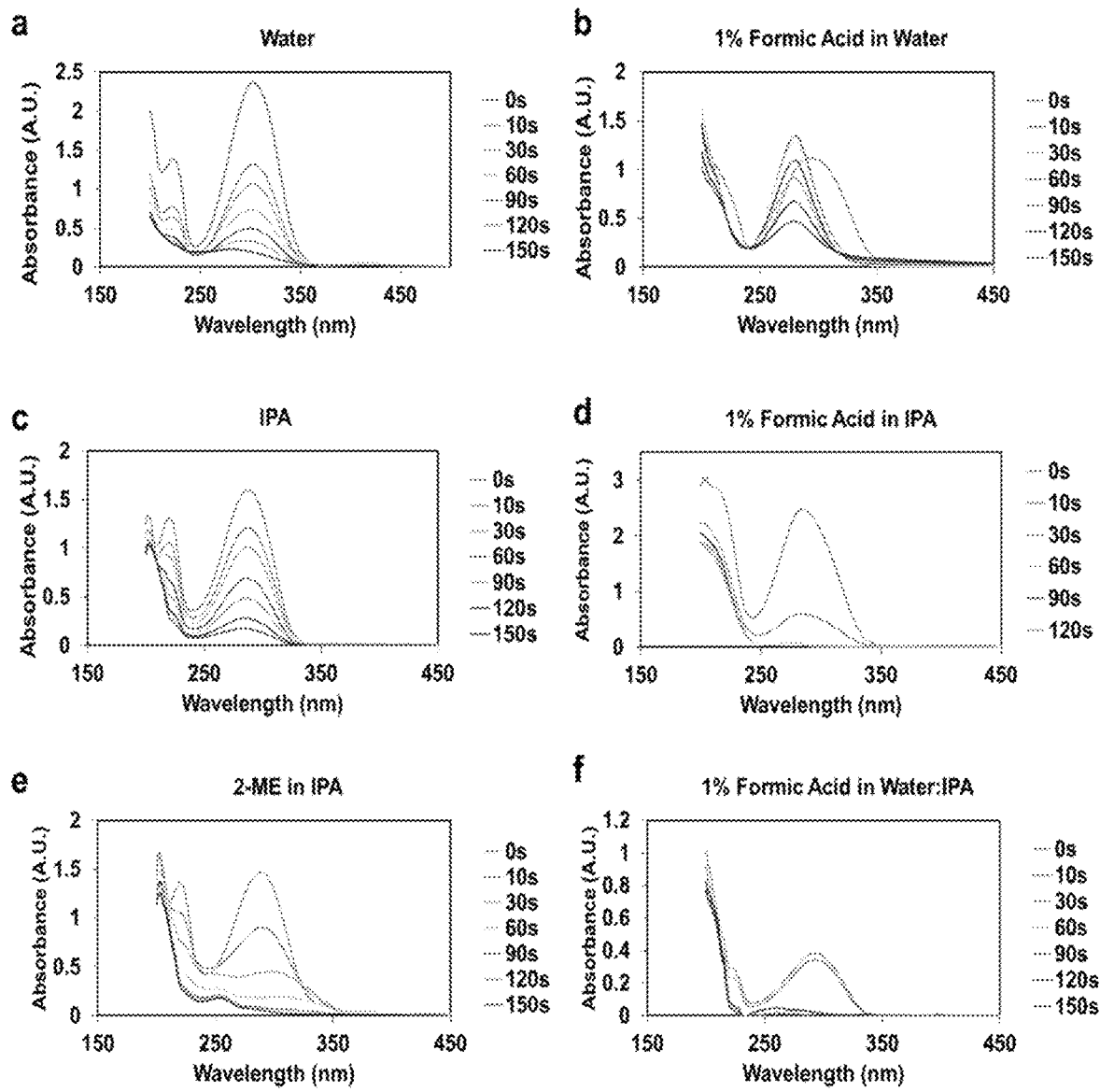
FIG. 11—Effects of solvent conditions on Azo degradation kinetics. Azo (0.1%) was degraded in different solvent conditions; panel (a) water, panel (b) 1% formic acid in water, panel (c) IPA, panel (d) 1% formic acid in IPA, panel (e) 2-ME in IPA, panel (f) 1% formic acid in 50:50 mixture of water: IPA, respectively, to probe their effects on degradation kinetics. Overall the surfactant degraded rapidly particularly in the presence of organic solvent at low pH (panels d and f).

The Azo6 surfactant was further characterized using UV-Vis spectroscopy to monitor the photo-degradation of the surfactant into 4-hexylphenol, 4-hexylbenzene, nitrogen, and hydrogen sulfate (Chang et al., 2015, J Proteome Res, 14 (3): 1587-99) (see FIG. 1, panel b) upon irradiation with a 100 W high pressure mercury lamp for 0, 10, 30, 60, 90, and 120 s using UV-Vis spectroscopy (FIG. 2, panel a). Several degradation conditions were compared (i.e., organic vs. aqueous solutions in the presence or absence of acid and reducing agents) to determine the most favorable conditions (FIG. 11). It was observed that the presence of organic solvent and acid facilitates rapid degradation of 0.1% Azo (FIG. 1, panel b).

The effectiveness of Azo for solubilizing proteins from cardiac tissues was then investigated with a direct side-by-side comparison with the strongest surfactant, SDS, and its acid-labile mimic, MasDeS which has shown comparable performance as SDS in protein solubilization (Chang et al., 2015, Journal of Proteome Research, 14:1587-1599), as well as dodecyl B-D-maltoside (DDM), a commonly used surfactant for native MS. As demonstrated in the SDS-gel (FIG. 2, panel b) and protein assay with ionic detergent compatibility (FIG. 2, panel c), the addition of 0.5% Azo to the extraction buffer, E3 (Azo), drastically improved the solubilization of proteins, as compared to the control, E3 (NS), which barely solubilize proteins after the depletion of soluble proteins in HEPES extractions, E1 and E2. Overall, the anionic surfactants, Azo, SDS, and MaSDeS, are highly effective in solubilizing proteins compared to the non-ionic surfactant, DDM (FIG. 2, panels b and c). For the protein solubility experiment (FIG. 2, panel c) comparing Azo, SDS, DDM, and MaSDeS, three independent protein assays (n=3) were performed to evaluate surfactant performance. Error bars represent standard error of the mean.

Figure 10:
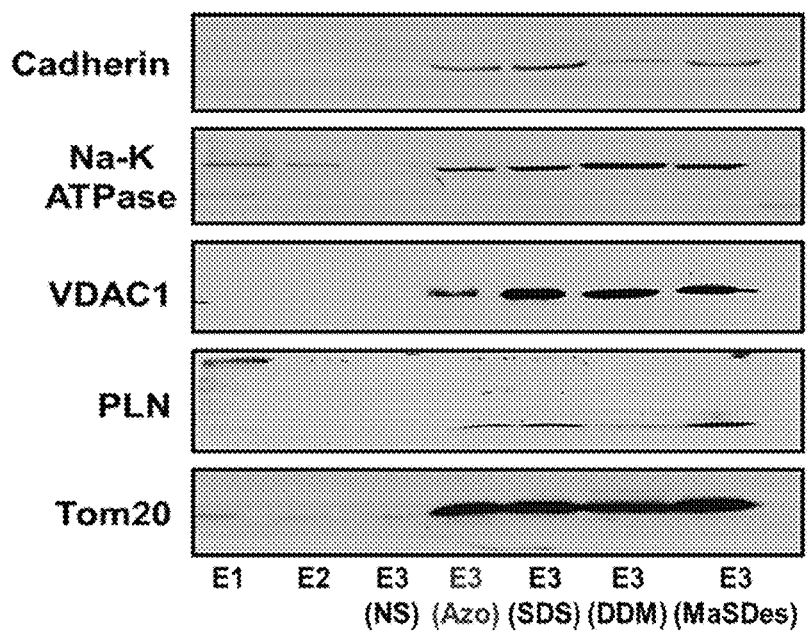
FIG. 10—Evaluation of surfactant-aided extraction of cardiac membrane proteins using western blot analysis. Western blot analysis of common cardiac membrane proteins, cadherin, sodium potassium adenosine triphosphate (Na—K ATPase), voltage-dependent anion-selective channel (VDAC), phospholamban (PLN), and mitochondrial import receptor subunit (TOM20). 12.5% SDS-PAGE was used to resolve 20 μL of lysate extracted using 25 mM NH4HCO3 without surfactant (NS), or with surfactant, 4-hexylphenylazosulfonate (Azo), sodium dodecyl sulfate (SDS), dodecyl β-D-maltoside (DDM), and MS-compatible degradable surfactant (MaSDeS), respectively. The addition of Azo in the buffer successfully aided in the extraction of these five important integral membrane proteins in cardiac tissue, with performance comparable to SDS and MaSDeS.

Furthermore, a Western blot analysis confirmed the presence of common cardiac membrane proteins such as cadherin, sodium-potassium adenosine triphosphatase (Na—K-ATPase), voltage-dependent anion-selective channel protein 1 (VDAC1), phospholamban (PLN), mitochondrial import receptor subunit (TOM20) in the Azo extraction, E3 (Azo), demonstrating the successful extraction of integral membrane protein by Azo as compared to the control, E3 (NS) (FIG. 10).

Assessing the MS—compatibility of Azo. After demonstrating that Azo could effectively extract proteins from tissues, the MS-compatibility of Azo was then examined. First, a standard protein, Ubi, was analyzed by dissolving the protein in a solution of 0.1% surfactant and 80% isopropanol, 14.9% water, 5% formic acid in the direct infusion mode of ESI/MS without any additional desalting step. The results showed the presence of SDS (0.1%) completely suppressed of MS signal and 0.1% MasDeS greatly suppressed MS signal even after degradation in acid condition. On the other hand, 0.1% DDM and 0.1% Azo (after rapid degradation under UV irradiation) had relatively comparable signals showing minimal signal suppression compared to a control sample without surfactant (FIG. 2, panel d). Thus, it was concluded that among all the surfactants screened, Azo6 effectively solubilized proteins band was also compatible with MS analysis of intact proteins.

Figure 12:
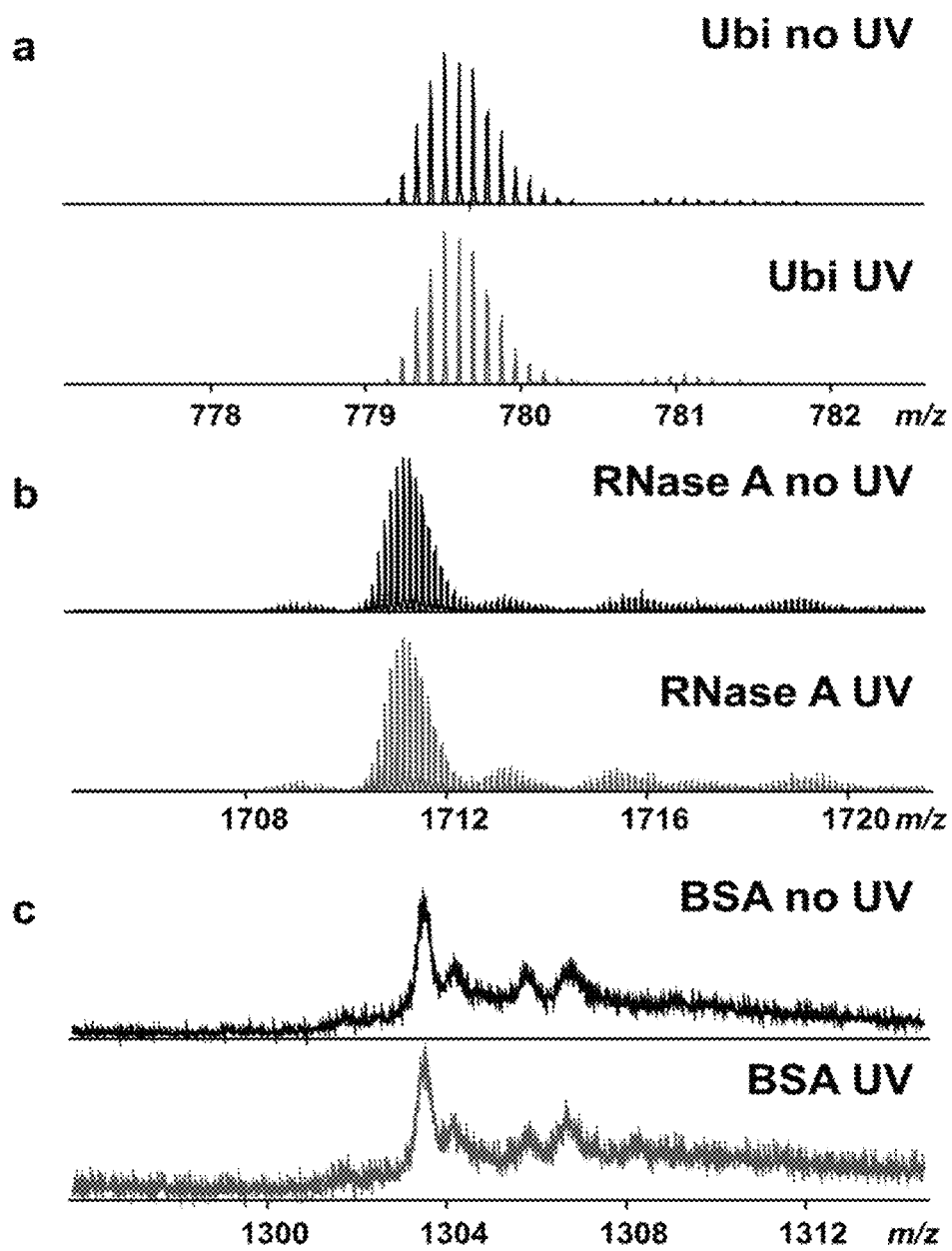
FIG. 12—Effects of exposure to ultraviolet (UV) light on selected proteins. Ubi (panel a), RNase A (panel b), and BSA (panel c) were irradiated for 3 min prior to direct injection into the MS. Overall no change was observed after irradiation. The mass spectra were collected on a Bruker maXis II Q-TOF mass spectrometer.
Figure 13:
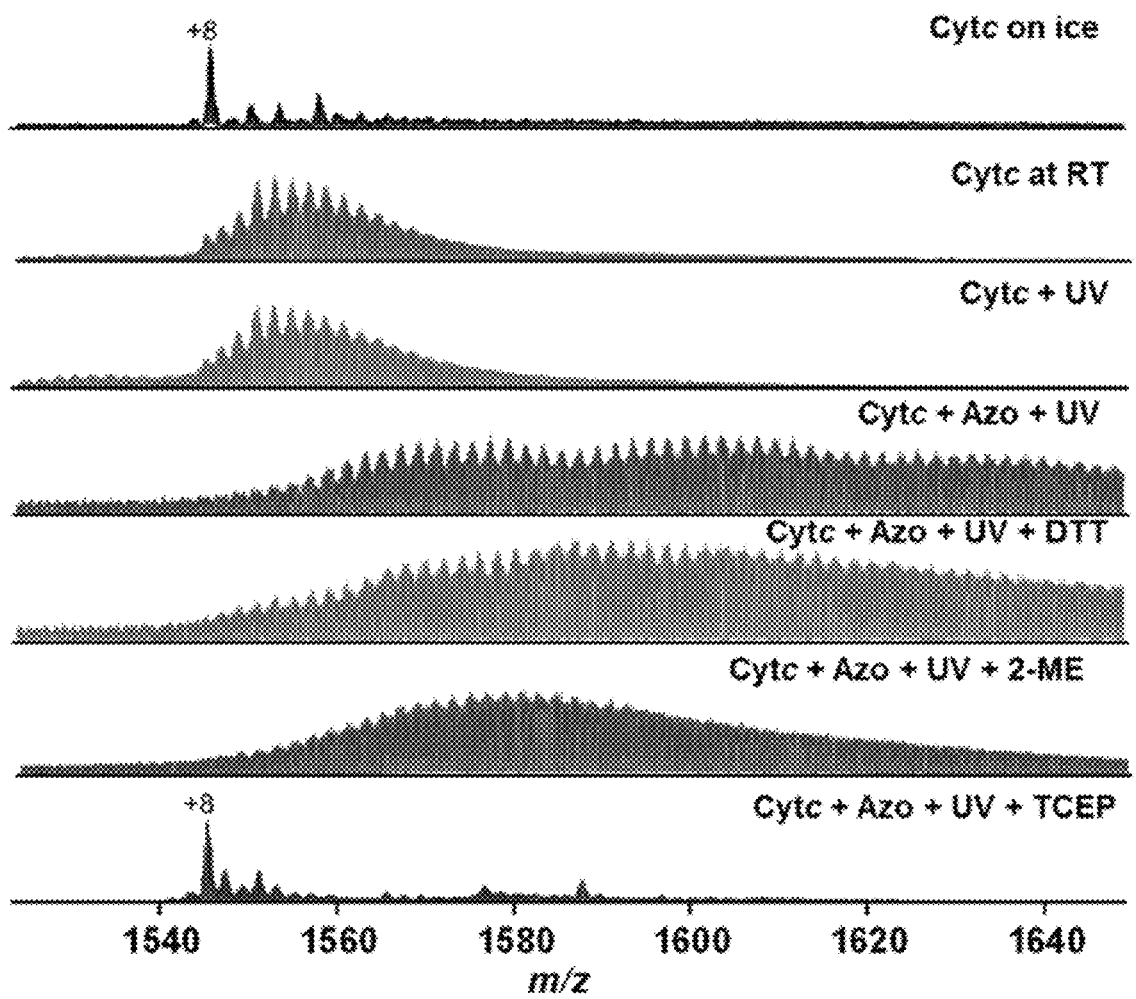
FIG. 13—The effect of addition of reducing agents during Azo degradation. A standard protein, Cytc, was panel (a) incubated on ice, panel (b) incubated on room temperature (RT), panel (c) irradiated at RT, panel (d) irradiated at RT with Azo, panel (e) irradiated at RT with Azo and 50 mM DTT, panel (f) irradiated at RT with Azo and 50 mM 2-ME, and panel (g) irradiated at RT with Azo and 50 mM TCEP before LC-MS analysis. All the incubations were done for 3 min. Overall TCEP alleviated oxidative modification observed when incubated at RT or by exposing it to the radicals generated upon photolysis of the surfactant. Mass spectra were collected on a Bruker maXis II Q-TOF mass spectrometer.

LC-MS analysis of standard proteins was performed to examine the effect of the UV degradation on MS analysis of proteins. It has been shown that UV irradiation alone did not introduce any adducts or cause any alteration to the protein mass spectrum (FIG. 12). Subsequently, it was demonstrated that the inclusion of reducing agent, TCEP, could successfully minimize the oxidative modifications resulting from exposure of the proteins to the radicals generated upon photolysis of the surfactant or heating at room temperature (FIG. 13).

Figure 14:
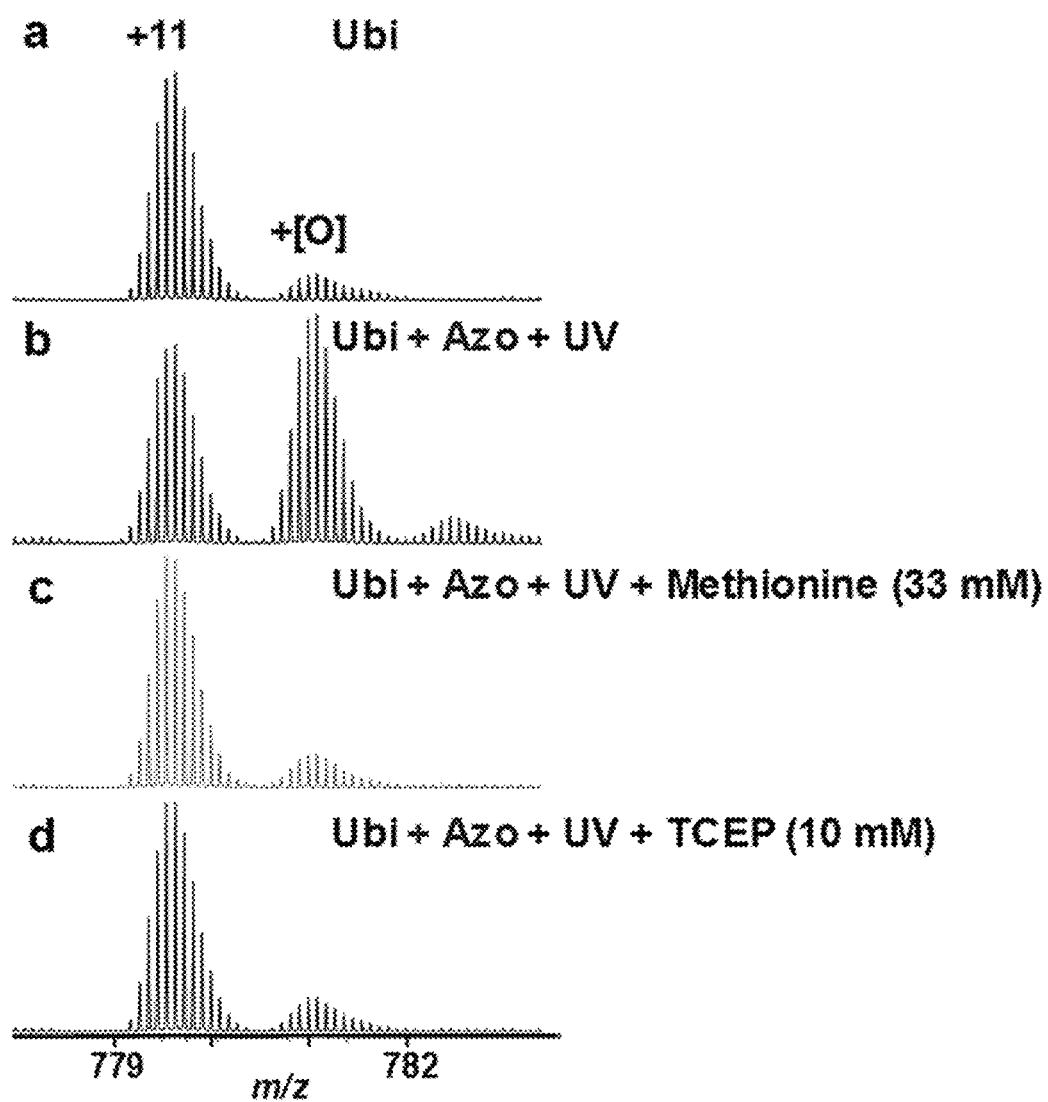
FIG. 14—The presence of methionine during Azo degradation alleviated oxidative modification. A standard protein, ubiquitin (Ubi), was panel (a) incubated on ice, panel (b) irradiated at room temp with Azo (0.1%), panel (c) irradiated at room temp with Azo (0.1%) and Methionine (33 mM), panel (d) irradiated at room temp with Azo (0.1%) and TCEP (10 mM). Mass spectra were collected on a Bruker maXis II Q-TOF mass spectrometer.
Figure 15:
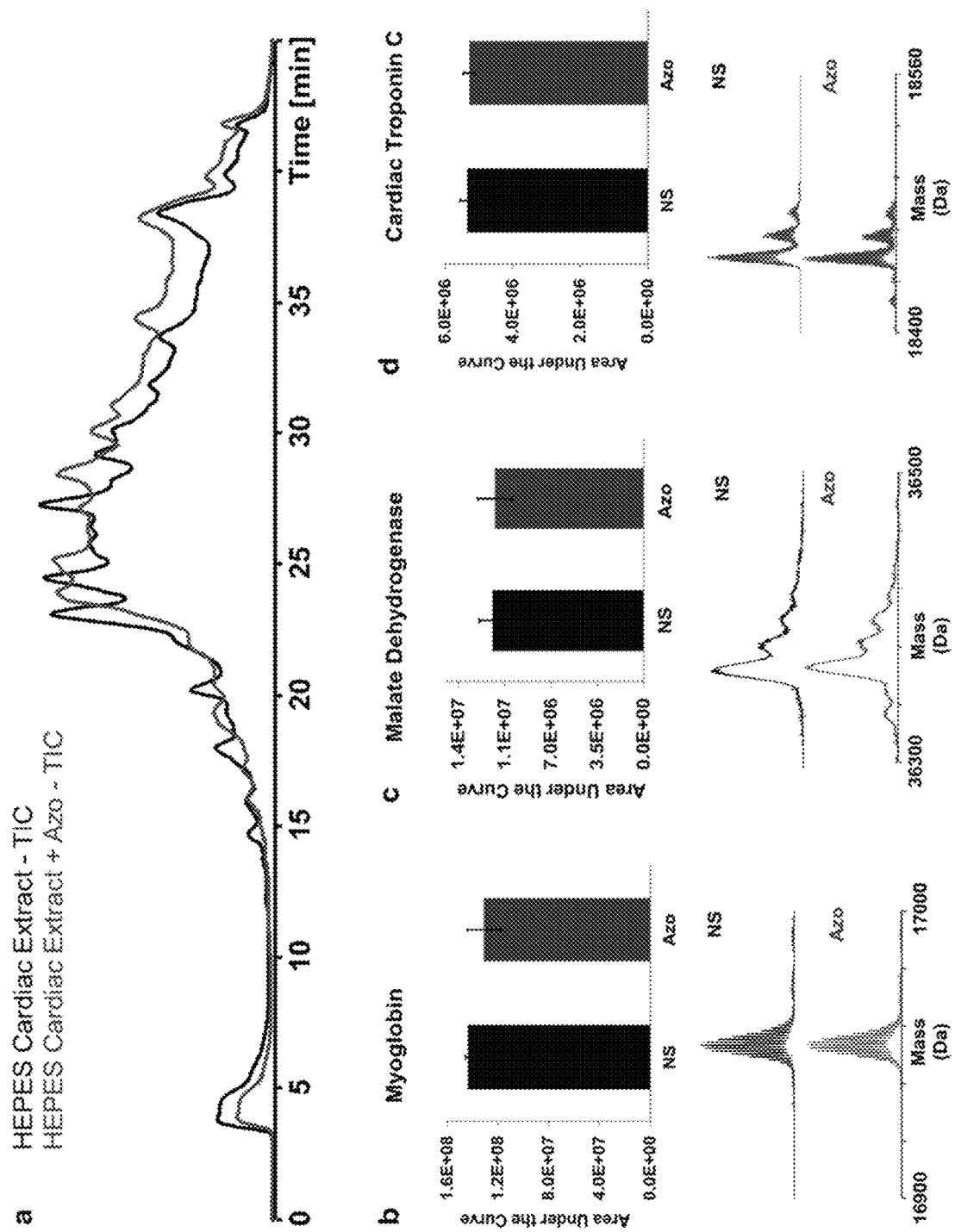
FIG. 15—Effect of Azo on relative quantitation by LC-MS using HEPES Cardiac Extract. A sample of cardiac proteins extracted using HEPES buffer was analyzed by LCMS as well as a sample spiked with Azo (0.2%). Panel (a), total ion chromatogram for HEPES Cardiac Extract and Cardiac Extract+Azo. Extracted ion chromatograms of the top 5 charges states were performed and the area under the curve calculated for panel (b) myoglobin, panel (c) malate dehydrogenase, and panel (d) cardiac troponin C. Error bars represent standard error of the mean for 3 injection replicates. Mass spectra were collected on a Bruker maXis II Q-TOF mass spectrometer.

Alternatively, free methionine could be added to minimize oxidation modification and preserve biologically relevant modifications such as disulfide and glutathionylation (FIG. 14). It was also observed that the usage of Azo had nearly no effect on the relative quantitation of intact proteins from a cardiac tissue lysate by reversed-phase liquid chromatography (RPLC)-MS (FIG. 15). Three separate samples (n=3) were prepared for each condition. Error bars represent standard error of the mean.

Figure 20:
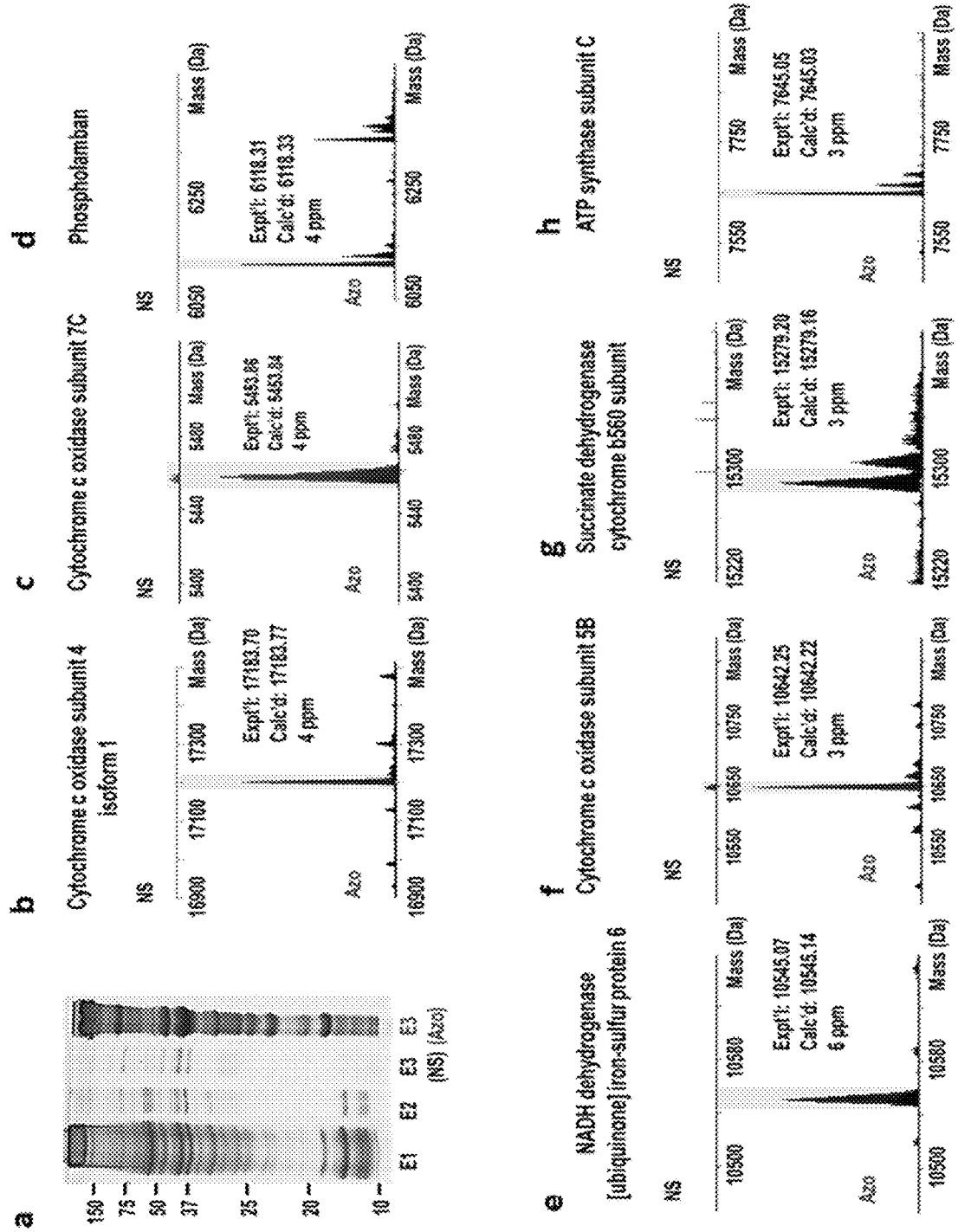
FIG. 20—Azo-enable membrane proteomics from cardiac tissue. Panel (a), SDS-PAGE analysis of cardiac proteins extracted first in a high salt buffer twice and labeled as extraction 1 (E1) and extraction 2 (E2), respectively, followed by a third extraction (E3) in 25 mM $NH_4HCO_3$ with either no surfactant (NS) or 0.5% Azo. Panels (b-h), represented deconvoluted mass spectra from LC-MS analysis using equal volume of extract (NS and Azo) confirming the enhancement of membrane protein signal that occurs by adding Azo to the extraction buffer. Panel (b), cytochrome c oxidase subunit 4 isoform 1. Panel (c), cytochrome c oxidase subunit 7C. Panel (d), phospholamban. Panel (e), NADH dehydrogenase [ubiquinone] iron-sulfur protein 6. Panel (f), succinate dehydrogenase cytochrome b560 subunit. Panel (h), ATP synthase subunit c. Mass spectra were collected on a Bruker maXis II Q-TOF mass spectrometer. Each spectrum was normalized to the intensity value corresponding to protein signal intensity in the Azo extraction FIG. 21—Representative membrane proteins identified from human embryonic kidney (HEK) Cells. Panel (a), SDS-PAGE analysis of HEK cell proteins extracted with a Tris buffer and labeled as extraction 1 (E1). The pellets were next extracted with $NH_4HCO_3$ and labeled as extraction 2 (E2). Finally a third extraction (E3) was performed using 25 mM $NH_4HCO_3$ with either no surfactant, E3 (NS), or 0.5% Azo, E3 (Azo). Representative membrane proteins identified in the E3 (Azo) extract by top-down proteomics include panel (b) ATP synthase subunit g, panel (c) eukaryotic translation initiation factor 5A, panel (d) dolichyl-diphosphooligosaccharide-protein glycosyltransferase subunit 4, panel (e) protein transport protein Sec61 subunit gamma, panel (f) mitochondrial import receptor subunit Tom22, panel (g) ATP synthase subunit c, panel (h) dolichol phosphate-mannose biosynthesis regulatory protein, panel (i) vacuolar ATPase assembly integral membrane protein VMA21, panel (j) B-cell receptor-associated protein 31, panel (k) V-type proton ATPase 16 kDa proteolipid subunit, and panel (I) ADP/ATP translocase 2. Mass spectra were collected on a Bruker maXis II Q-TOF mass spectrometer.
Figure 21:
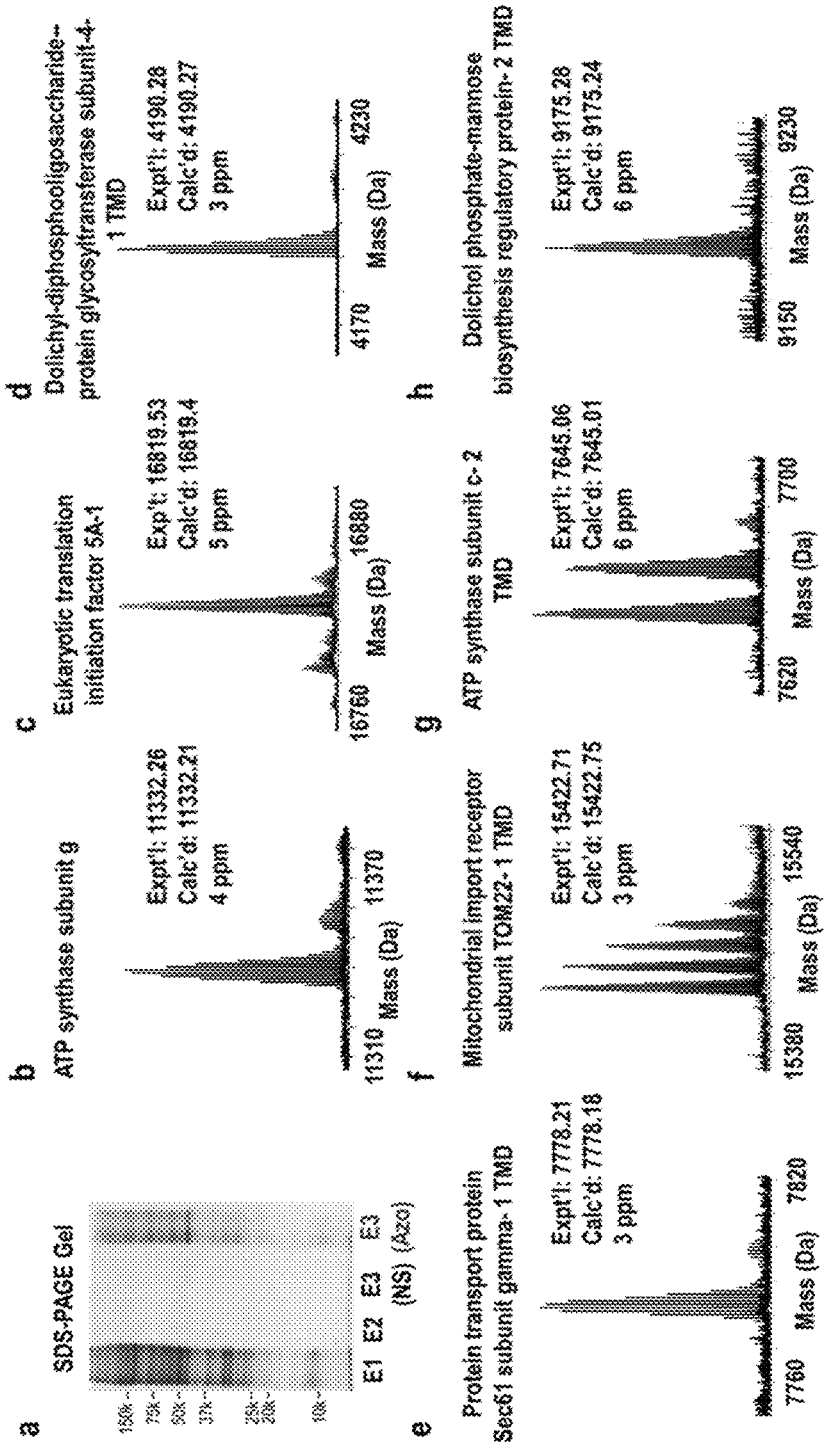
Figure 21:
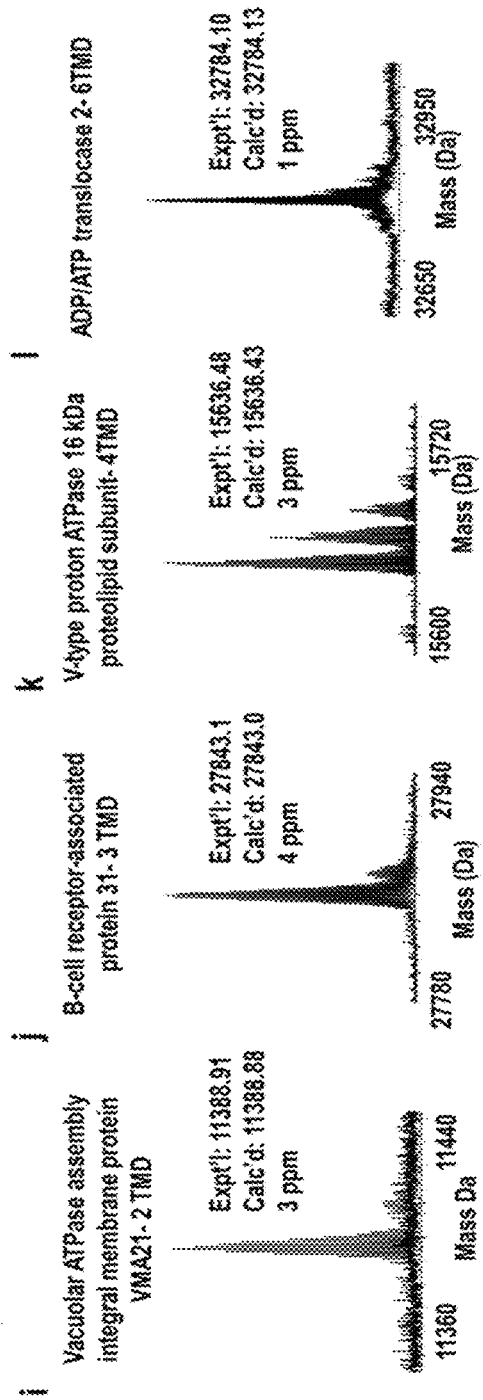
Figure 25:
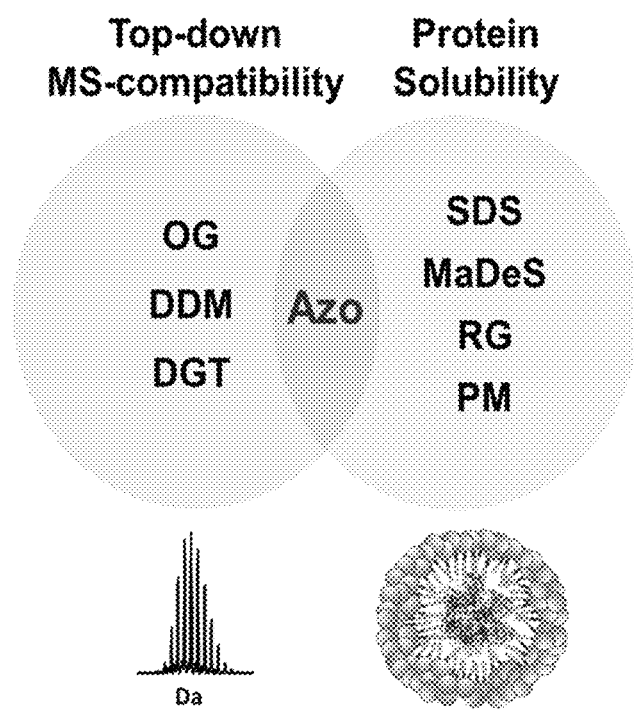
FIG. 25—Illustration showing top-down MS-compatibility and protein solubility experiments with Azo. These experiments show that Azo effectively solubilizes proteins but also is top-down MS compatible.

Comparison with other leading surfactants. Next, a systematic comparison of Azo with other commonly used surfactants in protein solubilization was performed based on the ability to solubilize proteins from the insoluble cardiac tissue pellets (similarly as described above). MS-compatibility using both standard proteins and tissue lysates was then subsequently assessed (FIGS. 20 and 21). Overall this broader comparison confirmed Azo's unique ability in effectively solubilize proteins without interfering with downstream MS analysis (FIG. 25).

The surfactants used for comparison include non-ionic surfactants, Octyl β-D-glucopyranoside (OG) and dodecyl β-D-maltoside (DDM), digitonin (DGT), as well as anionic, acid-labile surfactants, RapiGest™ (RG), ProteaseMax™ (PM), and MS-compatible slowly-degradable surfactant (MaSDeS) (Chang et al., 2015, Journal of Proteome Research, 14:1587-1599), together with SDS and Azo6. Nonionic saccharide surfactants such as DDM and OG can be MS-compatible when used at lower concentration (0.01-0.1%) but they are considered to be relatively mild with limited solubilization ability (Loo et al., 1994, Protein Sci, 3:1975-1983; and Speers et al., 2007, Chemical Reviews, 107:3687-3714). On the other hand, anionic surfactants such as SDS and acid-labile SDS mimics have much stronger surfactants which are capable of solubilizing and denaturing proteins with high efficiency (Speers et al., 2007, Chemical Reviews, 107:3687-3714). Acid-labile surfactants are developed for improving in-gel or in-solution digestion efficiency for bottom-up proteomics (Chang et al., 2015, Journal of Proteome Research, 14:1587-1599).

Figure 16:
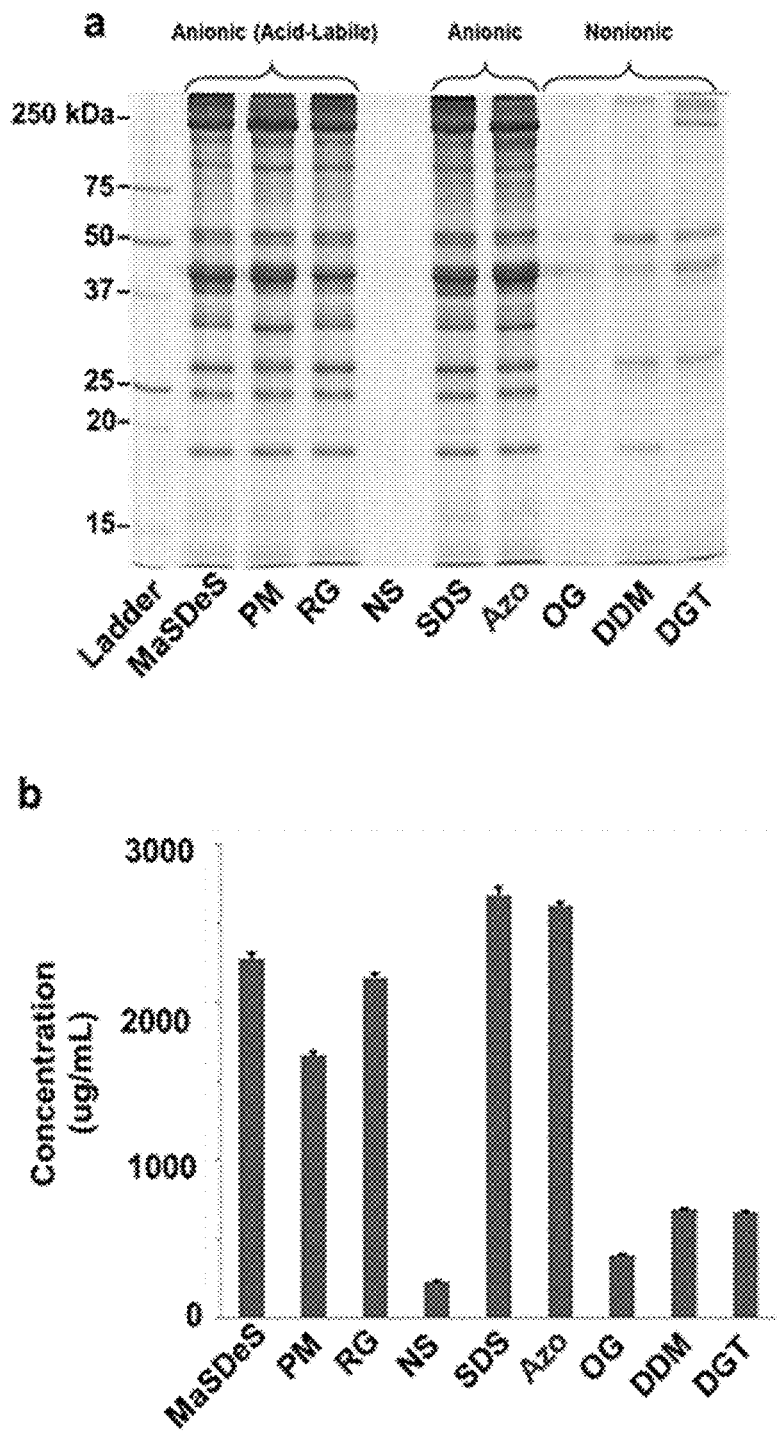
FIG. 16—Evaluation of surfactant-aided extraction of cardiac tissue using SDS-PAGE and protein assay. Swine heart proteins were extracted using 0.5% surfactant in 25 mM $NH_4HCO_3$ following a HEPES extraction to remove water-soluble proteins. Panel (a), MS-compatible degradable surfactant (MaSDeS), ProteaseMax™ (PM), RapiGest™ (RG), 25 mM $NH_4HCO_3$ with no surfactant (NS), sodium dodecyl sulfate (SDS), 4-hexylphenylazosulfonate (Azo), Octyl β-D-glucopyranoside (OG), dodecyl β-D-maltoside (DDM), digitonin (DGT) were tested. Panel (b), protein assay used to assess the extracted protein concentration facilitated by each surfactant.

Utilizing SDS-PAGE and Bradford protein assay analysis. It was observed that anionic surfactants including SDS, MaSDeS, PM, RG, and Azo6 showed drastically better protein solubilization ability than the non-ionic surfactants, OG, DDM and DGT (FIG. 16). In particular, Azo effectively extracted proteins at a level similar to SDS, comparable to MasDes, and slightly better than RG and PM (FIG. 16). Data presented were based on three independent experiments (n=3). Error bars represent standard error of the mean.

Figure 17:
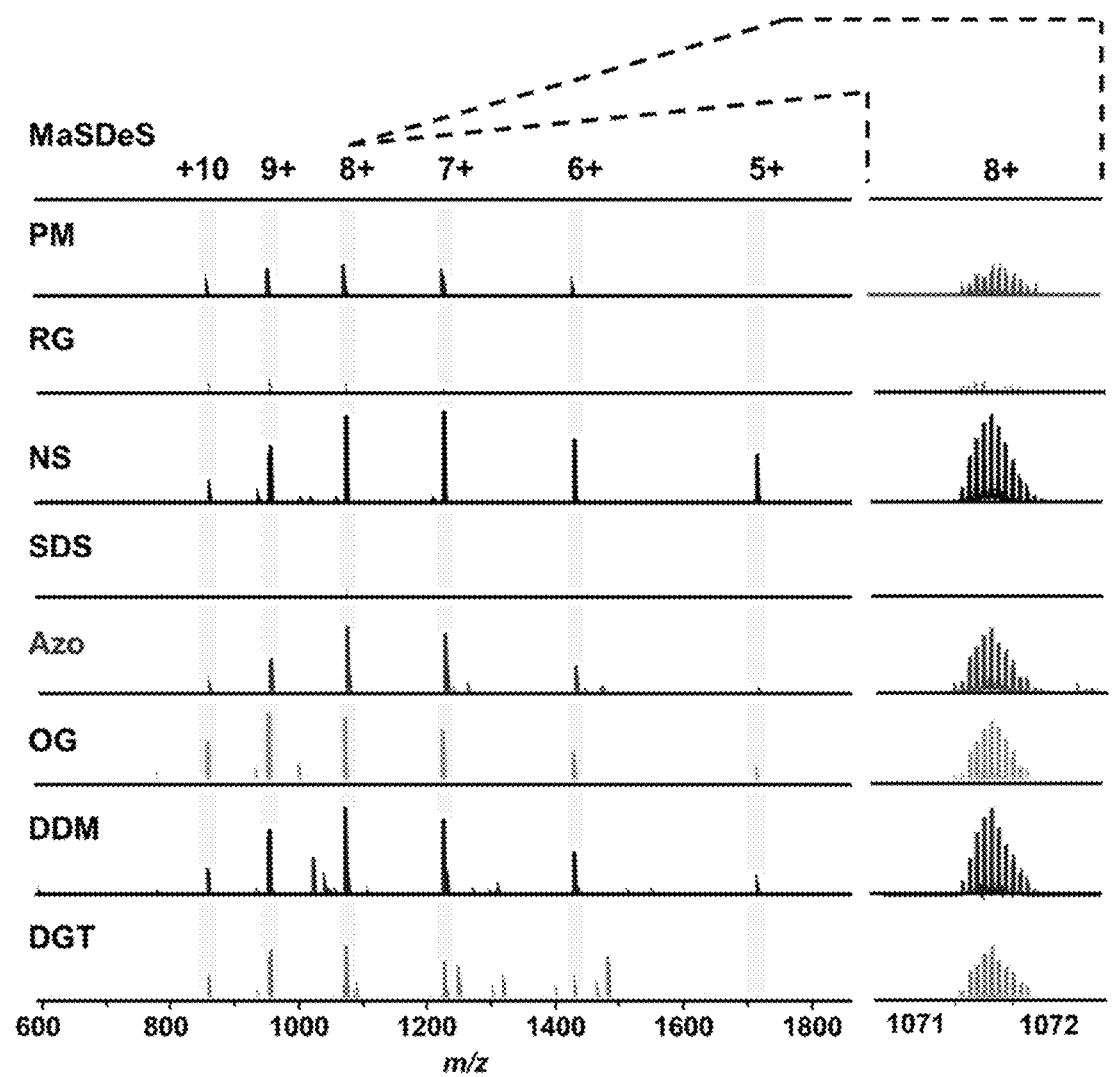
FIG. 17—MS-compatibility evaluation of Azo as compared to commonly used surfactants. 0.1% surfactant was added to ubiquitin in 25 mM $NH_4HCO_3$ solution and analyzed by high-resolution mass spectrometry and compared to controls with no surfactant (NS). Surfactants including MS-compatible slowly-degradable surfactant (MaSDeS), ProteaseMax™ (PM) 1, RapiGest™ (RG), sodium dodecyl sulfate (SDS), 4-hexylphenylazosulfonate (Azo), Octyl β-D-glucopyranoside (OG), dodecyl β-D-maltoside (DDM), and digitonin (DGT) were tested. The mass spectra were collected on a Bruker 12 T FTICR mass spectrometer and normalized to the maximum intensity in the NS (control) spectrum of 8E10.

Subsequently, a comparison of the MS-compatibility of Azo with these leading surfactants was performed (FIG. 17). The mass spectrometry analysis of Ubi in the presence of 0.1% surfactants, showed that SDS and MasDeS dramatically suppressed the MS signal of the intact Ubi, RG and PM significantly suppressed the MS signal of Ubi, whereas Azo and non-ionic surfactants, OG, DDM, and DGT showed minimal MS protein signal suppression. Noticeably, these non-ionic surfactants caused more extensive adducts as compared to Azo (FIG. 17).

Example 2—Photo-Cleavable Surfactant for Top-Down Proteomics

Figure 3:
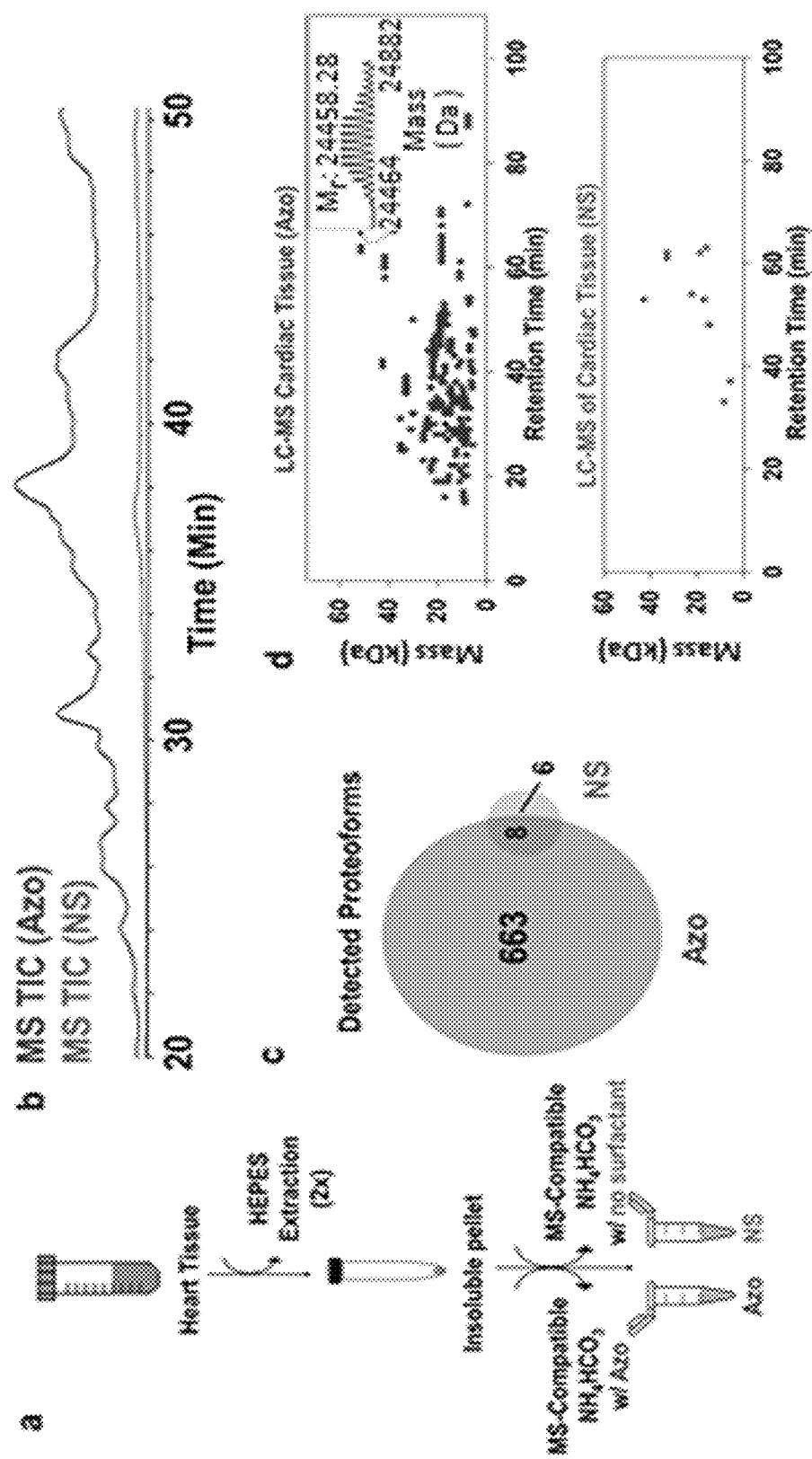
FIG. 3—Photo-cleavable Azo-enhanced top-down proteomics. Panel (a), schematic depicting sequential tissue extraction procedures. Proteins from cardiac tissue were extracted using HEPES buffer (2×) to deplete the cytosolic proteins, followed by an extraction using NH4HCO3 solution with or without 0.5% Azo. Panel (b), comparison of the total ion chromatogram (TIC) of equal injection volumes of the final cardiac extraction with or without 0.5% Azo. Panel (c), comparison of detected proteoforms in a single RPLC-MS run of proteins extracted with or without Azo. Panel (d), intact proteoform mass map from cardiac tissue extraction with Azo or without Azo (NS).
Figure 4:
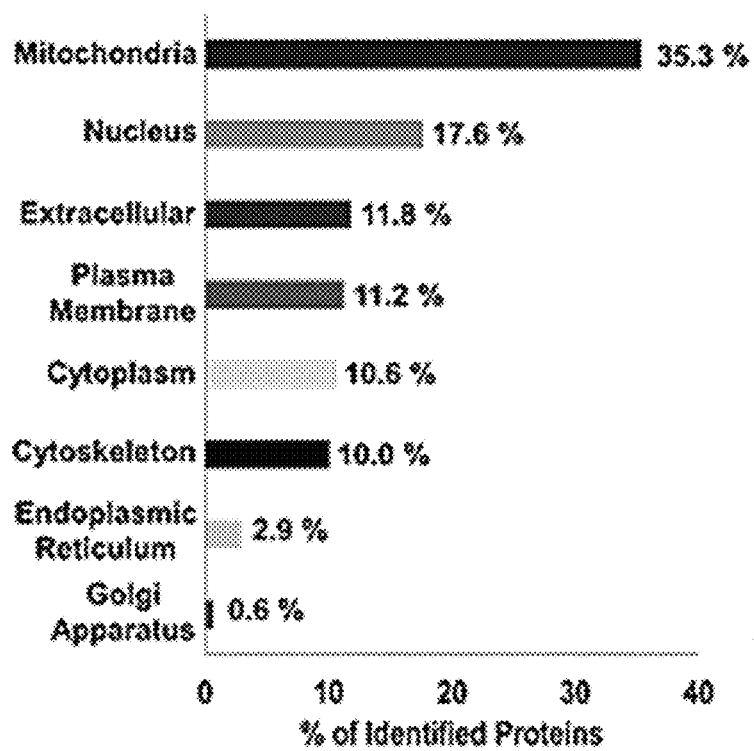
FIG. 4—Subcellular location of proteins identified in cardiac tissue in Azo-enhanced top-down proteomics combining 3 RPLC-MS/MS runs.

The utility of Azo for top-down proteomics was assessed in online RPLC-MS and RPLC-MS/MS experiments with collision-induced dissociation (CID). Water-insoluble cardiac tissue pellets were extracted with 25 mM NH4HCO3 buffer either containing 0.5% Azo, labelled as E3 (Azo), or no surfactant, served as a control and labelled as E3 (NS) (FIG. 3, panel a). Notably, both the SDS-PAGE gel (FIG. 2, panel b) and the total ion current (FIG. 3, panel b) showed significant increases in protein concentration and MS signal, respectively, with the use of Azo when compared to no surfactant (NS). Moreover, a total of 2836 proteoforms was detected based on accurate mass measurements from the combination of three LC-MS runs; among which 388 proteoforms were identified based on one-dimensional online RPLC-MS/MS data representing 171 proteins from mitochondria, nucleus, plasma membrane, cytoskeleton, endoplasmic reticulum, cytoplasm, and extracellular regions (FIG. 4).

Figure 19:
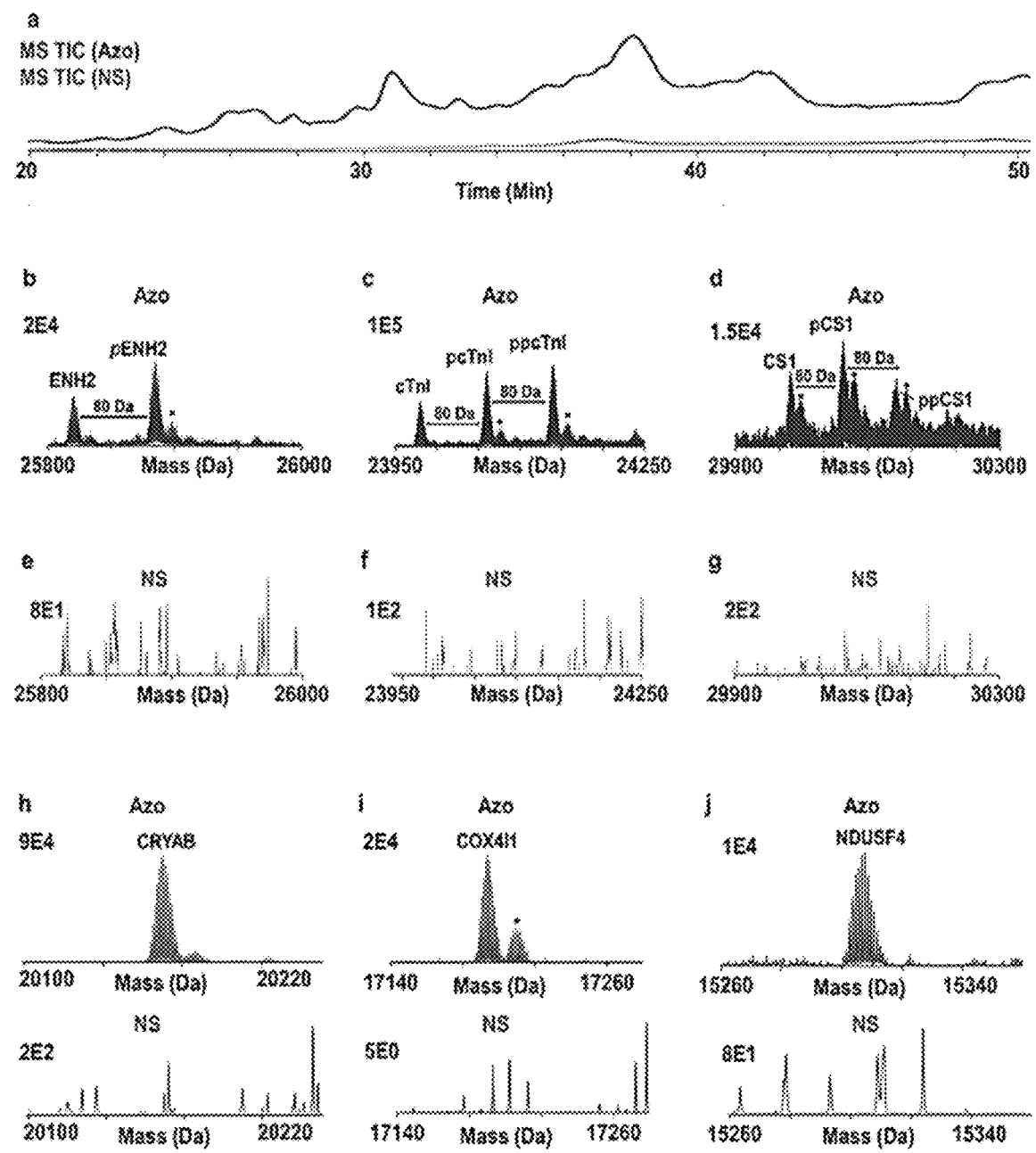
FIG. 19—Comparison of cardiac tissue extraction using MS-compatible $NH_4HCO_3$ with or without Azo in a single RPLC/MS run. Panel (a), MS total ion chromatogram with representative proteins: panel (b) enigma homolog 2 (ENH2), panel (c) troponin I (cTnI), panel (d) calsarcin-1 (CS-1), panel (h) alpha-crystallin b chain (CRYAB), panel (i) cytochrome c oxidase subunit 4 isoform 1 (COX4I1), and panel (j) NADH dehydrogenase Fe—S protein 4 (NDUSF4). These proteins were detected in the Azo-extraction but not detected in the control without Azo. Mass spectra were collected on a Bruker maXis II Q-TOF mass spectrometer. NS: no surfactant, such as in panels (e), (f), and (g) serving as controls.

Importantly, various PTMs included acetylation, methylation, phosphorylation, and palmitoylation were observed. In addition to the breadth in the increased protein identifications, Azo also greatly improved the depth of the detection and revealed many proteins that were undetectable in the control sample (FIG. 19). For example, for the first time, Azo allowed for the detection and identification of an intact calsarcin-1 (CS1; Mr 29961.98) (FIG. 19), an important Z-disk protein that was not detected in the control and not reported previously (Peng et al., Mol. Cell. Proteomics, 2014, 13:2752-2764). Moreover, multiple phosphorylated proteoforms were detected for CS1. As a negative regulator of calcineurin signaling in heart, CS1 has multiple phosphorylations that are regulated during cardiac hypertrophy (Paulsson et al., 2010, J. Mol. Cell. Cardiol., 48:1206-1214). Therefore, Azo opens up the opportunity to investigate intact CS1 and its phosphorylated proteoforms in cardiac disease.

Membrane Proteomics. Given the critical role of surfactant in the extraction and characterization of peripheral and integral membrane proteins, the effects of Azo on membrane proteomics were further evaluated. It was observed that the optimal degradation condition, with the organic solvent at low pH, also aided in the continued solubilization of hydrophobic species post-degradation. In particular, it was observed that isopropanol or a mixture of isopropanol and acetonitrile effective maintained protein solubility (both hydrophobic and hydrophilic) after degradation. Furthermore, CID fragmentation was highly efficient and favorable for the transmembrane domain portions of the proteins, leading to confident protein identification of integral membrane proteins.

Figure 5:
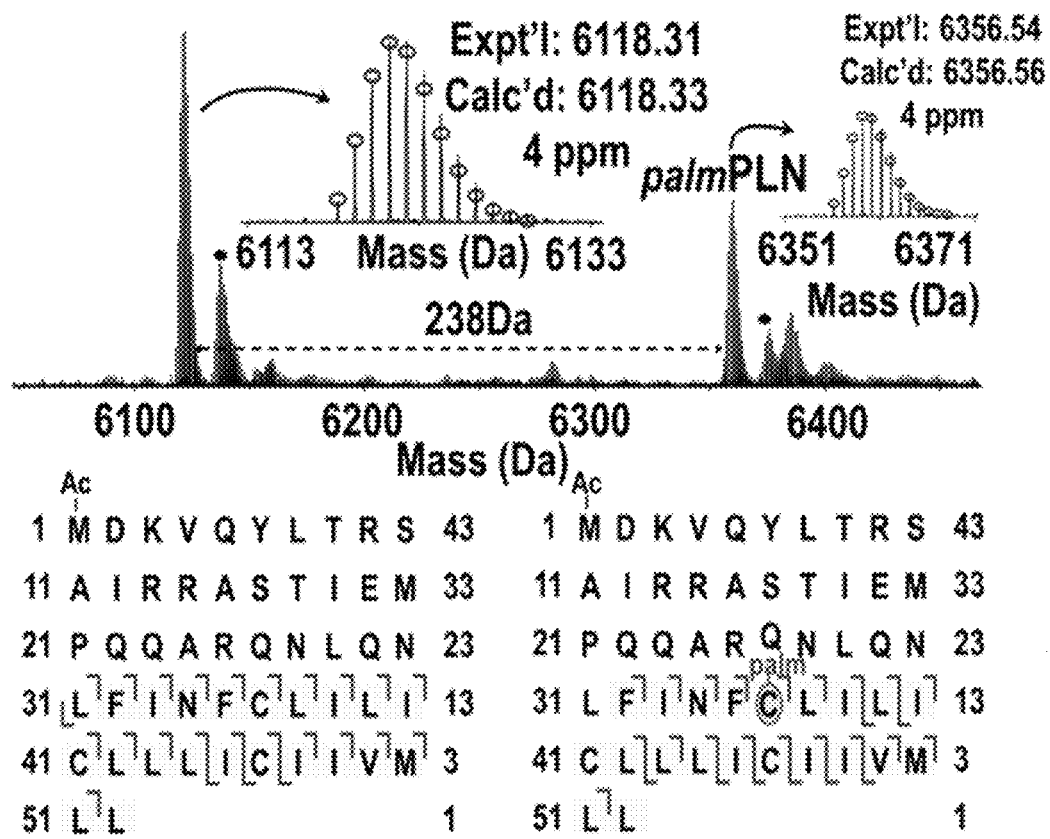
FIG. 5—Photo-cleavable Azo-enabled membrane proteomics. MS and MS/MS analysis of representative membrane proteins from Azo-aided extraction of cardiac tissue. Panel (a), phospholamban (PLN) and palmitolyated-phospholamban with palmitolyation identified at cysteine 37 residue. Panel (b), receptor expression-enhancing protein 5.
Figure 5:
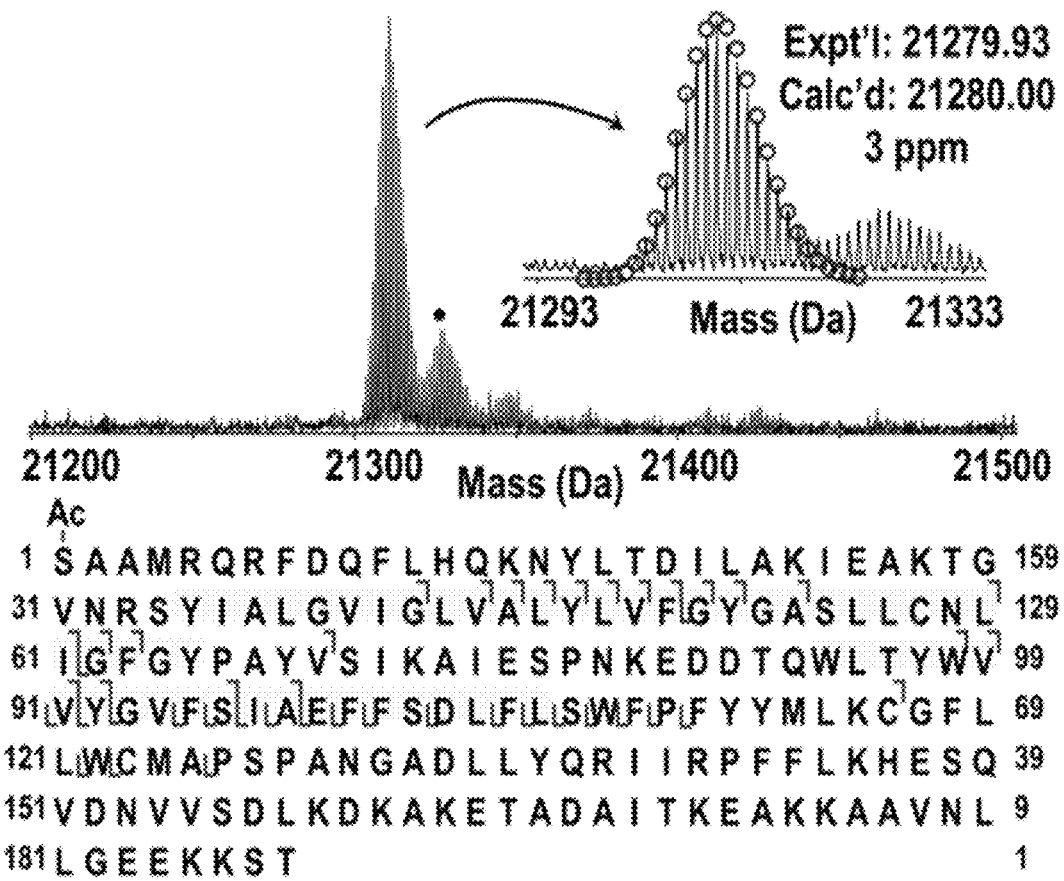
Figure 22:
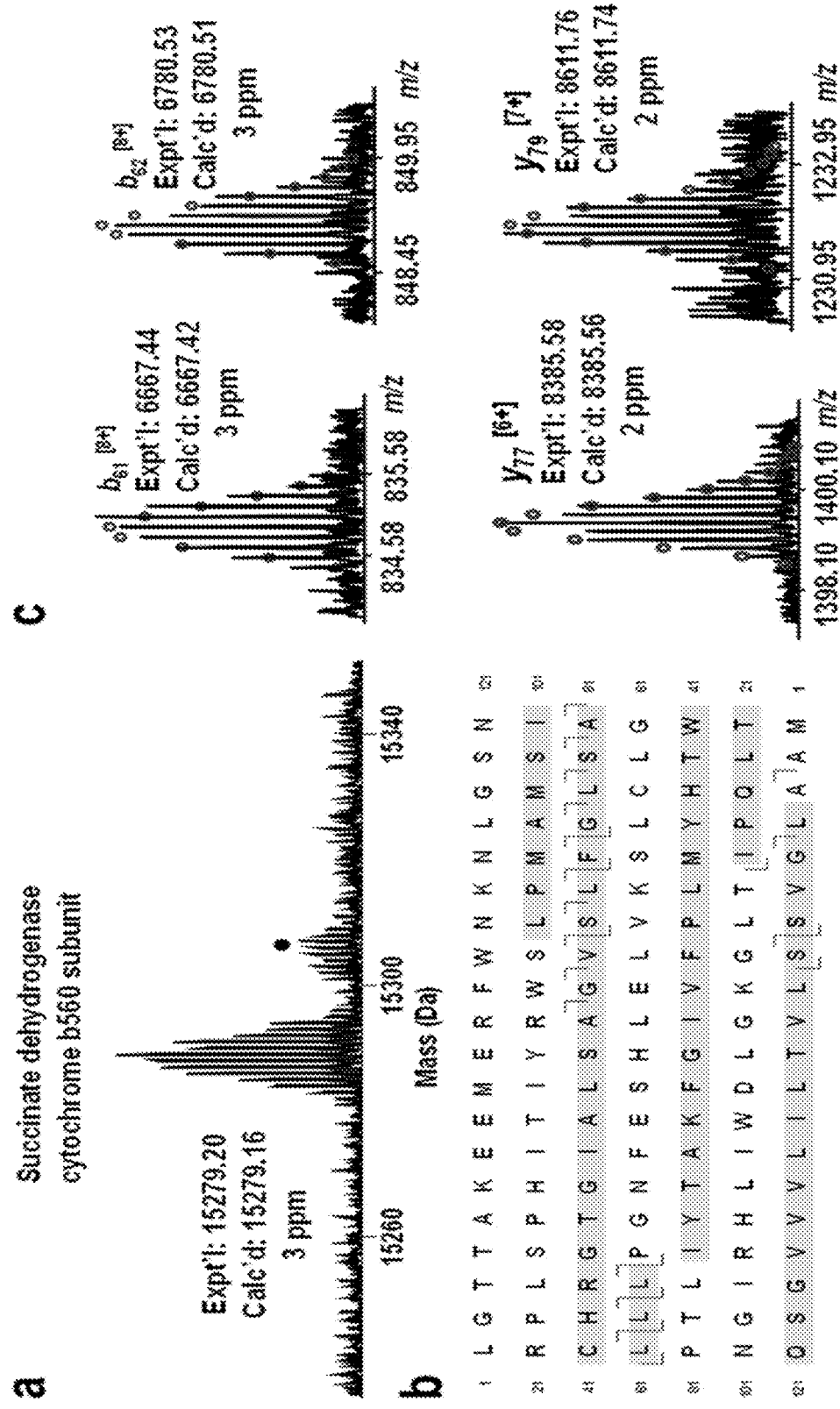
FIG. 22—Identification of succinate dehydrogenase cytochrome b560 subunit by top-down proteomics enabled by Azo. Panel (a), intact mass spectrum of succinate dehydrogenase cytochrome b560 acquired with high mass accuracy using a Bruker maxis II Q-TOF mass spectrometer. Panel (b), sequence fragmentation (CID) map. Shaded regions indicate the three transmembrane domains. Panel (c), represented fragments used to confidently identify the protein FIG. 23—Localization of palmitolyation (palm) on phospholamban (PLN) by online LC-MS/MS with CID. Panel (a), high-accuracy measurement of PLN and its highly abundant palmitoylated proteoform acquired on a Bruker maXis II Q-TOF mass spectrometer; panel (b), CID fragmentation map of both PLN and palmPLN with designated regions designating the transmembrane domain; panel (c) representative ions for the palmPLN showing the localization of the palmitolyation to the cysteine 36 residue. Circles show theoretical isotopic distribution FIG. 24—Localization of trimethylation on ATP synthase c by online LC-MS/MS with CID. Panel (a), high-accuracy measurement of ATP synthase subunit c acquired on a Bruker maxis II Q-TOF mass spectrometer; panel (b), CID fragmentation map with designated regions designating the two transmembrane domains; panel (c), representative ions measured with high mass accuracy representing the trimethylated (Me3) ATP synthase c. Circles show theoretical isotopic distribution.
Figure 23:
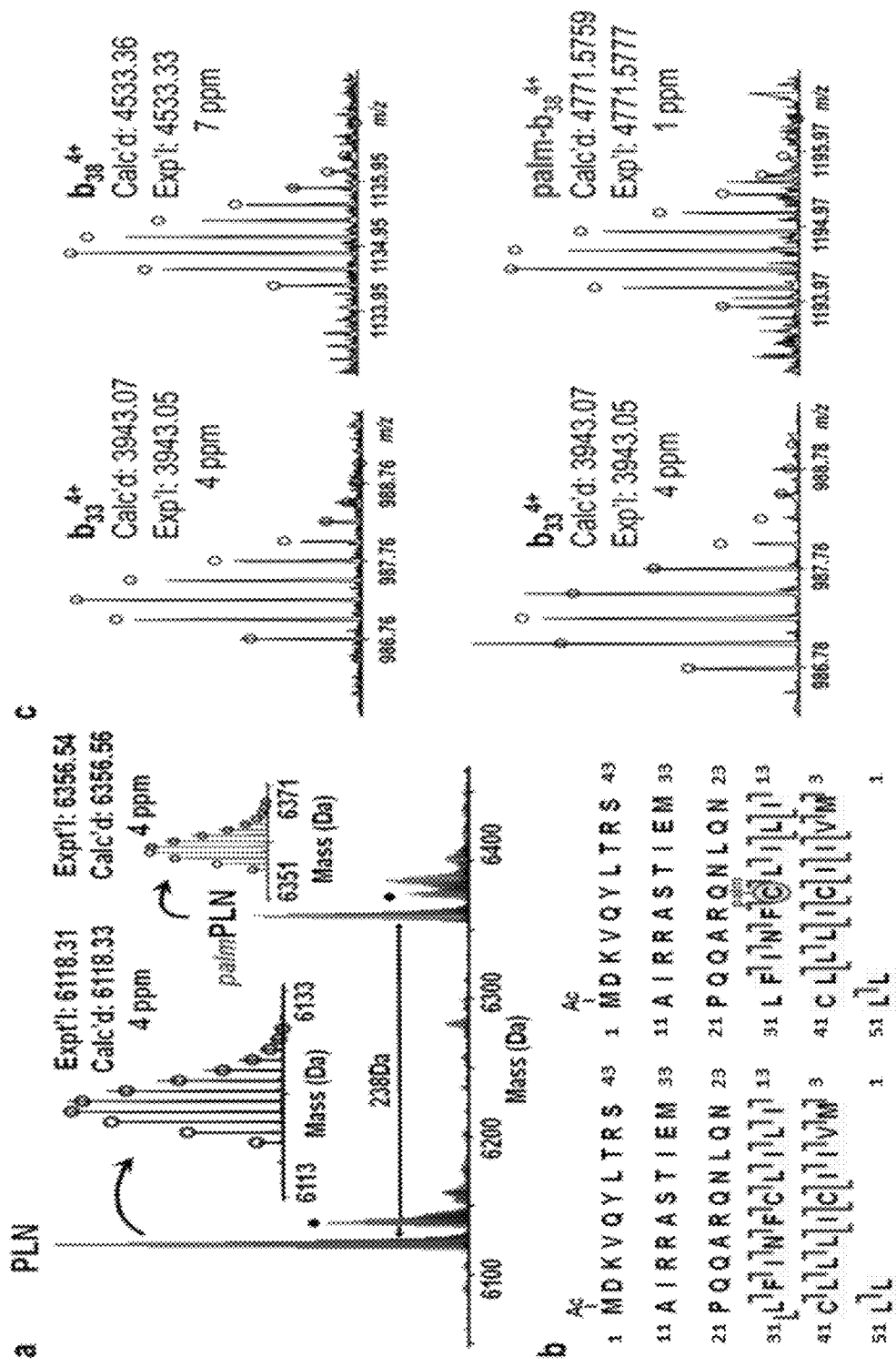

To demonstrate Azo's general applicability to membrane proteomics, a protein extraction was performed using a sarcoplasmic reticulum-mitochondria enriched sample from both cardiac tissue and Human Embryonic Kidney (HEK) 293T cells (FIGS. 5, 10 and 20). Under optimal UV-degradation conditions (which included organic solvent at low pH), many hydrophobic proteins were soluble post Azo-degradation. Using RPLC-MS, 38 subunits of the electron transport chain were identified, including 11 of the 15 ATP synthase subunits, and 18 proteins with transmembrane domains (TMD) from the cardiac tissue. A particularly intriguing integral membrane protein identified in this study was phospholamban (PLN, Mr 6,118.31 Da), receptor-expressing enhancing protein (Mr 21279.93 Da), and succinate dehydrogenase cytochrome b560 (Mr 15279.20 Da) with 1, 2, and 3 transmembrane domains (TMD), respectively (FIG. 5, panels a and b, and FIG. 22). Notably, it was detected that PLN is palmitoylated and its palmitoylated proteoform (Mr 6,356.54 Da) is highly abundant (FIG. 5). The palmitoylation modification was confidently localized to cysteine 36 within the transmembrane region based on the unmodified b33 ion and the palmitoylated b38 ion (FIG. 5, panel a, and FIG. 23). PLN is a well-known cardiac regulatory protein which has been implicated in cardiomyopathy (MacLennan et al., 2003, Nat Rev Mol Cell Biol, 4:566-577) and the palmitoylation (Zhou et al., 2015, Proc Natl Acad Sci USA, 112:15666-15671) governs its interaction with PKA and protein phosphatase 1 a. Similarly, a receptor-expressing enhancing protein was characterized and localized an acetylation site to the N-terminus (FIG. 5, panel b).

Figure 6:
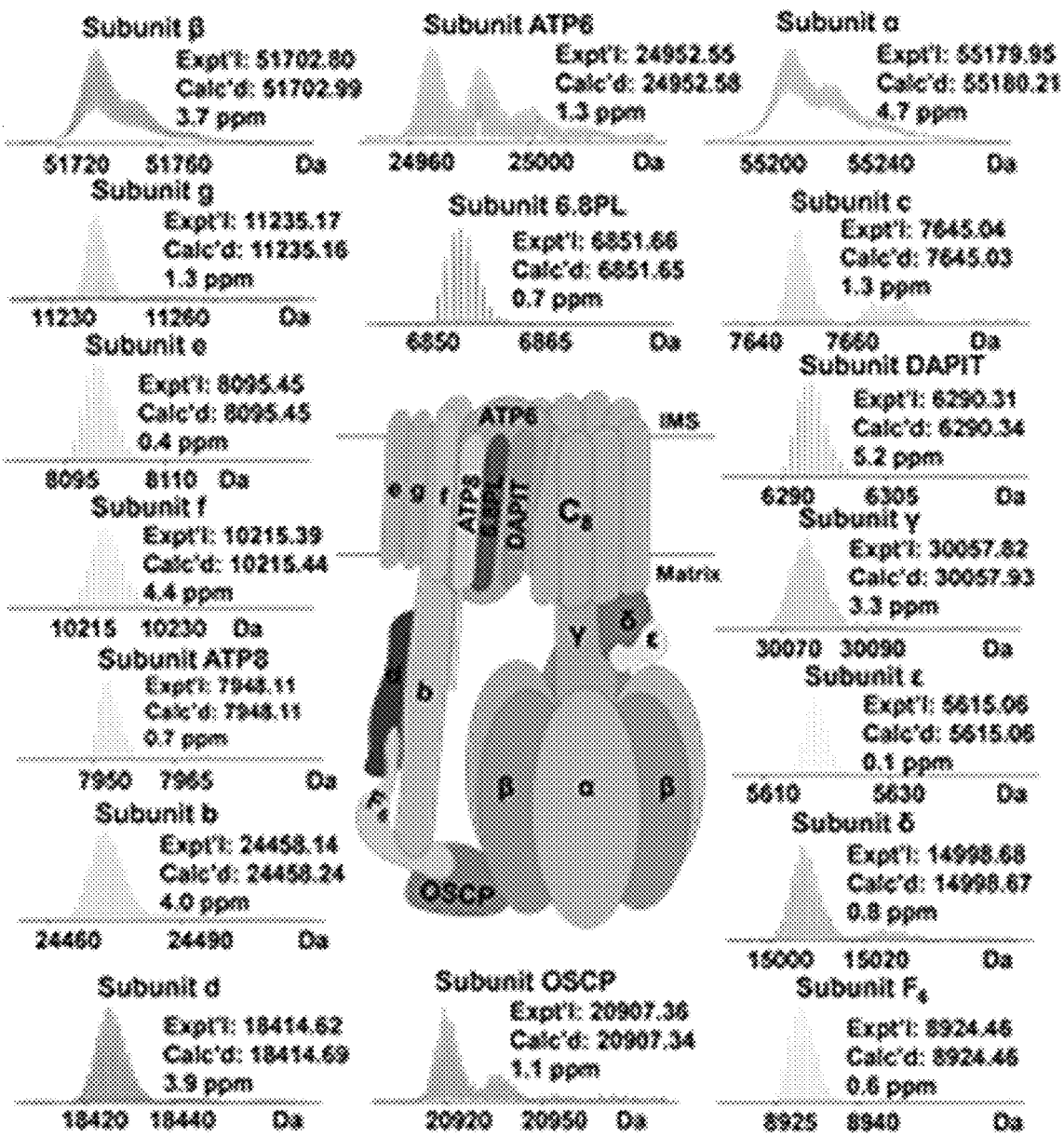
FIG. 6—Complete analysis of ATP synthase subunit proteins from cardiac tissue. Overall all the ATP synthase subunits (e, f, g, ATP6, ATP8, DAPIT, C, 6.8PL) were detected that exist in the inner membrane space (IMS) as well as the subunits (a, B, b, ¿, o, OCSP, F6, d, Y) located in the mitochondrial matrix. The schematic of ATP synthase was modified based on a previous publication by He et al. (Proc. Natl. Acad. Sci., 2018, 115 (12): 2988-2993).
Figure 24:
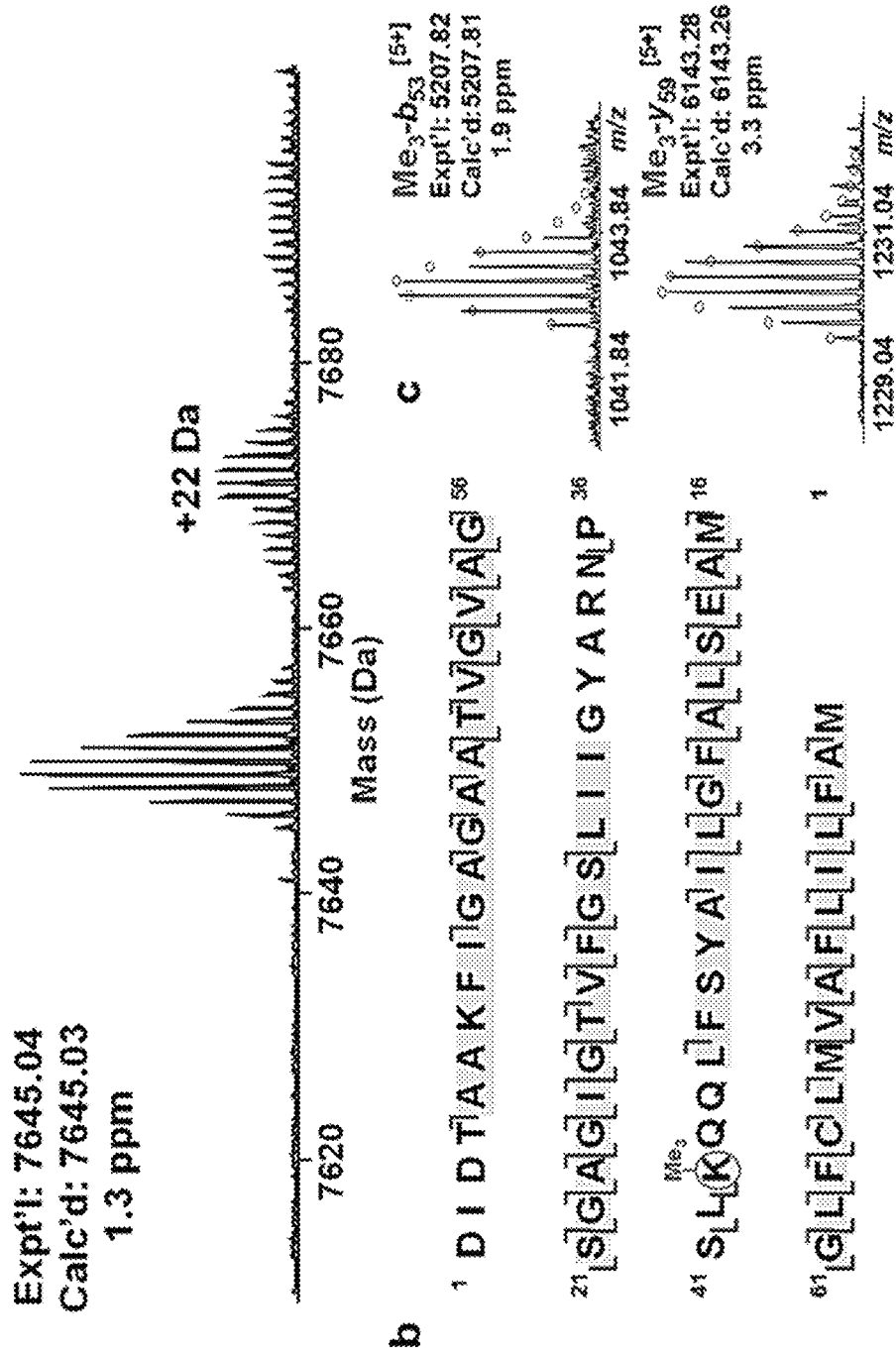

Importantly, 46 subunits of the electron transport chain were confidently identified and 51 proteins with TMDs directly from cardiac tissue. Notably, all the subunits of the ATP synthase complex can be identified with high mass accuracy directly from cardiac tissue (FIG. 6). This enzyme, which plays a critical role in biological energy metabolism (He et al., Proc. Natl. Acad. Sci., 2018, 115 (12): 2988-2993), includes a domain located in the inner mitochondrial membrane (IMS) (e, f, g, ATP6, ATP8, DAPIT, c, 6.8PL) as well as a domain in the mitochondrial matrix (a, B, b, E, o, OCSP, F6, d, y). In particular, Azo facilitated the identification of ATP6 (also known as ATP synthase subunit a; Mr 24952.55) with 6 TMD as well as the localization (lysine 43) of a highly conserved trimethylation between 2 TMD of ATP synthase subunit c (Mr 7645.04 Da) (FIG. 24). The trimethylation was speculated to provide site-specific binding for cardiolipin (Walpole et al., 2015, Mol. Cell. Proteomics, 14:828-840). Besides the small and intermediate size subunits (<30 kDa), the high molecular weight (>50 kDa) ATP synthase subunits were able to be detected and identified: ATP synthase a (Mr 55179.95 Da) and B (Mr 51702.80 Da) with the help of Azo (FIG. 6). Highly efficient CID fragmentation was observed which preferentially cleaved in the transmembrane domain portions of the proteins (FIG. 5, panels a and b, and FIGS. 22-24), leading to confident protein identification of these integral membrane proteins and localization of PTMs in online RPLC-MS/MS experiments. Thus, Azo was able to enable the detection and comprehensive characterization of these important cardiac membrane protein complexes, which opens up new opportunities to uncover their molecular basis in health and disease.

Materials and reagents. All chemicals and reagents were used as received without further purification unless otherwise noted. Sodium nitrate (NaNO3), sodium sulfite (Na2SO₃), 4-nitrophenyl chloroformate, sodium carbonate, 4-n-hexylaniline, 4-n-octylaniline, 4-n-decylaniline, 4-n-dodecylaniline, N-(3-Dimethylaminopropyl)-N'-ethylcarbodiimide hydrochloride (EDC), 4-(bromomethyl)-3-nitrobenzoic acid, octylamine, decylamine, dodecylamine, N-ethyldiisopropylamine (EDIPA), piperidine, 1,4-butanesultone, and anhydrous N,N-dimethylforamide (DMF) N,N,N',N'-Tetramethyl-O-(1H-benzotriazol-1-yl) uronium hexafluorophosphate (HBTU) and dinitrophenylhydrazine (DNP) were obtained from TCI America (Portland, OR, USA). Fmoc-photolabile linker was purchased from Advanced Chemtech (Louisville, KY, USA). Tetrahydrofuran (THF), ammonium hydroxide (NH₄OH), dichloromethane, heptane, acetone, trimethylamine (Et₃N), magnesium sulfate (MgSO₄), sodium carbonate and silica were purchased from Sigma-Aldrich Inc. (St. Louis, MO, USA).

Extraction solutions were made in nanopure deionized (DI) Water (H₂O) from Milli-Q water (Millipore, Corp., Billerica, MA, USA). HEPES, ammonium bicarbonate (NH₄HCO₃), sucrose, sodium fluoride (NaF), phenylmethanesulfonyl fluoride (PMSF), ethylenediaminetetraacetic acid (EDTA), n-dodecyl β-D-maltoside (DDM), octyl β-D-glucopyranoside (OG), sodium dodecyl sulfate (SDS), digitonin (DGT), protease inhibitor cocktail, tri (2-carboxyethyl) phosphine hydrochloride (TCEP), dithiothreitol (DTT), 2-mercaptoethanol (2-ME), ubiquitin from bovine erythrocytes (Ubi), bovine serum albumin (BSA), myoglobin from equine heart (Myo) and cytochrome C (Cytc) from equine heart, ribonuclease A (RNase A) and ribonuclease B (RNaseB) from bovine pancreas were purchased from Sigma-Aldrich Inc. (St. Louis, MO, USA). ProteaseMax™ (PM) was obtained from Promega (Fitchburg, WI, USA). RapiGest™ (RG) was purchased from waters (Milford, MA, USA). Sodium orthovanadate, HPLC grade H₂O, acetonitrile (ACN), methanol (MeOH), ethanol (EtOH), optima LC-MS grade formic acid, optima LC-MS grade isopropanol (IPA), Pierce protein-free tris-buffered saline (TBS) blocking buffer, tween 20, and 10 kDa molecular weight cutoff (MWCO) (0.5 mL) centrifugal filters, Coomassie blue R-250, and Dulbecco's modified eagle medium (DMEM) were purchased from Fisher Scientific (Waltham, MA). Fetal bovine serum (FBS) was purchased from Life Technologies (Carlsbad, CA). Mini-gels (12.5%) for SDS polyacrylamide gel electrophoresis (SDS-PAGE) were prepared in house. MS-compatible degradable surfactant (MasDeS) was synthesized by Promega and provided to us as a gift as described previously (Chang et al., 2015, J Proteome Res, 14 (3): 1587-99).

Synthesis of O-Nitrobenzyl (ONB) Surfactant Family

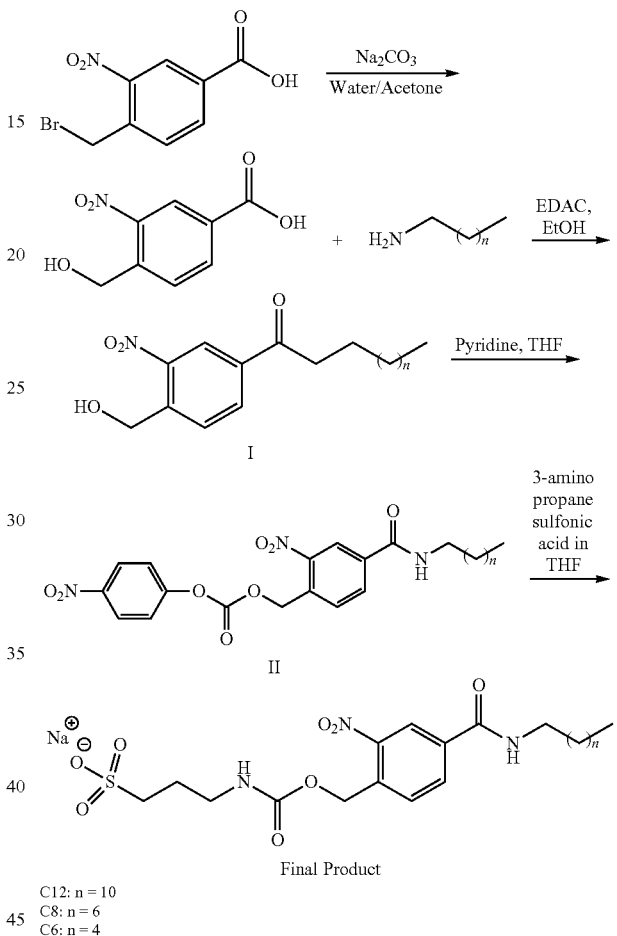

Synthesis of 4-(hydroxyethyl)-3-nitrobenzoic acid. A solution of 500 mg of 4-(bromomethyl)-3-nitrobenzoic acid (1.92 mmol) and 814 mg of Na₂CO₃ (7.68 mmol) in 16 mL of a mixture of H₂O/acetone 1:1 (v/v) was refluxed for 5 h. The acetone was then evaporated and the resulting solution was washed with 9 mL of diethyl ether. After the wash, the solution was acidified with 18% hydrochloric acid until a precipitate was observed. The product was then extracted with ethyl acetate (3×12 mL). The concentrated organic layer was washed with H₂O (6 mL) and dried over MgSO₄. The dry organic layer was filtered and concentrated in vacuo to yield 74% of 4-(hydroxyethyl)-3-nitrobenzoic acid as a yellow solid.

Synthesis of intermediate product I (n=10, C12) (Scheme 1). Using a traditional EDC coupling, 270 mg of 4-(hydroxyethyl)-3-nitrobenzoic acid (1.37 mmol) was reacted with 0.32 mL of dodecylamine (1.37 mmol) to produce 1 (n=10, C12) in a 44% yield.

Synthesis of intermediate product I (n=6, C8) (Scheme 1). Using a traditional EDC coupling, 300 mg of 4-(hydroxyethyl)-3-nitrobenzoic acid (1.52 mmol) was reacted with 0.25 mL of octylamine (1.37 mmol) to produce 1 (n=6, C8) in a 19.3% yield.

Synthesis of intermediate product I (n=4, C6) (Scheme 1). Using a traditional EDC coupling, 300 mg of 4-(hydroxy-ethyl)-3-nitrobenzoic acid (1.52 mmol) was reacted with 0.20 ml of hexylamine (1.37 mmol) to produce 1 (n=4, C6) in a 46% yield.

Synthesis of intermediate product IIs (Scheme 1). 7.7 mmol of each intermediate product I was dissolved in 40 mL of THF and the solution was cooled to 0° C. While stirring 4-nitrophenyl, chloroformate was slowly added to the THF solution. Then 0.162 mL of pyridine was added dropwise over 20 min and the reaction was stirred for an additional 2 h. The reaction was then filtered. The final product was purified using a silica column that was packed using a solvent of 7:3 ration of heptane: EtOH and an eluting solvent of a ratio of 4:1 heptane: EtOH.

Synthesis of ONB final product (Scheme 1). 0.13 mmol of intermediate product II was dissolved in 2.3 mL of THF. In a separate container, 0.20 mmols of 3-aminopropane sulfonic acid sodium salt in 0.43 mL of water was added to the THE solution. The reaction was stirred overnight at 50° C. The product was purified using a silica column with a mixture of dichloromethane: MeOH (1:5). The final product was confirmed by mass spectrometry: ONB C12 ($C_{24}H_{38}N_3O_8SNa$), $[M-Na+H+NH_4]^+$: calculated m/z: 547.6, observed m/z: 547.3; ONB $C_8$ ($C_{20}H_{30}N_3O_8SNa$), $[M-Na+H+NH_4]^+$: calculated m/z: 491.5, observed m/z: 491.3; ONB $C_6$ ($C_{18}H_{26}N_3O_8SNa$), $[M-Na+H+NH_4]^+$ calculated m/z: 463.5, observed m/z: 463.3.

Synthesis of O-nitroveratryl (ONV) Surfactant Family.

Scheme 2. Synthesis of O-nitroveratryl (ONV) Surfactant Family.

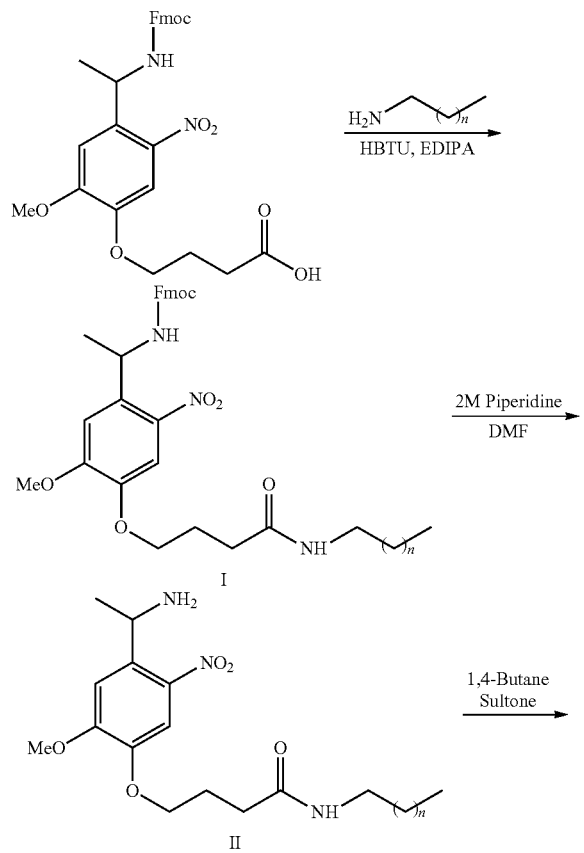

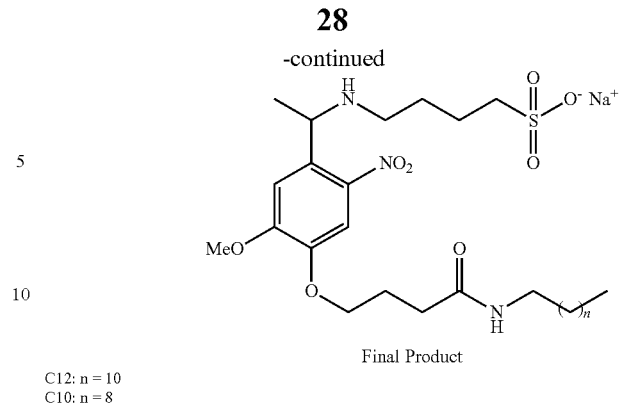

Final Product

C12: n = 10
C10: n = 8
C8: n = 6

The ONV surfactants were synthesized following previously reported procedures (Hwang et al., 2016, Langmuir, 32 (16): 3963-9). Briefly, to a solution of Fmoc-ONV—COOH (0.57 mmol) and HBTU (0.69 mmol) in 3.5 mL of anhydrous DMF, EDIPA (1.15 mmol) was added drop wise. The solution was cooled on ice and added to a solution of dodecylamine in 0.5 mL of ice-cold EtOH. After stirring for 30 min at 0° C., the mixture was stirred overnight at room temperature (RT). The resulting precipitate was filtered and washed with DMF followed by in vacuo drying. Intermediate product I (n=10, $C_{12}$) was obtained as an amorphous white powder. Similar procedure were followed for n=8, $C_{10}$ and n=6, $C_8$ (Scheme 2).

Synthesis of $NH_2$—ONV—$CH_2$ ($CH_2$) n $CH_3$ (Intermediate product II) (Scheme 2). Piperidine was added dropwise to a solution of intermediate product I (0.6 mmol) in anhydrous DMF (3 mL) to reach a final concentration of 2 M. The solution was stirred at RT for 2 h, and then DMF was removed by evaporation. The residual was dissolved in MeOH and the resulting precipitate was removed by filtration. A pale yellow solid was obtained after evaporation of the filtered solution.

Synthesis of Sulfonate-ONV—$CH_2$ ($CH_2$) n $CH_3$ (Final product) (Scheme 2). 1,4-butanesultone (2.1 eq, 0.74 mmol) was added to a solution of intermediate product II (1.0 eq, 0.35 mmol) with $Et_3N$ (2.0 eq) in ACN (2 mL) and then the flask was sealed. The mixture was stirred and heated to ~90° C. for 48 h. After removing the solvent by evaporation, a light yellow viscous oil was obtained quantitatively. The oil was suspended in water and a $NH_4OH$ (aq) solution was added dropwise until pH ~8 was reached. The surfactant solutions were centrifuged. The final product was confirmed by ESI-MS. ONV $C_{12}$ ($C_{29}H_{50}N_3O_8SNa$), [M−Na], calculated m/z: 600.3, observed m/z: 600.3; ONV $C_{10}$ ($C_{27}H_{46}N_3O_8SNa$), [M−Na], calculated m/z: 572.3, observed m/z: 572.2. ONV $C_8$ ($C_{25}H_{42}N_3O_8SNa$), [M−Na], calculated m/z: 544.3, observed m/z: 544.2.

Synthesis of the Azobenzene (AZO) Surfactant Family.

Scheme 3. Synthesis of the AZO Surfactant Family.

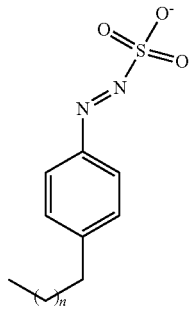

C12: n = 10
C10: n = 8
C8: n = 6
C6: n = 4

The AZO surfactant family was synthesized following similar procedures as previously described (Mezger et al., 1996, Progress in Organic Coatings, 29 (1): 147-157). Specifically, 4 mmol of 4-n-hexylaniline (n=4, C=6) was stirred in a mixture of 4.8 mL of 10% hydrochloric acid and 8 mL of DI $H_2O$. Then 4 mmol of $NaNO_2$, dissolved in 4 mL of cold water, was added dropwise to this solution. During the addition of the $NaNO_2$ the solution was cooled to 10° C. After the addition was completed (15 min), the solution was stirred for an additional 15 min at 5° C. A similar procedure was carried out for 4-n-octylanilin (n=6, $C_8$). For 4-n-decylaniline (n=8, $C_{10}$) and 4-n-dodecylaniline (n=10, $C_{12}$), the solution of 4-n-alkylaniline was heated to 70° C. and then cooled in an ice bath to 10° C. under vigorous stirring.

$NaNO_2$ was added dropwise starting at 20° C. and concluded at 10° C., followed by 15 min of stirring at 5° C. For the coupling reaction, the freshly prepared diazonium salt was filtered into a stirring and cooled solution (T=5-10° C.) of 8 mmol of $Na_2SO_3$ and 12 mmol of $Na_2CO_3$ in 20 mL of DI $H_2O$. To complete the precipitation of the surfactant, the solution was refrigerated at 4° C. overnight. The yellow compounds were purified by recrystallization with a yield about 50% and no impurities were detected by NMR. Surfactant solutions were made by gently heating the surfactant at 37° C. then bringing to room temperature after no solid remained. Working concentration were 0.5%-1% in 25 mM $NH_4HCO_3$. Kraft temperature (a clear 1% surfactant solution) was previously reported at 24.5° C. (Cravatt et al., 2007, Nature, 450:991).

A high-resolution mass spectrum of 4-hexylphenylazosulfonate ("Azo") (FIG. 7) was taken as follows: A solution of 1% Azo in 25 mM $NH_4HCO_3$ was diluted 1:100 in ACN (0.3% $NH_4OH$). The sample was directly injected into a 7 T linear ion trap/Fourier transform ion cyclotron resonance (LTQ/FT-ICR) mass spectrometer (LTQ/FT Ultra, Thermo Scientific, Bremen, Germany) with a nano-electrospray ionization (ESI) source (Triversa NanoMate; Advion Bioscience, Ithaca, NY). A voltage of −1.4 kV was applied with 0.3 psi drying gas. Fifty scans were averaged with 5 microscans in a scan. The mass range was set from 100 to 500 m/z. A mass of 269.098 Da was observed which corresponds to the predicted molecular weight (269.096 Da) for this compound using the Isopro software (Yergey et al., 1983, International Journal of Mass Spectrometry and Ion Physics, 52 (2): 337-349).

TABLE 1

Protein solubility screening of a library of photo-cleavable surfactants.

| Surfactant | | | Water Solubility at RT | Protein Solubility |
|---|---|---|---|---|
| ONB | C6 | | Slightly Soluble | Poor |
| | C8 | | Relatively Insoluble | Poor |
| | C12 | | Relatively Insoluble | Poor |
| ONV | C8 | | Soluble | Fair |
| | C10 | | Soluble | Poor |
| | C12 | | Soluble | Poor |
| AZO | C6 | | Soluble | Good |
| | C8 | | Soluble | Fair |
| | C10 | | Slightly Soluble | Poor |
| | C12 | | Slightly Soluble | Poor |

Surfactants with o-nitrobenzyl (ONB), o-nitroveratryl (ONV), and azobenzene (AZO) cleavable groups were synthesized with varied chain lengths from 6-14 carbons (C=6-14). Each synthesized surfactant was evaluated for its solubility in water first. Next the surfactants were used to solubilize swine heart proteins after HEPES buffer was used to deplete the water-soluble species. Overall Azo (C=6) was the only surfactant which not only has excellent solubility in water but can effectively solubilize proteins.

Protein extraction. Pig hearts were excised from healthy Yorkshire domestic pigs, snap-frozen in liquid $N_2$, and stored under $-80°$ C. before use, which was approved by the University of Wisconsin Animal Care and Use Committee. All homogenization and centrifugation steps were performed at 4° C.

Protein extraction from cardiac tissue. The frozen tissue samples (~500 mg) were cut into small pieces and washed with PBS buffer containing protease inhibitors and reducing agent (5 mM DTT, 1 mM PMSF, 1× protease inhibitor cocktail). The tissue was then homogenized in HEPES buffer (25 mM HEPES, 250 mM sucrose, 50 mM NaF, 1 mM PMSF, 2.5 mM EDTA, 1 mM $Na_3VO_4$, 1 mM PMSF, 5 mM DTT, 1× protease inhibitor cocktail) with a Polytron electric homogenizer (model PRO200, Pro scientific, Oxford, CT) set to the lowest speed as described previously (Chang et al., 2015, J Proteome Res, 14 (3): 1587-99). The homogenate was centrifuged at 211,750×g using Beckman Ultracentrifuge and a Ti-80 rotor for 1 h. The supernatant after the first HEPES extraction was removed and saved as "E1" extraction. The HEPES extraction was repeated on the resulting pellet and saved as "E2". After the second HEPES extraction, the tissue pellet was suspended in 25 mM $NH_4HCO_3$ and evenly divided into smaller aliquots. In one aliquot, 25 mM $NH_4HCO_3$ buffer with no surfactant (NS) was used in a 1:1 ratio (homogenate: buffer) and labeled as "E3". In the other aliquots, surfactants (1% in 25 mM $NH_4HCO_3$) were individually added to the other aliquots in a 1:1 ratio (homogenate: surfactant) and labeled as "E3" following incubation and centrifugation. Protein assays were performed using Pierce 660 nm Protein Assay Reagent with Ionic Detergent Compatibility Reagent for data presented in (FIG. 2, panel c) and BioRad Bradford assay (BioRad) with detergent compatibility (compatible with 0.1% SDS) for data presented in FIG. 16.

Sarcoplasmic reticulum (SR) and mitochondria (Mit) enrichment from cardiac tissue. After cutting around 170 mg of tissue into small pieces, the tissue was homogenized in HEPES buffer (50 mM HEPES, 0.6 M KCl, 250 mM Sucrose, 500 mM NaF, 1 mM PMSF, 2 mM EDTA, 1 mM $Na_3VO_4$, 5 mM DTT, 25 µg/mL DGT, 1× protease inhibitor cocktail) with a Polytron electric homogenizer set to the lowest speed (tissue) to deplete soluble proteins as described previously (Wientzek et al., 1991, Journal of molecular and cellular cardiology, 23 (10): 1149-63). The homogenate was centrifuged at 20,000×g using a Thermo Scientific Legend Micro 21R Ultracentrifuge. The supernatant was removed and labeled as "E1". The pellet was suspended in buffer 2 (25 mM $NH_4HCO_3$, 500 mM NaF, 1 mM PMSF, 2 mM EDTA, 1 mM $Na_3VO_3$, 5 mM DTT, 25 µg/mL digitonin, 1× protease inhibitor cocktail) to remove residual proteins and labeled as "E2". The resulting tissue pellet was suspended in 25 mM $NH_4HCO_3$ and evenly divided into smaller aliquots, centrifuged at 20,000×g, and the supernatant was removed. 25 mM $NH_4HCO_3$ buffer (NS) or 1% Azo in 25 mM $NH_4HCO_3$ was added to the aliquots respectively. After incubation, the samples were centrifuged and the supernatant was collected.

50 L of enriched sarcoplasmic reticulum and mitochondria lysate from cardiac tissue was diluted with 440 µL of 50:48.5:1: 0.5 IPA: $H_2O$: formic acid: HFIP and 10 µL of TCEP (1 M). The sample was irradiated for 3 min and concentrated to a final volume of 150 pL MWCO (10 kDa in run 1 or 30 kDa in run 2). Proteins were separated using the following gradient: 0-1 min 5% B, 1-5 min 5-30% B, 5-55 min 30-60% B, 55-57 min 60-95% B, 57-65 min 95% B, 65-67 min 95% B, 67-80 min 5% B. Column temperature was 35° C. For ATP synthase subunit a, a single charge state was isolated and fragmented with 5, 10, 16, 18, 20 eV, respectively, using an isolation window of 3 m/z during targeted CID MS/MS experiments.

Sarcoplasmic reticulum (SR) and mitochondria (Mit) enrichment from cardiac tissue from human embryonic kidney (HEK) 293T cells. Cells were grown on 10 cm plates in DMEM with 10% fetal bovine serum and 1× penicillin/streptomycin solution at 37° C. and 5% $CO_2$. Cells, washed twice the PBS, from two 10 cm plates were lysed in 500 µL of buffer (10 mM Tris, 2 mM DTT, 1 mM PMSF, 50 µg/mL DGT, 1× protease inhibitor cocktail) using 50 strokes with dounce homogenizer followed by 5 passages through a 27 G needle. Cells were incubated for 10 min on ice, evenly divided into two aliquots, and centrifuged at 1,000×g (4° C.) to remove unbroken cells and the nuclei. The supernatant was mixed with 0.5 mL of sucrose (50%) and centrifuged at 21,000×g (4° C.). The pellet was washed with 1 mL of $NH_4HCO_3$ (E2). Finally, the pellets were dissolved in 100 µL of Azo (0.5% in 25 mM $NH_4HCO_3$) or 100 µL of 25 mM $NH_4HCO_3$ (NS).

50 µL of enriched endoplasmic reticulum and mitochondria lysate from HEK cells was diluted with 400 µL of 50% IPA: 49% $H_2O$: 1% formic acid and 50 µL of TCEP (1M). The sample was irradiated for 3 min then concentrated and exchanged into 10:10:80 ACN: IPA: 1% formic acid in $H_2O$ with a 10 kDa MWCO centrifugal filter. Protein were separated using the following gradient: 0-5 min 20% B, 5-65 min 20-95% B, 65-75 min 95% B, 75-76 min 20% B, 76-80 min 20% B. Column temperature was 50° C.

Whole Cell Protein Extraction from HEK 293T Cells. Cells from one 10 cm plate were washed and harvested in PBS. 200 µL of Azo (1% in 25 mM $NH_4HCO_3$) was added with 5 mM TCEP, and 1× protease inhibitor cocktail. The cells were incubated on ice and 200 µL of 25 mM $NH_4HCO_3$ was added with 500 U of benzonase. The samples were centrifuged at 16,000×g and the supernatant was collected.

Cytosolic Protein Extraction from Cardiac tissue. 10 volumes of buffer (10 mM Tris, 500 mM NaF, 2 mM EDTA, 1 mM PMSF, 1 mM $Na_3VO_4$, 5 mM DTT) was added to swine heart tissue. The sample was homogenized with Teflon homogenizer, centrifuged at 16,000×g, and the supernatant was collected. Protein extract was diluted to a final buffer containing 25% IPA, 25% ACN, 1% formic acid, 100 mM TCEP, and 5 mM $NH_4HCO_3$ with or without 0.2% Azo. The sample was irradiated for 3 min and exchanged into a 10% ACN, 10% IPA, with 0.2% formic acid using a 10 kDa MWCO centrifugal filter. Protein were separated using the following gradient: 0-5 min 20% B, 5-30 min 20-65% B, 30-35 min 65% B, 35-36 min 20% B, 36-40 min 20% B. Column temperature was 60° C.

Protein extraction from swine cardiac tissue for surfactant LC-MS comparison. 83.3 mg of swine cardiac tissue was homogenized in 1 mL of buffer (25 mM $NH_4HCO_3$, 1 mM TCEP, and 1 mM PMSF). After centifugation at 16,000×g the supernatant was collected and the protein concentration adjusted to 2 mg/mL.

SDS-PAGE comparing Azo with SDS, DDM and MaS-DeS. An equal volume (7 uL) of each extraction was subsequently resolved using 12.5% SDS-PAGE with a voltage of 50 V for 30 min and 120 V for approximately 75 min. Proteins were visualized using Coomassie Brilliant Blue R-250.

Western blot comparing Azo with SDS, DDM and MaS-DeS. Equal volumes of tissue lysate (10 uL) were loaded and resolved on 12.5% SDSPAGE gels. Proteins were transferred to a PVDF membrane, fast semi-dry blotter (Fisher-Scientific, Waltham, MA), using 20 V for 12 h at 4° C. The membrane was placed in a protein-free blocking buffer (Fisher Scientific, Waltham, MA) for 1 hour at RT and incubated with primary antibodies for 1.5 h at RT. The membranes were then washed by using TBS with 0.1% tween five times before incubation with the secondary antibodies for 1.5 h (RT). After 5 washes with TBS with 0.1% tween, the membranes were developed using enhanced chemiluminescence detection (Fisher Scientific, Waltham, MA).

UV-Vis degradation. 50 µL of 0.05% Azo in (a) $H_2O$, (b) 1% formic acid, (c) IPA, (d) 1% formic in IPA, (e) 2-ME in $H_2O$, and (f) 1% formic acid in IPA: $H_2O$, respectively, were irradiated with 100 W high pressure mercury lamp (Nikon housing with Nikon HB-10101AF power supply; Nikon, Tokyo, Japan) for 0, 10, 30, 60, 90, and 120 seconds in a quartz cuvette. The samples were diluted to a final volume of 1 mL in $H_2O$. A UV-Vis spectrum was taken from each sample with a Varian Cary 50 UV-Visible spectrophotometer (background correction, medium scan rate, 600-200 nm).

Evaluation of surfactant mass spectrometry compatibility. Ubi was dissolved in buffer containing 80:14.9:5:0.1 IPA: $H_2O$: formic acid: 0.1% surfactant (Azo, SDS, DDM, or MaSDes) with 10 mM DTT. The Azo sample was irradiated for 1 min. The MaSDes sample was degraded for 24 h at RT. The samples were then directly injected into a 7 T linear ion trap/Fourier transform ion cyclotron resonance (LTQ/FT-ICR) mass spectrometer (LTQ/FT Ultra, Thermo Scientific, Bremen, Germany) with a nano-ESI sprayer (TriVersa NanoMate; Advion Bioscience, Ithaca, NY). A voltage of 1.4 kV vs the inlet was applied with 0.3 psi drying gas. 50 scans were collected with 5 microscans in one scan. The mass range was set from 600 to 2,000 m/z.

MS compatibility comparison to common surfactants. Ubi was dissolved in buffer containing 75:10:5:10 MeOH: $H_2O$: formic acid: 1% surfactant (MaSDeS, PM, RG, NS, SDS, Azo, OG, DDM, DGT) with 10 mM TCEP. The Azo sample was irradiated for 3 min. The acid-labile surfactants were incubated for 75 min (24 hr for MaSDeS) at 37° C. The samples were then directly injected into a 12 T Fourier transform ion cyclotron resonance (Solarix) mass spectrometer (Bruker Daltonics, Bremen, Germany) with a nano-ESI sprayer (TriVersa NanoMate; Advion Bioscience, Ithaca, NY). A voltage of 1.4 kV vs the inlet was applied with 0.3 psi drying gas. 200 scans were averaged for each sample. The mass range was set from 600 to 2,000 m/z with a 512,000 word transient.

LC-MS compatibility comparison to common surfactants using endogenous cardiac tissue lysate. To 15 µL of swine cardiac protein extract (2 mg/mL) was added 1.5 uL water, 6 uL methionine (25 mg/mL), 25 L isopropanol, 5 uL TCEP (100 mM), and 2.5 uL formic acid. The Azo sample was irradiated for 3 min. The acid cleavable surfactants PM and RG (also known as ALS) were incubated at 37° C. for 1 h while MaSDeS was incubated at 37° C. for 24 hr. All samples without (NS) or with the surfactants (MaSDeS, PM, RG, SDS, Azo, OG, DDM, DGT) were buffer exchanged into 10% ACN, 10% IPA, and 1% FA using a MWCO filter (3×100 uL) and adjusted to the original volume of 50 uL (see Table 2).

TABLE 2

| Water | Methionine 25 mg/mL | Surfactant 1% in 25 mM $NH_4HCO_3$ | Extract 2 mg/mL | IPA | TCEP 100 mM | Formic acid |
|---|---|---|---|---|---|---|
| 1.5 µL | 6 µL | 5 µL | 15 µL | 25 µL | 5 µL | 2.5 µL |

Evaluation of the addition of reducing agents during Azo degradation. Standard proteins, Ubi, RNase A, Cytc, and BSA were dissolved in 49.5:49.5:1 $H_2O$: IPA: formic acid and kept on ice until analysis. Samples were irradiated with a 100 w lamp for 3 min. 5 µL of sample was injected onto a trap column and eluted with 40:40:20 ACN: IPA: 1% formic acid in $H_2O$ after a 5 min wash with 2.5:2.5:95 ACN: IPA: 1% formic acid in $H_2O$. 50 mM of DTT, TCEP, and 2-ME were added to each Cytc samples prior to irradiation. Additionally, a sample of Cytc was kept at RT with no reducing agent and irradiated for 3 min with no reducing agent as controls.

Reversed-Phase Chromatography Coupled to Mass Spectrometry. The reversed phase chromatography gradients for various extraction procedures are provided in Table 3. 20 µL of cardiac tissue lysate with or without Azo (referred to as "Azo" or "NS", respectively) was added 116 µL $H_2O$, 2 µL of hexafluoroisopropanol (HFIP) (5%), 2 µL trifluoroacetic acid (10%), 10 µL TCEP (1 M), 50 µL IPA, 50 µL ACN. Reagents were added slowly and mixed throughout to avoid precipitation. The samples were transferred to a quartz cuvette and irradiated for 3 min using a 100 w high pressure mercury lamp. The resulting samples exchanged into 20% ACN: IPA (1% formic acid) with a 10 kDa MWCO centrifugal filter and adjusted to a final volume of 200 µL.

50 µL of enriched sarcoplasmic reticulum and mitochondria lysate from cardiac tissue was diluted with 440 µL of 50:48.5:1:0.5 IPA: $H_2O$: formic acid: HFIP and 10 UL of TCEP (1 M). The sample was irradiated 3 min and concentrated to a final volume of 10 µL MWCO (10 kDa).

50 µL of enriched sarcoplasmic reticulum and mitochondria lysate from HEK cells was diluted with 400 µL of 50% IPA: 49% $H_2O$: 1% formic acid and 50 µL of TCEP (1M). The sample was irradiated 3 min, concentrated and exchanged into 10:10:80 ACN: IPA: 1% formic acid in $H_2O$ with a 10 kDa MWCO centrifugal filter. The final volume was adjusted to 200 µL.

Cytosolic cardiac protein extract was diluted to a final buffer containing 25% IPA, 25% ACN, 1% formic acid, 100 mM TCEP, and either 0.2% Azo or 5 mM $NH_4HCO_3$. The sample was irradiated for 3 min and exchanged into a 10% ACN, 10% IPA, with 0.2% formic acid using a 10 kDa MWCO centrifugal filter.

Reversed phase chromatography (RPLC) was performed with a nanoACQUITY M-Class UPLC system (Waters; Milford, MA, USA). Mobile phase A (MPA) contained 0.2% formic acid in $H_2O$, and mobile phase B (MPB) contained 49.9% ACN: 49.9% IPA: 0.2% formic acid. For each injection, 5 L of sample was loaded on a home-packed 250×0.250 mm, 5 µm, 1000 Å PLRP-S(Agilent Technology, Santa Clara, CA, USA) column. A constant 4 µL/min flow rate was used. For the surfactant comparison 10 µL of sample was loaded onto a 100×0.5 mm, 5 µm, 1000 Å PLRP-S and separated with a flow rate of 15 µL/min.

TABLE 3

Reversed phase chromatography gradients for various extraction procedures.

| Cardiac tissue | | | SR/Mit from Cardiac tissue | | | SR/Mit from HEK cells | | |
| --- | --- | --- | --- | --- | --- | --- | --- | --- |
| Time (min) | % A | % B | Time (min) | % A | % B | Time (min) | % A | % B |
| 0 | 80 | 20 | 0 | 95 | 5 | 0 | 80 | 20 |
| 5 | 80 | 20 | 1 | 95 | 5 | 5 | 80 | 20 |
| 25 | 60 | 40 | 5 | 70 | 30 | 65 | 5 | 95 |
| 65 | 40 | 60 | 55 | 40 | 60 | 75 | 5 | 95 |
| 75 | 25 | 75 | 57 | 5 | 95 | 76 | 80 | 20 |
| 80 | 5 | 95 | 65 | 5 | 95 | 80 | 80 | 20 |
| 85 | 5 | 95 | 67 | 95 | 5 | 50° C. | | |
| 86 | 80 | 20 | 80 | 95 | 5 | | | |
| 95 | 80 | 20 | 35° C. | | | | | |
| RT | | | | | | | | |

Reversed phase chromatography gradients for various extraction procedures. Samples eluted from the column were sprayed directly into a maXis II ETD Q-TOF mass spectrometer (Bruker Daltonics, Bremen, Germany) for online LC-MS and LC-MS/MS experiments. End plate offset and capillary voltage were set at 500 and 4000 V, respectively. The nebulizer was set to 0.5 bar, and the dry gas flow rate was 4.0 L/min at 220° C. The quadrupole low mass cutoff was set to 600 m/z during MS and 200 m/z during MS/MS. Mass range was set to 200-3,000 m/z and spectra were acquired at 1 Hz for LC-MS runs. For the top three data-dependent LC-MS/MS CID runs, MS/MS spectra were acquired across 200-2,500 m/z at 2-6 Hz with active exclusion after four spectra. Targeted LC-MS/MS CID was performed at 1 Hz after determining the elution time frame from the targeted proteins. All data were collected with OtofControl 3.4 (Bruker Daltonics).

Data were analyzed and processed in DataAnalysis 4.3 (Bruker Daltonics). An msalign file was created using SNAP peak picking algorithm with the following parameters: quality factor: 0.4; S/N: 3; intensity threshold: 500; retention window: 1.5 min. The file contained the following information: precursor mass, precursor charge, precursor mass followed by the fragment masses, intensities, and charges. The alignment-based TopPIC was utilized for intact protein identification based on protein spectrum matches searching against the UniProt *Sus scrofa* (released on Nov. 22, 2017; containing 26817 protein sequences) or *Homo sapiens* (released on Dec. 20, 2017; containing 20244 reviewed protein sequences) database (Apweiler et al., 2004, Nucleic acids research, 32 (Database issue), D115-9). Fragment mass tolerance was set to 15 ppm. All identifications were validated with statistically significant P and E values (<0.01) and satisfactory numbers of assigned fragment ions (>10). Additionally, all identifications were manually validated us Mash Suit Pro (Cai et al., 2016, Molecular & cellular proteomics: MCP, 15 (2): 703-14) and the corresponding MS and MS/MS data were summarized. For ATP synthase a, a single charge state was isolated and fragmented with 5, 10, 16, 18, 20 ev, respectively, using an isolation window of 3 m/z during targeted CID MS/MS experiments. A mass list from the resulting fragment ions was generated and an identification made as described above.

A proteoform map was generated using a data analysis script as followed (1) LC-MS data were averaged every min; (2) deconvoluted using Max Entropy algorithm (Resolution: 80,000; mass range: 5,000-60,000 Da); (3) mass list output generated using SNAP peak picking (quality factor: 0.8, S/N: 3, absolute intensity 1,000). A graphic map was then generated in Microsoft Excel based on the first retention time and the monoisotopic mass.

Statistical analysis. For the protein solubility experiment (FIG. 2, panel c) comparing Azo, SDS, DDM, and MaSDeS, three independent protein assays (n=3) were performed to evaluate surfactant performance. Error bars represent standard error of the mean. For the broader protein solubility comparison (FIG. 16), data presented were based on three independent experiments (n=3). Error bars represent standard error of the mean. For LC-MS analysis (FIG. 15), three separate samples (n=3) were prepared for each condition. Error bars represent standard error of the mean.

Conclusion. In summary, these results demonstrate a generalizable, high-throughput method for ESI-MS analysis of intact proteins utilizing a photo-cleavable surfactant to increase protein solubility and overall throughput. Among all the surfactants that were evaluated, which included a library of photo-cleavable surfactants, acid-labile surfactants and traditional non-ionic and anionic surfactants, Azo was the only strong surfactant capable of effective solubilization of proteins without hindering downstream top-down MS analysis. Notably, Azo can directly address the solubility challenge in top-down proteomics and significantly increase the number of proteins that can be confidently identified in a given run.

This study provides a streamlined method for analyzing intact proteins that are typically difficult to extract which prohibit further MS analysis. Moreover, Azo has the potential to improve global top-down proteomics studies when coupled to multidimensional separation method, combined with complementary fragmentation techniques for comprehensive protein characterization, and with further improvements in data acquisition strategies (Chen et al., 2018, Anal. Chem. 90:110-127; and Durbin et al., 2014, Anal. Chem. 86:1485-1492).

Example 3—Systematic Comparison of Azo with Common Surfactants

A systematic comparison of Azo was performed with commonly used surfactants to evaluate their ability to solubilize proteins from the insoluble cardiac tissue pellets (similarly as described above). The surfactants used for comparison include non-ionic surfactants, octyl β-D-glucopyranoside (OG) and dodecyl β-D-maltoside (DDM), digitonin (DGT), as well as anionic, acid-labile surfactants, RapiGest™ (RG) (also known as ALS), ProteaseMax™ (PM) 1, and MS-compatible slowly-degradable surfactant (MaSDeS), together with SDS and Azo. Non-ionic saccharide surfactants such as DDM and OG can be MS-compatible when used at lower concentrations (0.01-0.1%) but they are considered to be relatively mild with limited solubilization ability. On the other hand, anionic surfactants such as SDS and acid-labile SDS mimics are much stronger, capable of solubilizing and denaturing proteins with high efficiency. Acid-labile surfactants were originally developed for improving in-gel or in-solution digestion efficiency for bottom-up proteomics.

Utilizing SDS-PAGE (FIG. 16, panel a) and Bradford protein assay (Bio-Rad) analysis (FIG. 16, panel b), anionic surfactants including SDS, MaSDeS, PM, RG, and Azo, showed drastically better protein solubilization ability than the non-ionic surfactants, OG, DDM, and DGT. In particular, Azo effectively extracted proteins at a level similar to other leading anionic surfactants such as SDS, MaSDeS, RG, and PM.

Subsequently, a comparison of the MS-compatibility of Azo was performed with these leading surfactants (FIG. 17). The mass spectrometry analysis in the presence of 0.1% surfactants, showed that SDS and MaSDeS dramatically suppressed the MS signal of the intact Ubi; RG and PM significantly suppressed the MS signal of Ubi; whereas Azo and non-ionic surfactants, OG, DDM, and DGT showed minimal MS protein signal suppression.

Figure 18:
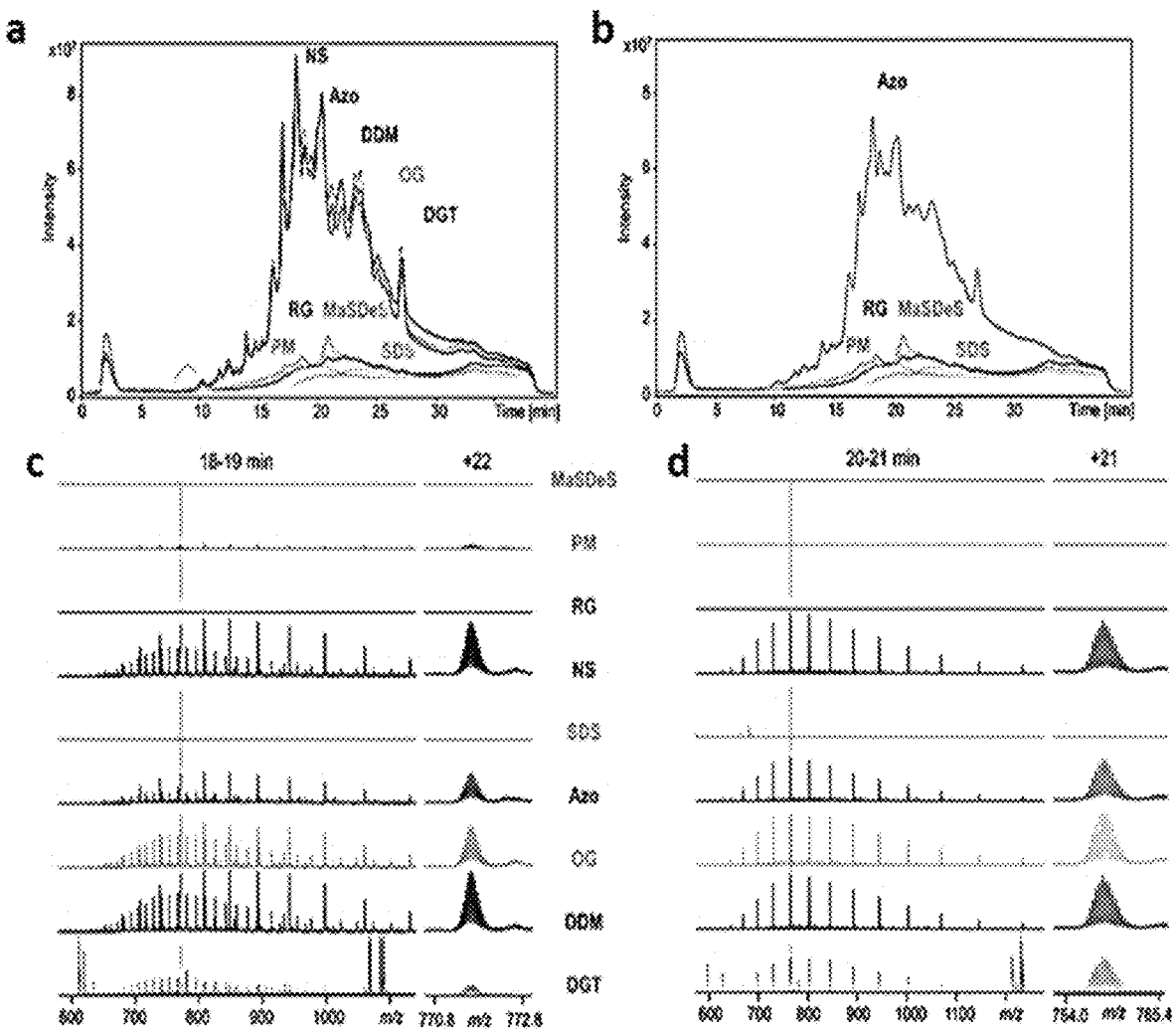
FIG. 18—Comparison of surfactant effect on LC-MS analysis of cardiac tissue lysate. Cardiac proteins extracted using $NH_4HCO_3$ buffer either without surfactant (NS, serve as control) or with surfactant (0.1%). The surfactants tested here include MS-compatible slowly-degradable surfactant (MaSDeS), ProteaseMax™ (PM), RapiGest™ (RG, also known as ALS), sodium dodecyl sulfate (SDS), 4-hexylphenylazosulfonate (Azo), Octyl β-D-glucopyranoside (OG), dodecyl β-D-maltoside (DDM), and digitonin (DGT). The acid- and photo-cleavable surfactants were degraded under acid or UV respectively. All the samples were buffer exchanged and analyzed by LC-MS. Mass spectra were collected on a Bruker maxis II Q-TOF mass spectrometer. Panel (a), total ion chromatogram comparing the MS signal of cardiac tissue lysate in the presence of different surfactants compared to control. Panel (b), total ion chromatogram comparing the MS signal of cardiac tissue lysate in the presence of different anionic surfactants. Panel (c), representative mass spectra from proteins eluted at 18-19 min showing multiple co-eluting proteins. Intensity normalized to 1.36E4. Panel (d), representative mass spectra of a protein eluted from 20-21 min. Intensity normalized to 1.62E5.

Importantly, a broader comparison on the LC-MS-compatibility of Azo was also performed with other commonly used surfactants using cardiac tissue lysate (FIG. 18). The LC-MS analysis of the lysate with 0.1% surfactants demonstrated great top-down MS-compatibility of Azo, OG, DDM, and to a lesser extent DGT. On the other hand, significant signal supression was observed in the presence of SDS and all acid cleavable surfactants, PM, RG, and MaSDeS. Overall, these comparison studies have demonstrated Azo's unique ability to effectively solubilize proteins without interfering with downstream top-down MS analysis (FIG. 25).

Example 4—Identification of Proteoforms in Top-Down Proteomics

In this study, a total of 2836 proteoforms were detected based on accurate mass measurements from the combination of three LC/MS runs. However, only 388 proteoforms were identified based on one-dimensional online RPLC-MS/MS data representing 171 proteins from mitochondria, nucleus, plasma membrane, cytoskeleton, endoplasmic reticulum, cytoplasm, and extracellular regions (FIG. 4). The low proportion of protein identification is not a result of proteins being modified by UV photolysis reactions or Azo-induced artifactual modification as demonstrated (FIG. 2, panel d, and FIGS. 12-15 and 17-18). Instead, it is a result of the current limitation on protein separation, fragmentation, data acquisition, and identification algorithms in top-down proteomics (Chen et al., 2018, Anal. Chem. 90:110-127).

Top-down MS is inherently limited in its ability to identify proteins compared to bottom-up proteomics, despite its advantage in offering a deeper understanding of the existing proteoforms. Even though the proteoforms could be detect based on their distinct accurate molecular masses, the fragments obtained from the online MS/MS are typically limited especially for large proteins, which makes it difficult to unambiguously identify all of the proteins (proteoforms) detected using the currently available database search algorithm (Cai et al., 2017, Anal. Chem. 89:5467-5475). In particular, a single dimension of separation is not sufficient to achieve large proteoform identification, but does serve to demonstrate the potential of this surfactant to improve protein solubility and overall throughput.

Admittedly, a well-recognized challenge in top-down proteomics is the detection of large proteins due to the exponential decay in S/N in a mass spectrometer as a function of increasing molecular mass (Compton et al., 2011, Anal. Chem. 83:6868-6874). Top-down mass spectrometry is biased against larger protein species especially when a single dimension of separation is used; thus, the low molecular weight (MW) proteins may show up more readily even if they are in lower abundance.

Furthermore, the relatively lower number of identification could be due to the co-elution problems since only 1DLC is used in this study with limited separation power, which means that lower abundance and higher MW proteins could be insufficiently fragmented in online LC-MS/MS if co-eluting with higher abundance and lower MW species. It is expect that the incorporation of multi-dimensional (MD) LC separation of intact proteins reduces the co-elution of proteins, which enables the detection and identification of low abundance and/or high MW proteins towards a deeper proteome coverage (Cai et al., 2017, Anal. Chem. 89:5467-5475; and Valeja et al., 2015, Anal. Chem. 87:5363-5371). Nevertheless, the MDLC strategies need significant amount of samples and dramatically longer experiment time than 1DLC (Chen et al., 2018, Anal. Chem. 90:110-127). Moreover, RPLC could impose some concerns for analyzing hydrophobic proteins (e.g. too much retention on the column), although early work on intact integral membrane proteomics, namely characterization of GPCR (7TMD) bacteriorhodopsin, was performed using a polymeric reversed-phase material, PLRP-S, with column heating as described in a previous study (Whitelegge et al., 1998, Protein Sci. 7:1423-1430).

In this study, the elution of very hydrophobic species, such as ATP synthase subunit c, was observed also using PLRP-S materials with column heating. Notably, ATP synthase subunit c has a gravy score (an amino acid based hydrophobicity scale that is particularly relevant for denatured proteins) of 1.14 when compared to Bacteriorhodopsin, 0.78, which illustrates that highly hydrophobic species can be evaluated using such RPLC method. However other separation modes may improve the analysis of hydrophobic species and it is important to actively investigate other chromatographic modes for membrane protein separation.

Lastly, while potential improvements could be made should complementary dissociation techniques be applied, other dissociation techniques such as ultraviolet photodissociation (UVPD) may have limited improvement over collision-induced dissociation (CID)/higher-energy collisional dissociation (HCD) in terms of the number of protein identifications via online LC-MS/MS and data dependent acquisition mode (Cleland et al., 2017, J. Proteome Res. 16:2072-2079). For membrane proteins, CID/HCD fragments transmembrane domains particularly well and highly efficient CID fragmentation was observed which preferentially cleaved in the transmembrane in agreement with previous studies (Whitelegge et al., 1998, Protein Sci. 7:1423-1430; and Skinner et al., 2014, Anal. Chem. 86:4627-4634). On the other hand, from a protein characterization standpoint, the use of complementary dissociation techniques, such as UVPD, electron transfer dissociation (ETD)/electron capture dissociation (ECD) together with CID/HCD significantly improved sequence coverage and could greatly aid proteoform characterization (e.g. labile PTM localization) (Chen et al., 2018, Anal. Chem. 90:110-127; Cleland et al., 2017, J. Proteome Res. 16:2072-2079; and Lin et al., 2018, J. Am. Soc. Mass Spectrom 29:1284-1294). Nevertheless, this generally requires a more targeted approach to accumulate sufficient spectra, which is better suited to implement a targeted proteomics approach addressing a specific biological question.

Therefore, Azo is believed to have the potential to improve global top-down proteomics studies when coupled to multidimensional separation methods (Valeja et al., 2015, Anal. Chem. 87:5363-5371; Cai et al., 2017, Anal Chem 89:5467-5475; and Xiu et al., 2014, Anal. Chem. 86:7899-7906), complementary fragmentation techniques such as UVPD and ETD/ECD for comprehensive protein characterization (Cleland et al., 2017, J. Proteome Res., 16:2072-2079; Lin et al., 2018, J. Am. Soc. Mass Spectrom, 29:1284-1294; and Riley et al., 2016, J. Am. Soc. Mass. Spectrom. 27:520-531), and with further improvements in data acqui-

Example 5-Photo-Cleavable Surfactant for Bottom-Up Proteomics

Bottom-up proteomics is a widely used technology for characterizing the proteome. The traditional approach to bottom-up uses SDS or urea to extract and denature proteins for enhanced tryptic digestion. These methods require extensive clean-up steps prior to mass spectrometry (MS) analysis. This example presents a high-throughput method for extracting, digesting, and analyzing proteins by tandem MS (LC-MS/MS) using a photo-cleavable surfactant (Azo) that eliminates the need for additional clean-up steps and greatly enhances the speed of digestion. This method enables reproducible protein extraction, digestion, and LC-MS/MS analysis in a highly streamlined fashion.

Figure 30:
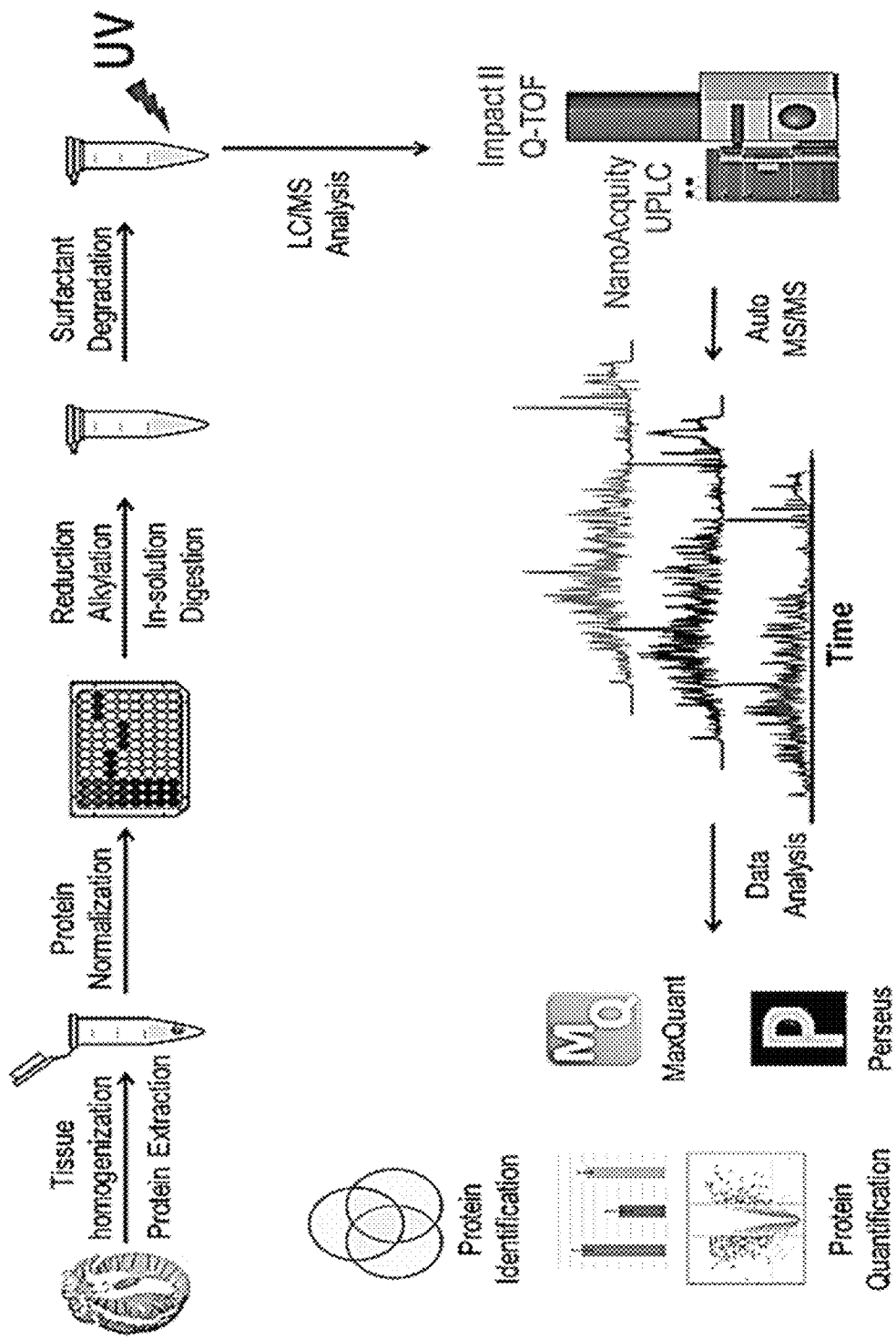
FIG. 30—High-throughput workflow for an Azo-aided bottom-up proteomic experiment.
Figure 31:
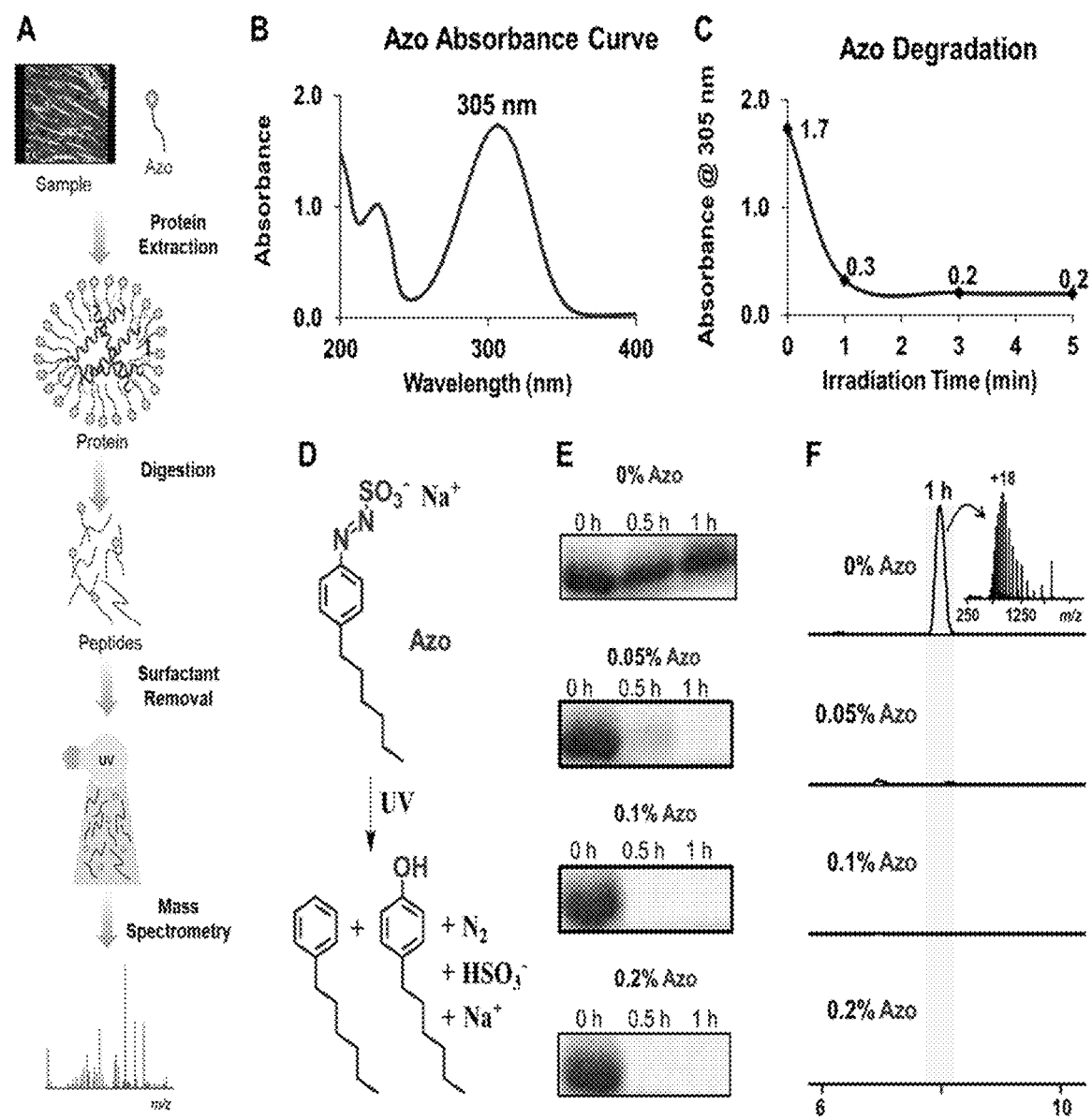
FIG. 31—Panel (A), simplified workflow for an Azo-aided bottom-up proteomic experiment. Panel (B) UV-Vis spectrum for Azo highlighting maximal absorbance at 305 nm. Panel (C), UV-Vis spectrum monitoring the rapid degradation of Azo (0.1% in water) as a function of irradiation time with a 100 W mercury lamp. Panel (D), degradation of Azo by UV irradiation as previously described36. Panel (E), digestion of myoglobin [1-h in Azo (0-0.2%)] was monitored by SDS-PAGE, stained with Coomassie blue, and LC-MS with an Impact II Q-TOF mass spectrometer. Extraction ion chromatogram of intact myoglobin shows increased digestion rate in the presence of Azo. Panel (F), myoglobin digestion using trypsin in the presence of 0, 0.05, 0.1, and 0.2% Azo.

In particular, Azo is compatible with bottom-up proteomics, provides a robust high-throughput approach for proteomics analysis (FIG. 30), and significantly enhances protein extraction and enables rapid digestion for bottom-up proteomics (FIG. 31, panel A).

Figure 29:
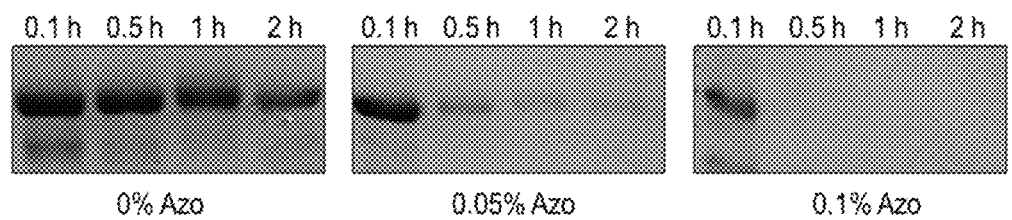
FIG. 29—Azo enabled digestion in a bottom-up proteomic experiment. Panel (A), BSA digestion monitored by SDS-PAGE in the presence of 0, 0.05, 0.1% Azo. Panel (B), Myoglobin digestion monitored by LCMS. Extraction ion chromatogram of intact myoglobin shows increased digestion in the presence of Azo.
Figure 29:
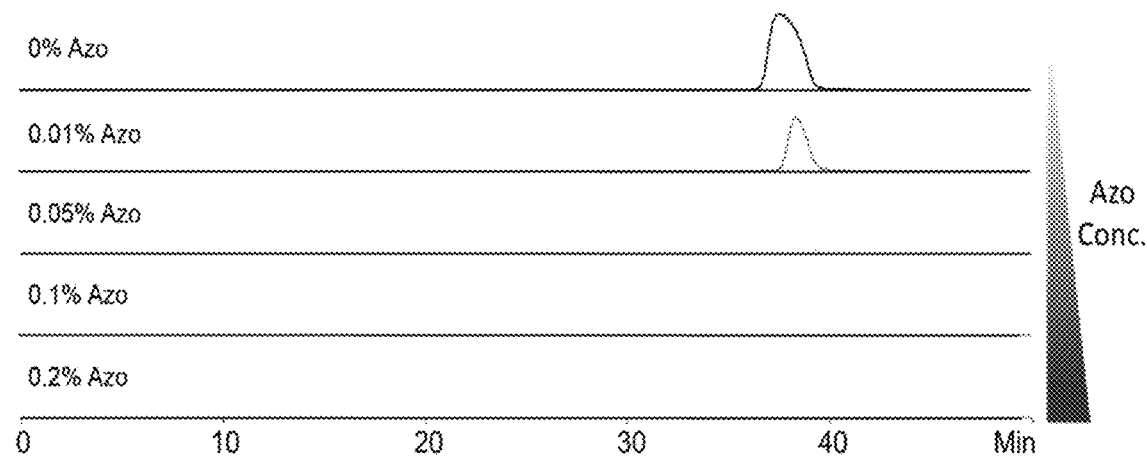

Rapid degradation, digestion and analysis. To begin with, Azo's ability to facilitate rapid degradation was evaluated. 25 μg of bovine serum albumin (BSA) was digested at 0.1, 0.5, 1, and 2 h in the presence of 0, 0.05, 0.1% Azo. Protein digestion was monitored using SDS-PAGE (FIG. 29, panel A). Similarly, myoglobin was digested for 1 h in the presences of 0, 0.05, 0.1%, and 0.2% Azo (FIG. 29, panel B). Rapid protein digest was observed (<0.5 h) using Azo (0.1%) while a sample without Azo remained intact.

Rapid degradation of Azo was further demonstrated by UV-Vis spectroscopy, where the intact surfactant had a maximal absorbance at 305 nm (FIG. 31, panel B). 50 μL of 0.1% Azo in 25 mM ammonium bicarbonate (ABC) was irradiate for 0, 1, 3, 5 min using a 100 W mercury lamp (Nikon housing with HB-10101 AFT power supply). The sample was diluted with 950 μL of water and a spectrum was taken using Varian Cary 50 UV-Visible (600 nm-200 nm, background correction, fast scan rate). In aqueous conditions, 0.1% Azo solution degraded rapidly upon UV irradiation (FIG. 31, panels C and D). This facile surfactant removal method makes Azo ideal for rapid sample processing.

Next, Azo-aided in-solution digestion was evaluated. Myoglobin, a globular protein, was digested in-solution without (0%, control) or in the presence of 0.05%, 0.1%, or 0.2% Azo. The efficiency of digestion was assessed by visualization of the remaining intact myoglobin through SDS-polyacrylamide gel electrophoresis (SDS-PAGE) analysis (FIG. 31, panel E). After 0.5 h of digestion in the absence of surfactant, the intact protein band at ~17 kDa was observed, suggesting poor digestion efficiency. In contrast, only a faint intact protein band was observed in the presence of 0.05% Azo, and no intact protein band was observed in the presence of 0.1% and 0.2% after 30 min of digestion indicating greatly improved digestion efficiency by Azo. Subsequently, a longer digestion time (1 h) was evaluated in the presence or absence of Azo. Even after 1 h digestion, a predominant intact protein band was still observed without Azo, whereas no intact protein was observed in the presence of 0.05%, 0.1%, or 0.2% Azo (FIG. 31, panel F). This is conceivable, since without a denaturing agent (i.e. an anionic surfactant) the enzyme has limited access to the protein backbone. These results indicate Azo facilitates denaturation of the protein, providing efficient digestion.

Figure 35:
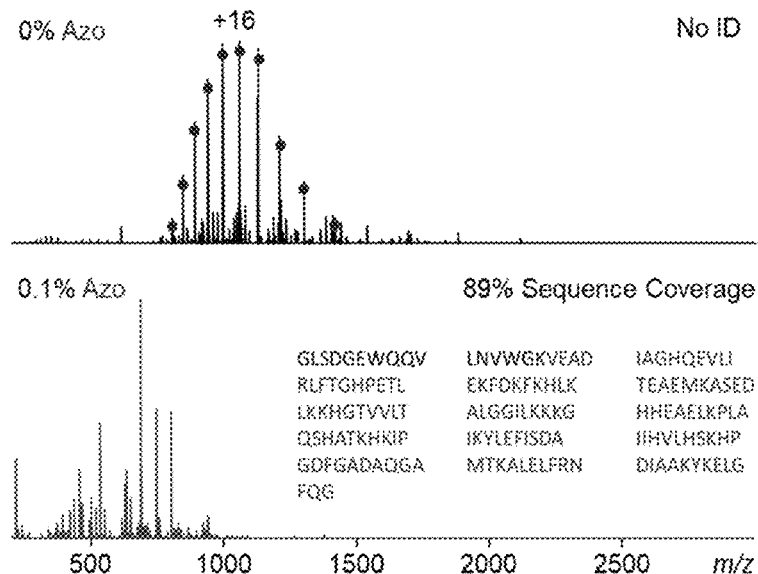
FIG. 35—Myoglobin was digested with trypsin in 0% (top) or 0.1% (bottom) Azo for 1 hr. The sample was directly infused into a Bruker 12T solariX™ FTICR. Intact myoglobin signal (indicated by circles) was observed with trypsin alone without Azo whereas complete digestion was observed in the presence of Azo. Overall, no identification was obtained for the digestion without surfactant. In contrast, 89% sequence coverage was achieved using peptide mass fingerprinting when digestion was performed in the presence of Azo.
Figure 36:
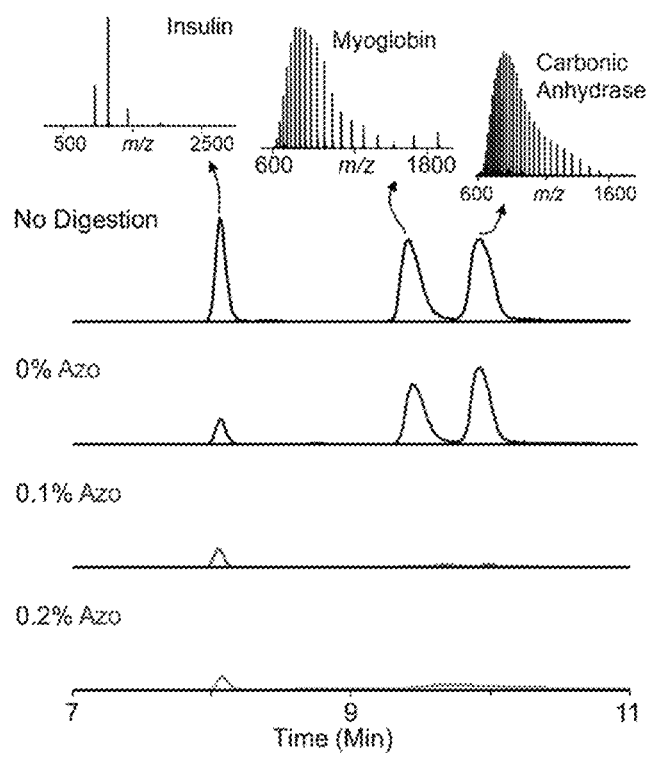
FIG. 36—Insulin, myoglobin, and carbonic anhydrase were digested using trypsin in the presence of 0, 0.1, and 0.2% Azo. The presence of intact protein was monitored by LC-MS using a maxis II ETD Q-TOF. Extracted ion chromatograms of intact proteins show increased digestion rate in the presence of Azo.

Next, the Azo-aided (0.1% Azo, 1 h) myoglobin digest was infused for peptide mass fingerprinting analysis without an additional clean-up procedure and an 89% sequence coverage was observed. On the other hand, analysis of the myoglobin sample digested in the absence of surfactant (0% Azo, 1 h) yielded minimal detectable peptides, and the MS signal was largely dominated by the intact protein (FIG. 35). To confirm the rapid rate of enzymatic digestion in the precedence of Azo, a standard mixture of insulin, myoglobin, and carbonic anhydrase was digested with and without Azo. Partially digested insulin and intact myoglobin and carbonic anhydrase were observed without Azo (FIG. 36), while no detectable intact myoglobin or carbonic anhydrase was observed after 1 h of digestion in the presence of 0.1% or 0.2% Azo and only a small amount of intact insulin was observed (FIG. 36). Taken together, these results indicate proteins can be efficiently and rapidly digested (<1 h) in the presence of Azo.

Figure 32:
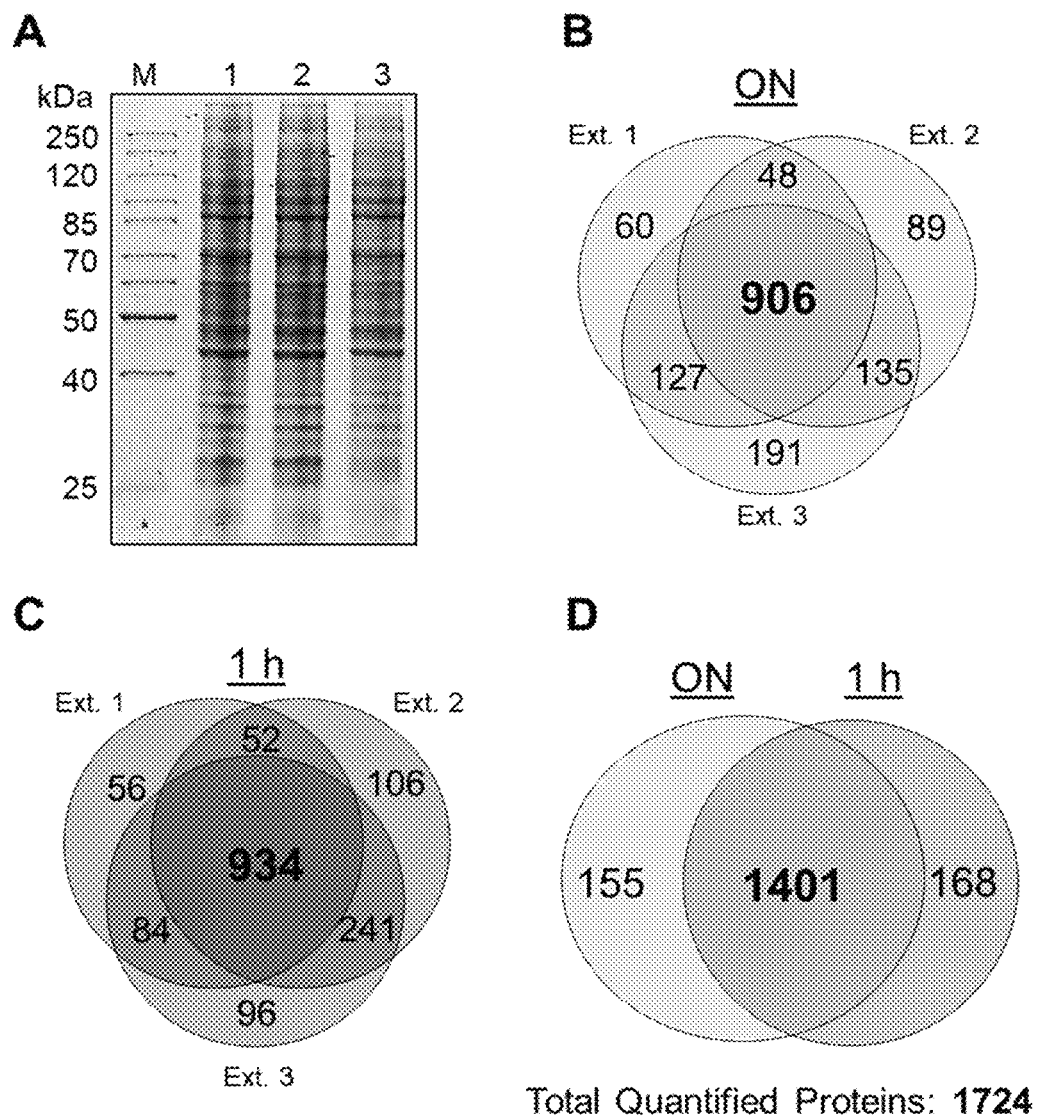
FIG. 32—HEK293T cells were lysed with Azo. Panel (A), SDS-PAGE analysis demonstrates consistent extraction profiles across three biological replicates. Two aliquots were taken from each exaction and digested overnight (ON) or for 1 h. After LC-MS and MaxQuant label-free quantification a high degree of overlap was observed for both the (panel B) ON and (panel C) 1 h biological replicates. Similarly, (panel D) 1401 of the 1724 combined quantifiable proteins were observed in both digestion methods. Venn diagrams generated using Venny 2.1.

After demonstrating rapid enzymatic digestion using standard proteins, Azo-aided digestion of complex cell lysates was further investigated. Azo was first used to extract proteins from human embryonic kidney 293T (HEK293T) cells. SDS-PAGE analysis demonstrated reproducible extractions for three HEK samples (FIG. 32, panel A). The proteins were digested for 1 h overnight (ON) to determine whether digestion time, the most time-consuming step in the bottom-up proteomic workflow, could be shortened using Azo while maintaining reproducibility. After LC-MS/MS analysis, the data was processed using MaxQuant for label-free quantification. An intensity-based absolution quantification (iBAQ) (Schwanhäusser et al., 2011, Nature, 473: 337) was used as a benchmark for assessment of reproducibility and compared three biological replicates digested for either 1 h or overnight. Overall, 906 and 934 protein were quantifiable in all three replicates using ON digestion (FIG. 32, panel B) and 1 h digestion (FIG. 32, panel C), respectively. Combined, 1556 protein were quantified using an ON digestion and 1569 proteins were quantified using a 1 h digestion. This corresponded to an 81% overlap between the two conditions (FIG. 32, panel D), confirming 1 h is sufficient for effective protein digestion in the presence of Azo. These results further demonstrate the ability of Azo to accelerate the digestion step in the bottom-up workflow.

Figure 33:
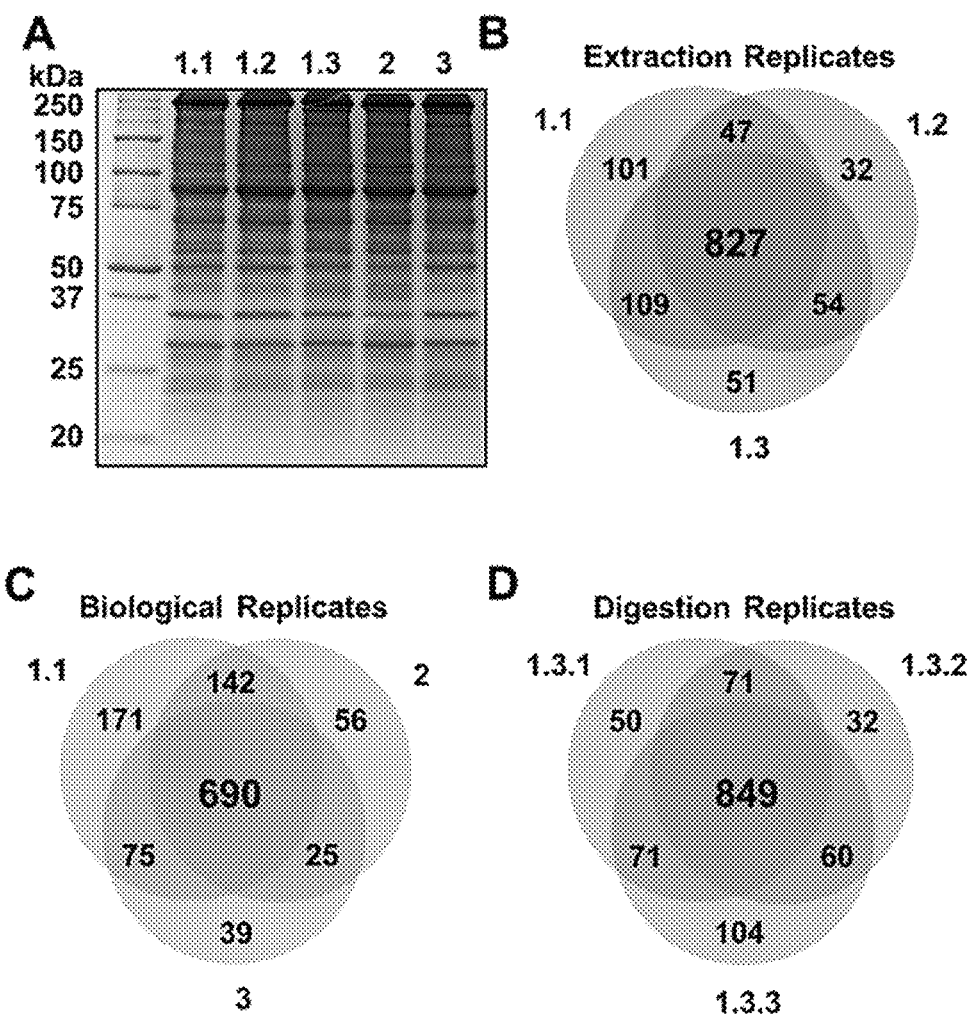
FIG. 33—Panel (A), SDS-PAGE visualization of protein extracted from swine myocardium. 1.1, 1.2, 1.3 represent extraction replicates (n=3) and 1.1-1.3, 2, 3 represent biological replicates (n=3). Panel (B), overlap of identified genes for tissue extraction replicates from the same biological sample (extraction from tissue from animal 1, n=3). Panel (C), overlap of identified genes for biological replicates (extract from different animals, n=3). Panel (D), overlap of identified genes for digestion replicates (digestion from extract 1.3, n=3). Panel (E), GO analysis for biological processes. Panel (F), GO analysis for molecular function. GO analysis was performed using Panther software.
Figure 33:
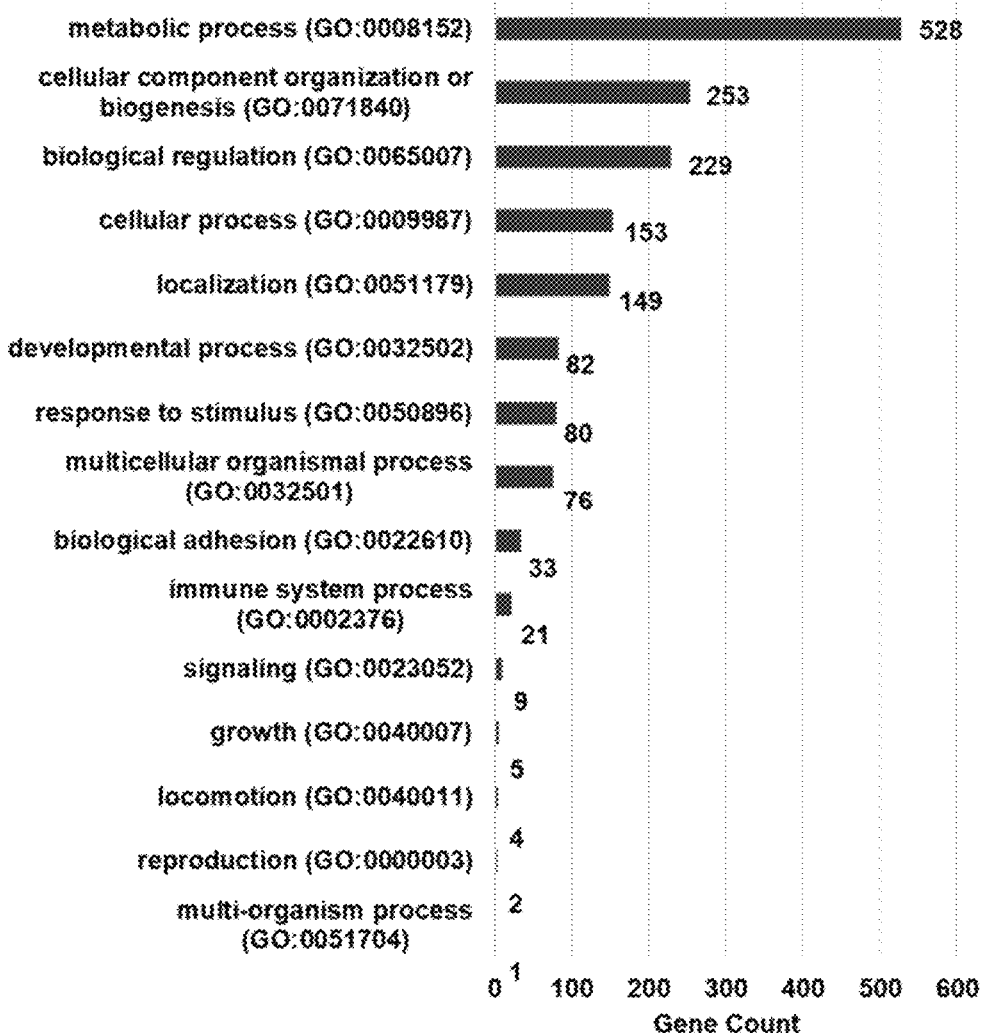
Figure 33:
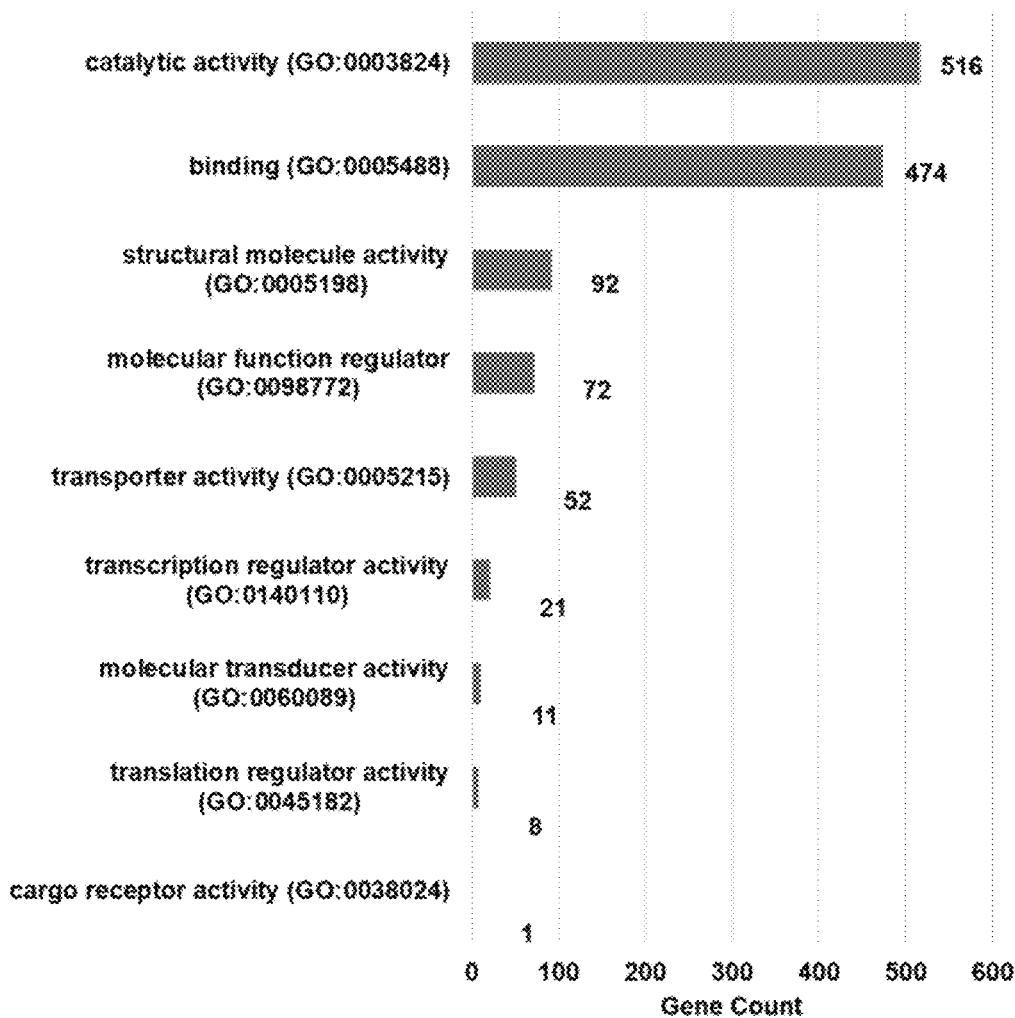

The applicability of Azo-aided bottom-up proteomics in tissue proteomics is further demonstrated by applying this strategy to the analysis of swine cardiac tissue. Azo was used to extract proteins from three different swine hearts as well as three extraction replicates from one heart and showed high reproducibility for biological and technical extraction replicates by SDS-PAGE analysis (FIG. 33, panel A). Furthermore, LC-MS/MS analysis showed good reproducibility between extraction (FIG. 33, panel B), biological (FIG. 33, panel C), and digestion replicates (FIG. 33, panel D) after trypsin digestion using iBAQ quantification as a benchmark. Using Gene ontology analysis (Ashburner et al., 2000, Nat Genet, 25:25-29), the major class of proteins involved in metabolic processes, cellular component organization or biogenesis, and cellular processes were observed (FIG. 33, panel E). Most proteins were shown to be catalytic active or binding properties through molecular function sorting (FIG. 33, panel F).

Methods used in the above experiments are described further below.

Digestion and Analysis of Standard Proteins. Myoglobin (25 µg) was dissolved in 25 mM ABC with 0, 0.05, 0.1, 0.2% Azo (final volume was 50 µL). 10 µL was collected before digestion and boiled in SDS loading dye for SDS-PAGE analysis. Trypsin (1:50 enzyme: protein) was added to the remaining myoglobin solution and the sample was incubated at 37° C. 10 pL was collected at 0.5 h and 1 h, respectively, and boiled in SDS loading dye to quench the reaction. The samples were loaded onto a 10% acrylamide gel, separated with 125 V, and stained with Coomassie blue for visualization (FIG. 31, panel E).

The remaining digested (1 h, 0-0.2% Azo) myoglobin was analyzed by liquid chromatography-mass spectrometry (LC-MS) analysis, the sample was irradiated with UV and the protein was separated on a PLRP column (200×0.25 mm, 10 µm, 1000 Å) using 0.2% formic acid in water (A) and ACN:IPA (B) with a 15 min gradient from 20%-80% B. The sample was eluted from the column and infused into maxis II ETD Q-TOF (Bruker Daltonics) using 4500 V and an endplate voltage of 500 V. MS scans were collected at 1 Hz (FIG. 31, panel D).

Additionally, the digested (1 h, 0.1% Azo) myoglobin was directly infused into a 12T solariX™ Fourier Transform Ion Cyclotron mass spectrometer (Bruker Daltonics) mass spectrometer using a nano-ESI source (Triversa NanoMate; Advion Bioscience, Ithaca, NY). A voltage of 1.5 kV was applied with 0.3 psi drying gas for peptide mass fingerprinting. Scans were collected at 512,000 word with a mass range of 200-3000 m/z. Data were analyzed in Mascot allowing for 2 missed cleavages with oxidation (M) as a variable modification (FIG. 35).

Finally, 10 µg insulin, 20 µg of myoglobin, and 60 µg of carbonic anhydrase were digested in 0, 0.1, and 0.2% azo for 1 hr. After digestion the samples were irradiated with UV and analyzed by LC-MS using a maXis II ETD Q-TOF as described above for myoglobin (FIG. 36).

Protein Extraction, Digestion, and LC-MS/MS Analysis of HEK293T Cells. Human embryonic kidney (HEK) cells (ATCC, Manassas, VA) were grown on 10-cm plates with 10% FBS and 1× Penicillin-Streptomycin at 37° C. with 5% $CO_2$. Plates (~90% confluent) were washed with PBS, pelleted at 500×g, flash-frozen, and stored at −80° C.

All steps were performed at 4° C. Cells from a single plate were lysed with 250 µL of buffer (0.5% Azo, 25 mM ABC, 5 mM tris(20carboxyethyl) phosphine (TCEP), 5 mM ethylenediaminetetraacetic acid (EDTA), and 1× Halt protease/phosphatse inhibitor cocktail) and sonicated for 5 s (at 20% amplitude) to shear the DNA. The extract was centrifuged for 10 min at 16,000×g and the supernatant removed. Protein concentration was determined using BCA protein assay reagent with albumin as a standard. 25 µg was analyzed by SDS-PAGE.

200 µg of protein (final volume was 50 UL and Azo concentration ~0.1% for digestion) was reduced with 5 mM dithiothreitol (DTT), alkylated with 15 mM iodoacetamide (IAA), and digested with trypsin (1:50) overnight or for 1 h at 37° C. The surfactant was degraded with UV and the reaction was quenched with formic acid. The sample was centrifuged for 5 min at 16,000× g and the supernatant was subsequently collected. \

10 µL samples were loaded onto a home-packed $C_{18}$ column (250×0.25 mm) and separated using a 60 min gradient from 5-40% B. Mobile phases were 0.2% formic acid in water (A) and ACN (B). The column was heated to 60° C. and the flow rate was 5 L/min. Peptides eluted from the column were infused into an Impact II Q-TOF mass spectrometer (Bruker Daltonics) using 4500 V and an endplate voltage of 500 V. MS scans were collected at 2 Hz and the top 30 most intense ions were selected for collision-induced dissociation (CID) using a 3 m/z window, 8-32 Hz (intensity 2500-25000) scan rate, and a voltage energy that was determined on the m/z and charge. (FIG. 32).

Extraction, Digestion, and LC-MS Analysis of Cardiac Proteins. Proteins were extracted from swine cardiac tissue using a one-step Azo extraction. All steps were performed at 4° C. 15-20 mg of cardiac tissue was homogenized in 15 volumes (µL/mg of tissue) of buffer containing 0.5% Azo, 25 mM ABC, 5 mM dithiothreitol (DTT), 5 mM PMSF, and 1× Halt protease/phosphatase inhibitor cocktail with a polytron electric homogenizer. The homogenates were centrifuged for 30 min at 17,000×g at 4° C. and the supernatant was collected for analysis. Protein concentration was determined using Pierce BCA protein assay reagent with bovine serum albumin as a standard. The extracts were normalized to 2 µg/µL and 20 µg of the biological and technical extraction replicates were visualized by SDS-PAGE to qualitatively assess reproducibility.

200 µg of protein (final volume 50 µL) was reduced with 5 mM DTT for 30 min at 37° C., and alkylated with freshly prepared 25 mM IAA for 45 min at room temperature in the dark, quenched with 5 mM DTT, and digested with trypsin (1:50) overnight at 37° C. The reaction was quenched with trifluouracetic acid and the surfactant was subsequently degraded with UV light. The sample was sonicated for 10 min and centrifuged for 30 min at 17,000×g at 4° C. and the supernatant collected for LC-MS analysis.

About 4 µg of peptides were loaded onto a trap column (Waters, 2D Symmetry C18 100A 5 µm 180 um×20 mm), and subsequently separated on an analytical column (Waters, Peptide BEH $C_{18}$ nanoACQUITY 130 A, 1.7 um, 75 um×200 mm), and heated to 60° C. at a flow rate of 0.3 µL/min. Peptides were separated using a 60-min gradient from 5-45% B. Mobile phases were 0.2% formic acid in water (A) and ACN (B). The column was interfaced with a Bruker Impact II quadrupole-time of flight (Q-TOF) mass spectrometer and ionized via CaptiveSpray with ACN NanoBooster (FIG. 33).

Figure 34:
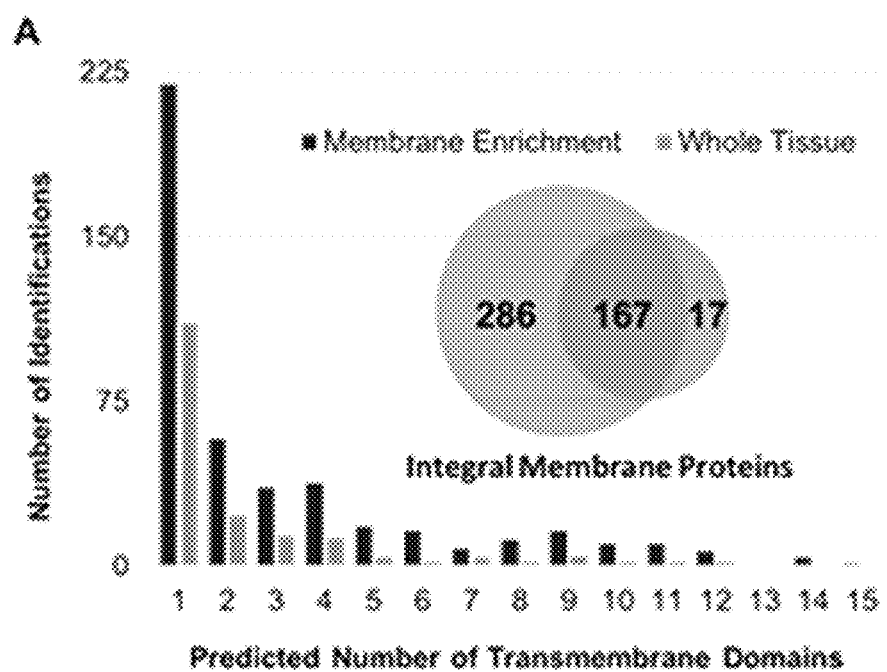
FIG. 34—Azo was used for whole tissue extraction or to solubilize the protein pellet after cloud point enrichment. Panel (A), plot of the predicted number of transmembrane domains for identified proteins. Overall 286 new identifications were observed after enrichment demonstrating Azo's ability to solubilize hydrophobic proteins. Panel (B), table of representative membrane proteins with a high number of transmembrane domains that were solubilized by Azo.

Membrane Protein Enrichment, Digestion, and LC-MS Analysis. HEK cells from a single 10-cm plate were lysed with 1 mL of buffer (2% Triton X-114, 25 mM ABC, 25 mM methionine, and 1 mM phenylmethylsulfonyl fluoride). After 1 h incubation at 4° C., cells were centrifuged for 5 min at 16,000×g at 4° C. The supernatant was removed and heated to 37° C. to induce the cloud point (Bordier et al., 1981, J Biol Chem, 256:1604-1607). The mixture was centrifuged at 3,000×g at room temperature (RT) and the top layer was removed. The bottom triton layer was washed with cold buffer (25 mM ABC and 25 mM methionine) and the cloud point procedure was repeated. The triton layer was precipitated with 4 v of acetone overnight. 0.1% Azo was added to solubilize the precipitated pellet and the sample was briefly sonicated in a water bath. The protein concentration was determined by BCA assay using BSA as a standard. 100 µg of protein was reduced, alkylated, digested ON, and analyzed as described above (a 90 min gradient from 5-45% was used for LC separation) (FIG. 34).

Figure 26:
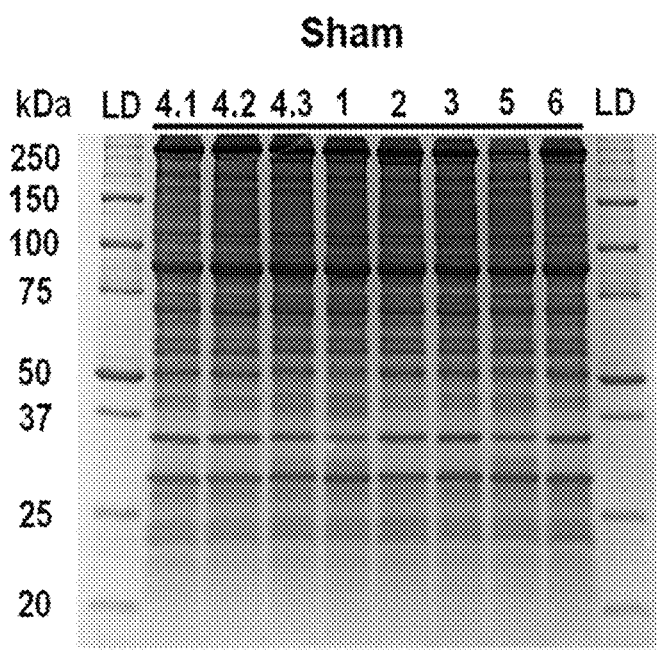
FIG. 26—Whole-tissue cardiac extraction reproducibility using Azo in a bottom-up proteomic experiment. Blot analysis of extractions from 6 swine were performed using 0.5% Azo.
Figure 27:
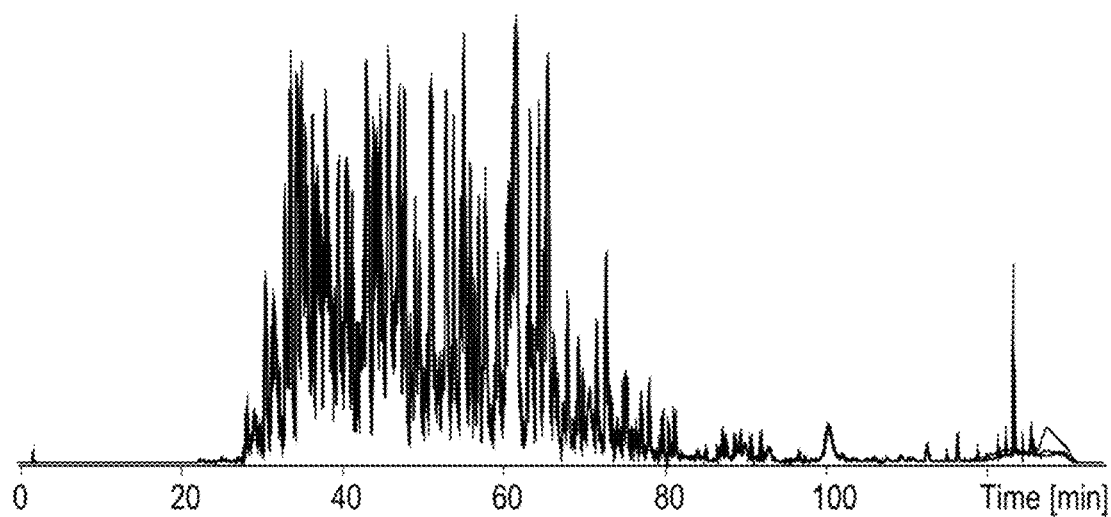
FIG. 27—Base peak chromatogram overlap of three whole-tissue cardiac extractions in a bottom-up proteomic experiment.
Figure 28:
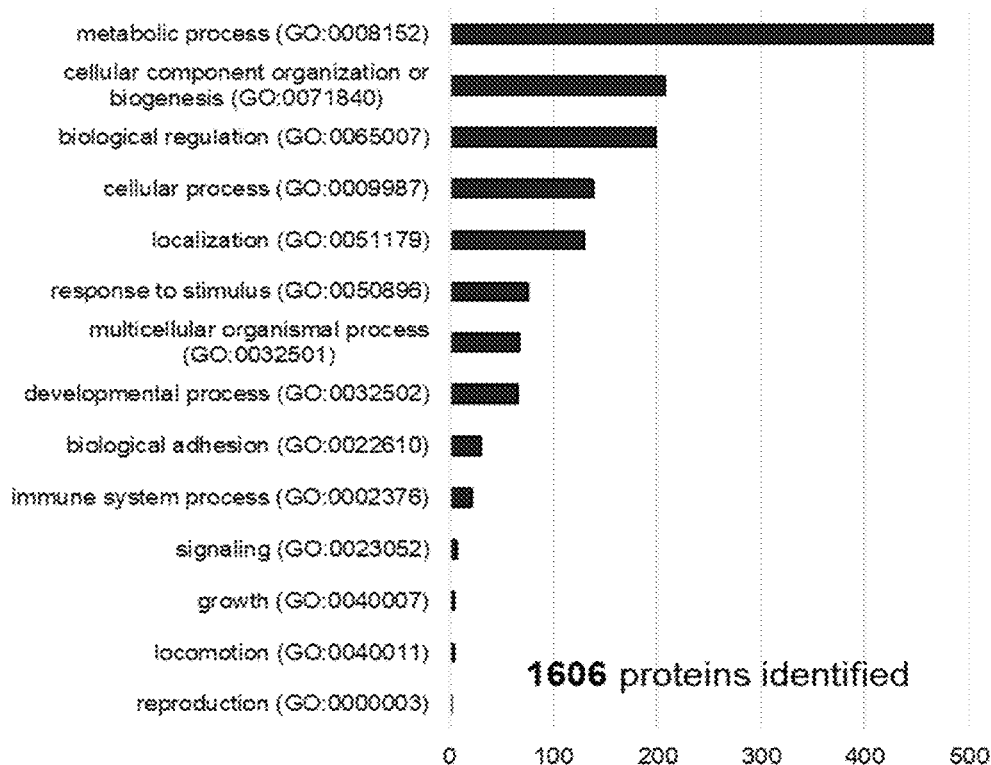
FIG. 28—Gene ontology for protein identified from swine cardiac tissue using the Azo platform in a bottom-up proteomic experiment.

Data Analysis. For LC-MS/MS experiments, data was analyzed using MaxQuant (Version 1.5.7.4) searching against the *Homo sapiens* reviewed Uniprot databased (3/12/2019) or *Sus scrofa* unreviewed (11/27/2018). A 1% FDR was set for protein and peptide identifications. Carbamiomethylation of cysteine was set for fixed modification while N-terminal acetylation and methionine oxidation were set as variable modification. Two missed cleavages were allowed. All other setting were based on the default parameters for Q-TOF instrument Additional analysis of cardiac proteins. In addition to the above, about 20 mg of tissue, from 6 swine hearts, was homogenized in 0.5% Azo (FIG. 26). 50 µg of protein were reduced, alkylated, and trypsinized overnight. The samples were irradiated for 3 min with a 100 W mercury vapor lamp to degrade the surfactant. The samples were centrifuged and ~4 µg of peptides were loaded onto a $C_{18}$ column. The peptides were separated (FIG. 27) and analyzed by mass spectrometry. Protein identifications were determined using MaxQuant (FIG. 28). Good reproducibility was observed, using both sodium dodecyl sulfate polyacrylamide gel electrophoresis (SDS-PAGE) and LC-MS/MS analysis, across tissue replicated using this method. Importantly, no sample clean-up (e.g. solid phase extraction) was required before LC-MS/MS analysis making this method more high-throughput than urea-assisted in-solution digestion or filter aided sample preparation (FASP).

Results. Overall, Azo enabled reproducible extraction, rapid digestion (1 hr), and LC-MS/MS analysis of proteins extracted from cardiac tissue. These results show reproducible Azo-aided tissue proteomics with future application in understanding the molecular mechanism in diseases.

Although Azo significantly facilitates protein extraction of proteins in both cell and tissue samples, a caveat in the use of strong extraction reagents (including SDS) for protein extraction is the resulting complex protein mixture leads to bias against certain protein species. For example, integral membrane proteins, which are hydrophobic and generally expressed at lower levels, are generally underrepresented in proteomics studies (Zhang et al., 2015, Molecular & cellular proteomics: MCP, 14:2411-2453; and Helbig et al., 2010, J Proteomics, 73:868-878). In this study, Triton X-114 was used to perform a cloud point extraction to enrich membrane protein from HEK cells with a single extraction (Bordier et al., 1981, J Biol Chem, 256:1604-1607; and Pavic et al., Biochim Biophys Acta, 1860, 1710-1715). However, Triton surfactants are incompatible with MS analysis and require surfactant removal prior to MS analysis (Loo et al., 1994, Protein Science, 3:1975-1983). Here, Azo solubilized precipitated protein pellets enriched with integral membranes for a more effective analysis of this important class of proteins. After successfully solubilizing and digesting the protein pellet, 453 integral membrane proteins were observed in the enriched sample (results from a two LC-MS/MS experiments), compared to only 184 in the Azo whole cell lysate sample without enrichment (result from combined three LC-MS/MS using 1 hr digestion and three LC-MS/MS using an ON digestion) (FIG. 34, panel A). Moreover, 29 proteins were identified with 10+predicted transmembrane domains (TMD) (Krogh et al., 2001, J Mol Biol, 305:567-580), such as NADH-ubiquinone oxidoreductase chain 5 (15 TMD), verifying Azo can solubilize and aid in the digestion of highly hydrophobic species (FIG. 34, panel B).

This example demonstrates that Azo is compatible with bottom-up proteomics without an additional clean-up step after UV degradation of the surfactant, and that the use of Azo drastically accelerates the rate of enzymatic digestion. Importantly, Azo enables highly reproducible protein digestion results within only 1 h for high-throughput bottom-up proteomic analysis of cell and tissue lysates. Considering that protein digestion is the most time-consuming step in bottom-up proteomics and is generally performed for >9 h to ensure high digestion efficiency (Link et al., 1999, Nature Biotechnology, 17:676; and Proc et al., 2010, Journal Proteome Research, 9:5422-5437), shortening this step in the workflow without loss of digestion efficiency would dramatically improve sample throughput, permitting bottom-up analyses to a wide range of applications especially those require high-throughput analysis in clinical diagnostics. Moreover, an Azo-aided bottom-up workflow is developed for effective solubilization of membrane proteins for high-throughput membrane proteomics. Overall this technology could greatly improve the bottom-up workflow where digestion is typically performed overnight making it more viable as a clinical diagnostic tool. Taken together with the additional experiments described above, the present example shows the unique utility of Azo as an "all-in-one" MS-compatible surfactant for both top-down and bottom-up proteomics, with streamlined workflows for high-throughput proteomics amenable to clinical applications.

Example 6—Photo-Cleavable Surfactant for Extracellular Matrix Proteomics

The extracellular matrix (ECM) provides an architectural meshwork for surrounding cells. It plays a critical role in cancers, regenerative medicine and cardiovascular diseases, where the composition and organization contribute greatly to disease progression. Mass spectrometry (MS) is an ideal methodology to profile proteome changes and promote further understanding of ECM biology. It is therefore critical to develop robust, universal strategies to facilitate analysis of this important class of proteins to develop better therapeutics. However, the current protocols for MS analysis of the ECM are challenging due to extremely poor solubility of the ECM, long labor intensive workflows including multiple digestions and offline sample clean-up of MS incompatible reagents. To address these challenges, a novel, high-throughput strategy for ECM proteomics was developed using a photo-cleavable, anionic surfactant (Azo). Azo greatly improves the solubility of the ECM, facilitates effective, quick enzymatic digestion without the need for harsh chemical reagents, and requires minimal sample cleanup for a user-friendly bottom-up mass spectrometry-based characterization method.

Figure 37:
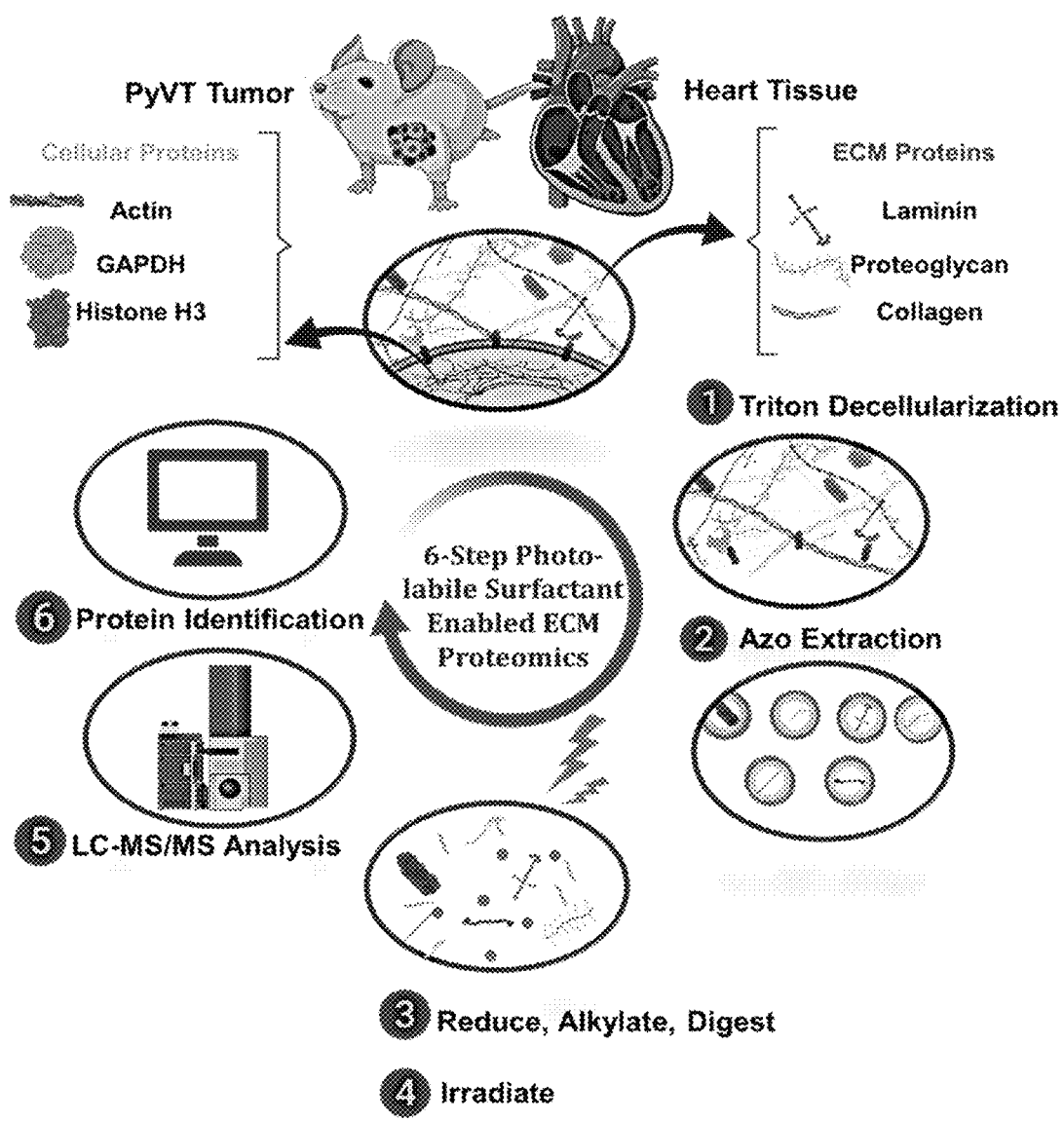
FIG. 37—High-throughput workflow for Azo-aided Extracellular Matrix (ECM) bottom-up proteomics.

Decellularization, ECM Protein Extraction, Digestion and RPLC-MS/MS. Frozen left and right ventricle tissue from human and swine hearts were harvested and flash frozen in accordance with the University of Wisconsin-Madison Institutional Review Board. Additionally, polyomavirus middle T (PyVT) transgenic, metastatic breast cancer mouse tissue was removed and flash frozen in accordance with the University of Wisconsin-Madison animal use and care committee. A rotor stator homogenizer (Pro Sceintific Inc.) was used to homogenize the sample of ice in 2% Triton X-100 or LiCI for tissue decellularization. Following centrifugation at 16,100×g at 4° C. for five minutes, the remaining pellet was washed with ammonium bicarbonate, centrifuged again, and the supernatant was discarded. The pellet was washed a total of five times to remove the Triton X-100 and any residual soluble proteins. Next, the insoluble tissue pellet was homogenized in 0.5% Azo extraction buffer (FIG. 37).

The protein concentration was determined with a BCA protein assay using Albumin as a standard. 140 µg of protein was then reduced with 10 mM dithiothreitol (DTT) and alkylated with 25 mM iodoacetamide and digested with trypsin at a 1:50 enzyme: protein concentration. The reaction was quenched with formic acid and UV-irradiation with a 100 W mercury lamp was used to rapidly degrade the surfactant. Approximately, 30 µg of peptides were separated using a $C_{18}$ column with 0.2% formic acid in Water and ACN as mobile phase A and B respectively. Eluted peptides were electrospray into a Bruker Impact II (ESI-QUAD-TOF) for MS analysis. Top 30 most intense peaks were selected for collisionally activated dissociation (CAD). Peptide spectral matching was performed against MS/MS spectra with Mascot (Ver. 2.5) against UniProt databases (*Homo sapiens* downloaded Jun. 16, 2015, *Mus musculus* downloaded May 4, 2018 and *Sus scrofa* downloaded Jun. 27, 2013) and the following parameters; two missed cleavages of trypsin; peptide precursor tolerance of 0.6 Da and MS/MS tolerance of 0.3 Da.; variable modifications: N-terminal acetylation, carbamidomethylation of cysteine, methionine oxidation, deamidation of asparagine and hydroxylation of proline. MaxQuant (1.7.5.4) was used with two missed cleavages of trypsin; variable modifications: N terminal acetylation, carbamidomethylation of cysteine, methionine oxidation, deamidation of asparagine and hydroxylation of proline. All other settings were set to the default.

SDS-PAGE. Laemmli buffer supplemented with 100 mM DTT was added to decellularization and Azo extracts. Samples were boiled at 97° C. for 3 minutes and separated at 155 V on an in-house cast 8% polyacrylamide gel.

Offline high-pH reverse-phase fractionation. Following trypsin digestion, 100 µg of Azo extraction was transferred to an equilibrated Thermo Scientific™ Pierce™ High pH Reversed-Phase Peptide Fractionation Kit spin column. Peptides were bound under aqueous conditions and a step gradient of increasing concentrations of acetonitrile (5-50%) was used elute bound peptides into eight fractions according to the manufactures instructions. Fractions were left unpooled or pooled (#1&5, 2&6, 3&7, 4&8). Fractions were dried in a vacuum centrifuge, reconstituted in 0.2% formic acid, and analyzed by LC-MS/MS as stated above.

Figure 38:
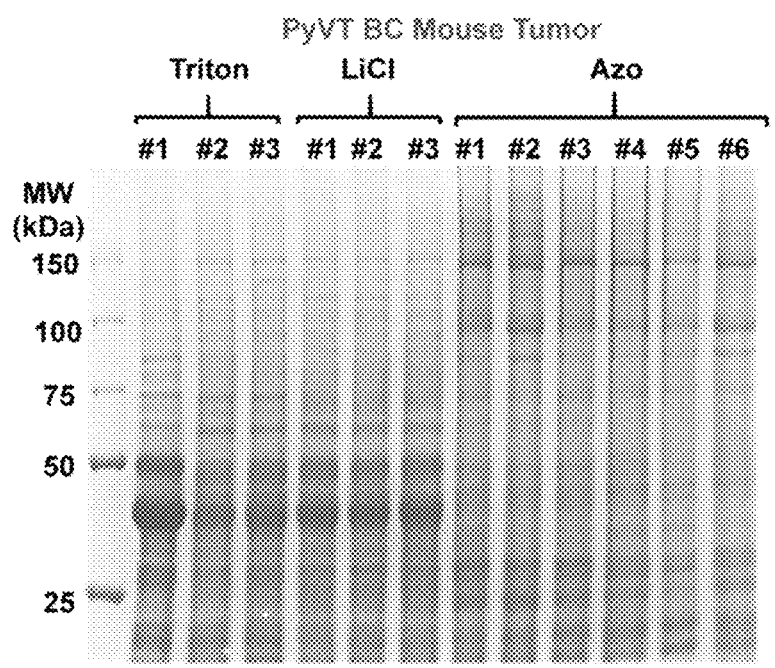
FIG. 38—Whole-tissue ECM extraction reproducibility using Azo. Extractions from 6 tumor aliquots decellularized using Triton (#1-3) or LiCI extraction buffers (#1-3), following by extraction with 0.5% Azo (#1-6).

Development of robust, reproducible sample preparation method for decellularization and solubilization of ECM proteins. First, a decellularization strategy was developed to purify the ECM by depleting cellular material and decreasing sample complexity thus allowing for the detection of lower abundance proteins. ECM proteins and ECM-associated proteins are challenging to solubilize, enzymatically digest, and in some cases are relatively lower abundance compared to cellular proteins, which prevents their identification of ECM using a traditional bottom-up approach. The present approach first homogenizes tissue in LiCI or Triton X-100 decellularization buffers for depletion of cellular proteins, followed by extraction of the insoluble ECM proteins using Azo (FIG. 37). This approach enhances the current lengthy subcellular fractionation kits and traditional multi-day decellularization processes. Good reproducibility was observed, using sodium dodecyl sulfate-polyacrylamide gel electrophoresis (SDS-PAGE) analysis, across decellularized and Azo tissue extraction replicates using this method (FIG. 38). Following trypsin digestion and LC-MS/MS analysis, ECM proteins identified in the Triton, LiCI and Azo extraction fractions were observed. Many soluble proteoglycans and associated extracellular matrix proteins, like Annexins, were observed in both fractions were found in the Triton, LiCI, and Azo fractions while more insoluble fibrous proteins, like Fibrinogen, were only found in the Azo fraction. Notably, the decellularization fractions are often ignored in ECM protocols; however, the present results show solubility of a number of ECM proteins in the decellularization fractions, warranting analysis of both extracts. Some enrichment of the ECM is also seen upon decellularization.

Figure 39:
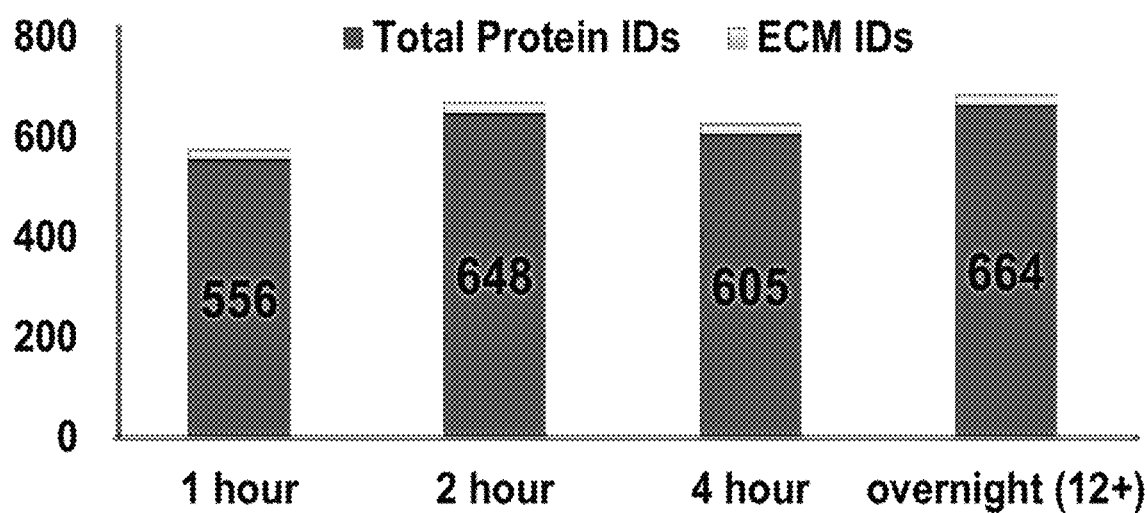
FIG. 39—Time-course for trypsin digestion of *Sus scrofa* Azo extraction. Mascot Total Protein Identification (ID) and ECM IDs after 1, 2, 4 hour and overnight trypsin digestion. There was no appreciable difference in protein IDs across time points.

Next, it was demonstrated that Azo can facilitate an accelerated digestion time for ECM proteins. 140 µg of *Sus scrofa* heart Azo extractions were digested with trypsin and quenched the reaction at 1 hour, 2 hours, 4 hours and overnight. The number of Mascot protein identifications from each sample was used as a benchmark for digestion efficiency. A two-hour trypsin digestion yielded optimal results, with no significant increase in ECM protein identifications with increasing time intervals (FIG. 39). Overall, Azo shows rapid, efficient digestion of ECM proteins. This greatly accelerates the time of trypsin digestion, which is typically performed overnight for ECM proteomics. The workflow presented does not include MS incompatible reagents like urea and SDS, removing the need for a desalting step or sample clean-up post-digestion.

Importantly, the Azo-assisted ECM proteomics method addresses several challenges with current ECM proteomics workflows. First, Azo extracts enriched for ECM proteins require no sample clean-up or desalting (e.g., solid phase extractions or precipitation) prior to LC-MS/MS analysis. Elimination of these steps makes this method more high-throughput than traditional protocols utilizing SDS and other MS incompatible detergents. It also eliminates potential steps for sample loss and method irreproducibility. Furthermore, the need for digestion with toxic reagents like cyanogen bromide, multi-enzyme digestions, and overnight digestion protocols is eliminated. Overall, this protocol requires less sample handling, making it particularly user-friendly. ECM proteomics workflows are notoriously lengthy, whereas our protocol is rapid, increasing the throughput. As an estimate, traditional ECM sample preparation protocols for mass spectrometry take several days or even weeks. The approach described in this example provides an effective, high-throughput workflow that can easily be completed in a day.

Offline high-pH fractionation coupled to RPLC-MS/MS for global ECM proteomics. For a more global coverage, digestions were fractionated using an offline high-pH fractionation prior to online RPLC-MS/MS. Fractionation reduced the overall sample complexity and improving the ability to identify low-abundant peptides and ECM proteins (FIG. 40). Pooling was accessed to determine if a large difference was seen in ECM protein identifications. A pooled approach yielded the largest number of identifications. Importantly, the separation takes fifteen minutes with a benchtop centrifuge, whereas other multi-dimensional separations often collect a large number of fractions and subsequently a lot of instrument time is needed. Overall, the spin filter approach still enables similar coverage and significantly saves time on downstream LC-MS analysis time.

Azo Enabled Characterization of ECM proteome. ECM proteins from both core matrisome and associated divisions were identified. In addition, ECM proteins from all major classes including glycoproteins, proteoglycans, collagens, regulated, secreted and ECM affiliated proteins were cataloged. Lists were compiled for several one dimensional and two-dimensional LC-MS/MS analyses of mouse tumor extractions, providing a resource for targeted analysis. The Azo enabled ECM proteomics workflow also allows simultaneous profiling of proteins of interest ECM remodeling and disease progression seen in both cardiovascular disease and cancer. The method provides a simple, simultaneous approach to monitor additional proteins from other cellular locations that may interact downstream. String analysis reveals the expected enrichment of GO pathways involved in ECM mediated biological processes. A protein-protein interactome String analysis revealed expected enrichment of GO pathways involved in ECM mediated biological processes. A protein-protein interactome revealed aggregated networks of identified proteins in ECM organization, cell-matrix adhesion, and cell-substrate adhesion functional cellular processes. Relevant interactions within the network provide new directions for future experimental pathways of interest.

Conclusions. Although bottom-up proteomics is a widely used technology for characterizing the proteome, there are only very few published methodologies for ECM proteomics mainly due to the difficulty in solubilizing and digesting ECM proteins. The demand for new, user-friendly methodologies is seen with the increasing understanding and importance of the ECM in disease progression and development. However, the lack of user-friendly ECM proteomics methodologies is currently hindering analysis of this important sub-proteome. Current methods predominately suffer from the use of MS incompatible reagents including SDS or urea to solubilize the matrix. These methods also require time-consuming digestions and extensive clean-up steps prior to mass spectrometry (MS) analysis that can lead to sample loss. The best type of approach will depend on the particular proteins and tissue of interest as ECM composition can vary widely. This is the first demonstration of ECM proteomics utilizing the novel use of a photo-cleavable surfactant (Azo). The method enables reproducible protein extraction, digestion, and LC-MS/MS analysis in a highly streamlined fashion. In summary, the ECM pipeline presented here has broad applicability for utilization in studies pertaining to multiple types of diseased tissues and sites.

Example 7-Photo-Cleavable Surfactant as a Substitute for Sodium Dodecyl Sulfate in Gel Electrophoresis Given surfactants are instrumental in biological and biomedical research, it is envisioned that the photo-cleavable surfactants of the present invention will play an essential role in a myriad of proteomic studies, including those with clinically relevance. Additionally, the photo-cleavable surfactants of the present invention also can be used as a cleavable SDS-replacement in general biochemical applications, notably, in gel electrophoresis.

SDS-PAGE. As described above, an equal volume (7 µL) of each extraction was subsequently resolved using 12.5% SDS-PAGE with a voltage of 50 V for 30 min and 120 V for approximately 75 min. Proteins were visualized using Coomassie Brilliant Blue R-250.

Azo-PAGE. Similarly, gel electrophoresis was performed using Azo instead of SDS. The general electrophoresis conditions were as follows (see also Table 4 below): Azo Loading Dye (2x): 100 µL Tris (1M pH 6.8), 10 mg Azo, 200 µL Bromophenol blue (0.04% solution), 200 µL glycerol, 20 µL DTT (1M). Volume adjusted to 1 mL with water. Azo running buffer: 1.5 g Tris Base, 7.2 g Glycine, 2.5 g Azo. Adjusted to 1 L with water. 2.5 µg of BSA, B-casein, and RNase A or 10 µg of cardiac myofilament extract (Peng et al., 2014, Proteomics Clin Appl, 8:554-568) was then separated on a 1 mm, 12.5% polyacrylamide gel run at 150V.

TABLE 4

Composition of Acrylamide Gel for SDS/Azo-PAGE.

|  | 5 mL Resolving | 2 mL Stacking |
| --- | --- | --- |
| Water | 1.62 mL | 1.42 mL |
| 30% Acryalmide | 2.09 mL | 0.33 mL |
| 1.5M Tris | 1.25 mL | 0 mL |

TABLE 4-continued

Composition of Acrylamide Gel for SDS/Azo-PAGE.

|  | 5 mL Resolving | 2 mL Stacking |
| --- | --- | --- |
| 1M Tris | 0 mL | 0.25 mL |
| 10% APS | 0.05 mL | 0.02 mL |
| TEMED | 0.002 mL | 0.002 mL |

FIG. 9 shows the results of polyacrylamide gel electrophoresis (PAGE) using Azo (panels a and b) and SDS (panels c and d). Azo-PAGE analysis of (a) 2.5 µg bovine serum albumin (BSA), B-casein, and ribonuclease A (RNase A), and (b) myofilament cardiac tissue protein extract with Coomassie blue staining. SDS-PAGE analysis of (c) 2.5 µg BSA, β-Casein, and RNase A, and (d) myofilament cardiac tissue protein extract with Coomassie blue staining. As seen in FIG. 9, Azo-PAGE was able to produce comparable results to SDS-PAGE.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

The invention claimed is:

1. A photo-cleavable surfactant comprising: a) a hydrophilic head, b) a hydrophobic tail, and c) a photo-cleavable moiety covalently linking the hydrophilic head and hydrophobic tail, where the photo-cleavable moiety is able to release the hydrophilic head, release the hydrophobic tail, and/or break apart upon exposure to ultraviolet (UV) radiation, wherein the photo-cleavable surfactant has the formula:

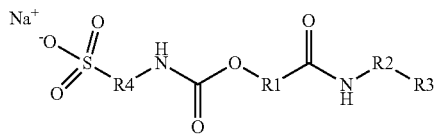

wherein

R1 is a substituted or unsubstituted aryl group having from 6 to 18 carbon atoms;

R2 is a substituted or unsubstituted alkylene or alkenylene group having from 2 to 18 carbon atoms;

R3 is a substituted or unsubstituted alkyl, alkenyl, or aryl group having from 1 to 6 carbon atoms; and R4 is a substituted or unsubstituted alkylene or alkenylene group having from 1 to 8 carbon atoms.

2. The photo-cleavable surfactant of claim 1, wherein the photo-cleavable surfactant remains stable at a pH of 4 or lower.

3. A photo-cleavable surfactant comprising: a) a hydrophilic head, b) a hydrophobic tail, and c) a photo-cleavable moiety covalently linking the hydrophilic head and hydrophobic tail, where the photo-cleavable moiety is able to release the hydrophilic head, release the hydrophobic tail, and/or break apart upon exposure to ultraviolet (UV) radiation, wherein the photo-cleavable surfactant has the formula

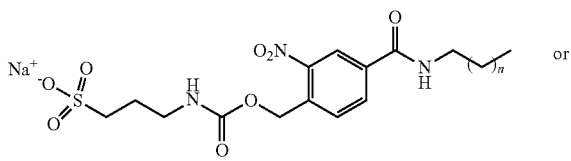

or

-continued

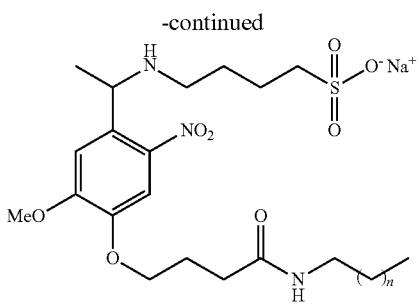

where n is an integer selected from 2 to 30.

4. A method for separating components in a sample solution using electrophoresis, said method comprising the steps of:

a) providing a porous gel having a first end and a second end and having one or more liquid buffers, wherein the one or more liquid buffers are able to conduct an electric current across the gel;

b) disposing the sample solution in the first end of the gel, wherein the sample solution further comprises a photo-cleavable surfactant comprising: i) a hydrophilic head, ii) a hydrophobic tail, and iii) a photo-cleavable moiety covalently linking the hydrophilic head and hydrophobic tail, where the photo-cleavable moiety is able to release the hydrophilic head, release the hydrophobic tail, and/or break apart upon exposure to ultraviolet (UV) radiation, wherein the photo-cleavable surfactant has the formula:

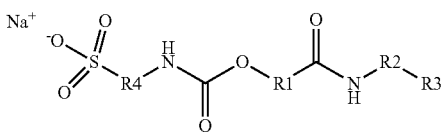

wherein

R1 is a substituted or unsubstituted aryl group having from 6 to 18 carbon atoms;

R2 is a substituted or unsubstituted alkylene or alkenylene group having from 2 to 18 carbon atoms;

R3 is a substituted or unsubstituted alkyl, alkenyl, or aryl group having from 1 to 6 carbon atoms; and R4 is a substituted or unsubstituted alkylene or alkenylene group having from 1 to 8 carbon atoms, and wherein the sample solution and the one or buffers comprise less than 0.1% sodium dodecyl sulfate (SDS) or urea; and c) applying an electric current across the first and second end of the porous gel, wherein the components in the sample solution will move from the first end of the porous gel toward the second end of the porous gel.

5. The method of claim 4, wherein the sample solution comprises one or more polypeptides, nucleic acids, or combinations thereof.

6. The method of claim 4, wherein the photo-cleavable surfactant has the formula

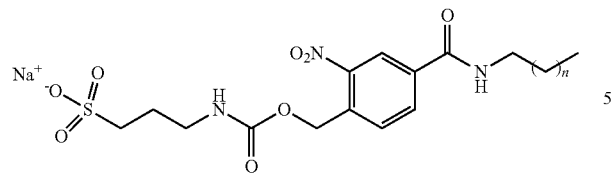
where n is an integer selected from 2 to 30.
* * * * *